United States Patent
Nomura et al.

(10) Patent No.: US 8,093,399 B2
(45) Date of Patent: Jan. 10, 2012

(54) BENZOXAZOLE DERIVATIVE, AND LIGHT-EMITTING ELEMENT, LIGHT-EMITTING DEVICE, AND ELECTRONIC DEVICE USING BENZOXAZOLE DERIVATIVE

(75) Inventors: Hiroko Nomura, Fukuoka (JP); Sachiko Kawakami, Kanagawa (JP); Nobuharu Ohsawa, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 170 days.

(21) Appl. No.: 12/553,290

(22) Filed: Sep. 3, 2009

(65) Prior Publication Data

US 2010/0060154 A1    Mar. 11, 2010

(30) Foreign Application Priority Data

Sep. 5, 2008  (JP) ................. 2008-228252
Mar. 3, 2009  (JP) ................. 2009-049170

(51) Int. Cl.
*C07D 413/10* (2006.01)
*B32B 9/00* (2006.01)
*H01J 1/62* (2006.01)

(52) U.S. Cl. ........ 548/224; 548/217; 428/690; 428/917; 313/504; 313/506

(58) Field of Classification Search .............. 548/217, 548/224; 428/690, 917; 313/504, 506
See application file for complete search history.

(56) References Cited

U.S. PATENT DOCUMENTS

| | | | | |
|---|---|---|---|---|
| 7,796,240 B2 * | 9/2010 | Nomura et al. | ............. | 356/32 |
| 7,838,128 B2 * | 11/2010 | Kawakami et al. | ............. | 428/690 |
| 7,875,879 B2 * | 1/2011 | Suzuki et al. | ............. | 257/40 |
| 7,880,019 B2 * | 2/2011 | Egawa et al. | ............. | 548/439 |
| 7,883,788 B2 * | 2/2011 | Kawakami et al. | ............. | 428/690 |
| 7,901,792 B2 * | 3/2011 | Egawa et al. | ............. | 428/690 |
| 7,927,720 B2 * | 4/2011 | Nomura et al. | ............. | 428/690 |
| 2010/0060155 A1 | 3/2010 | Seo et al. | | |

OTHER PUBLICATIONS

Baldo, M.A. et al, "Very High-Efficiency Green Organic Light-Emitting Devices Based on Electrophosphorescence," Applied Physics Letters, vol. 75, No. 1, Jul. 5, 1999, pp. 4-6.
Goldsmith, C.R. et al, "C-H Bond Activation by a Ferric Methoxide Complex: Modeling the Rate-Determining Step in the Mechanism of Lipoxygenase," J. Am. Chem. Soc., vol. 124, No. 1, 2002, pp. 83-96.
Onishi, T. et al., "A Method of Measuring an Energy Level," *High Molecular EL Materials—Development of Light-Emitting High Molecular Compounds* Kyoritsu Shuppan, Dec. 25, 2004, pp. 64-67 (with English translation, pp. 1-3).

* cited by examiner

*Primary Examiner* — Golam M M Shameem
(74) *Attorney, Agent, or Firm* — Husch Blackwell LLP

(57) ABSTRACT

Disclosed is a novel benzoxazole derivative which has high excitation energy, particularly high triplet excitation energy, and is a bipolar substance. A benzoxazole derivative represented by the following General Formula (G1) is provided.

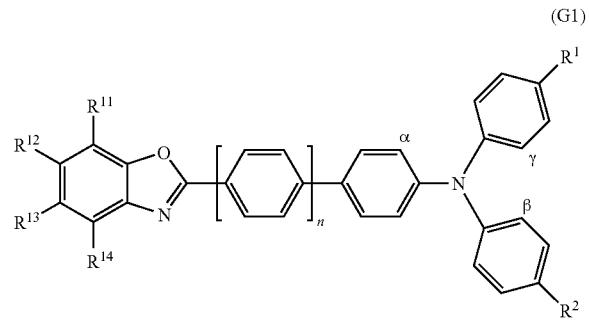

(G1)

In the formula, $R^1$ and $R^2$ independently represent a hydrogen atom, an alkyl group with 1 to 4 carbon atoms, or a substituted or unsubstituted aryl group with 6 to 13 carbon atoms, substituents of the substituted aryl group may be bonded to form a ring which may form a spiro ring structure, $R^{11}$ to $R^{14}$ independently represent a hydrogen atom, a halogen, an alkyl group with 1 to 4 carbon atoms, or an unsubstituted aryl group with 6 to 10 carbon atoms, a bond formed between any two of $\alpha$, $\beta$, and $\gamma$ forms a carbazole skeleton, and n is 0 to 3.

14 Claims, 28 Drawing Sheets

BENZOXAZOLE DERIVATIVE, AND LIGHT-EMITTING ELEMENT, LIGHT-EMITTING DEVICE, AND ELECTRONIC DEVICE USING BENZOXAZOLE DERIVATIVE

BACKGROUND OF THE INVENTION

1. Field of the Invention

The present invention relates to a benzoxazole derivative, and a light-emitting element, a light-emitting device and an electronic device each using the benzoxazole derivative.

2. Description of the Related Art

In recent years, research and development of light-emitting elements using electroluminescence have been extensively conducted. In the basic structure of such a light-emitting element, a layer including a light-emitting substance is interposed between a pair of electrodes. By applying a voltage to this element, light emission can be obtained from the light-emitting substance.

Since this type of light-emitting element is a self-luminous type, it has advantages over a liquid crystal display in that visibility of a pixel is high and that no backlight is needed. Therefore, light-emitting elements are thought to be suitable as flat panel display elements. Further, such a light-emitting element also has advantages in that the element can be formed to be thin and lightweight and that response speed is very high.

Further, since this type of a light-emitting element can be formed to have a film shape, surface light emission can be easily obtained. This feature is difficult to realize with point light sources typified by a filament lamp and an LED or with linear light sources typified by a fluorescent light. Therefore, such light-emitting elements also have a high utility value as surface light source that can be applied to lighting apparatuses or the like.

Light-Emitting elements using electroluminescence are broadly classified according to whether they use an organic compound or an inorganic compound as a light-emitting substance. When an organic compound is used as a light-emitting substance, by application of a voltage to a light-emitting element, electrons and holes are injected into a layer including the light-emitting organic compound from a pair of electrodes, whereby a current flows. Then, carriers (i.e., electrons and holes) recombine to place the light-emitting organic compound into an excited state. The light-emitting organic compound returns to a ground state from the excited state, thereby emitting light.

Because of such a mechanism, the light-emitting element is called a current-excitation light-emitting element. Note that an excited state of an organic compound can be of two types: a singlet excited state and a triplet excited state, and luminescence from the singlet excited state (S*) is referred to as fluorescence, and luminescence from the triplet excited state (T*) is referred to as phosphorescence. Furthermore, it is thought that the ratio of S* to T* in a light-emitting element is statistically 1:3.

At room temperature, a compound that converts a singlet excited state into luminescence (hereinafter referred to as a fluorescent compound) exhibits only luminescence from a singlet excited state (fluorescence), not luminescence from a triplet excited state (phosphorescence). Therefore, the internal quantum efficiency (ratio of generated photons to injected carriers) of a light-emitting element using a fluorescent compound is thought to have a theoretical limit of 25% on the basis that S*:T*=1:3.

On the other hand, by using a compound that converts a triplet excited state into luminescence (hereinafter referred to as a phosphorescent compound), internal quantum efficiency can be improved from 75 to 100% theoretically. That is, emission efficiency can be three to four times as high as that of a fluorescent compound. From such a reason, in order to achieve a light-emitting element with high efficiency, a light-emitting element using a phosphorescent compound has been actively developed recently (e.g., see Non Patent Document 1).

When a light-emitting layer of a light-emitting element is formed using a phosphorescent compound as described above, in order to suppress concentration quenching of the phosphorescent compound or quenching due to triplet-triplet annihilation, the light-emitting layer is often formed so that the phosphorescent compound is dispersed in a matrix including another substance. In that case, a substance serving as a matrix is referred to as a host material, a substance that is dispersed in a matrix, such as a phosphorescent compound, is referred to as a guest material.

When a phosphorescent compound is used as a guest material, a host material is needed to have triplet excitation energy (an energy difference between a ground state and a triplet excited state) higher than the phosphorescent compound. It is known that CBP which is used as a host material in Non-Patent Document 1 has higher triplet excitation energy than a phosphorescent compound which exhibits emission of green to red light, and is widely used as a host material of the phosphorescent compound.

However, although CBP has high triplet excitation energy, it is poor in ability to receive holes or electrons; therefore, there is a problem in that driving voltage gets higher. Therefore, a substance that has high triplet excitation energy and also can easily accept or transport both holes and electrons (i.e. a bipolar substance) is required as a host material for a phosphorescent compound.

Furthermore, because singlet excitation energy (difference in energy between a ground state and a singlet excited state) is greater than triplet excitation energy, a material that has high triplet excitation energy will also have high singlet excitation energy. Consequently, a substance that has high triplet excitation energy is also useful in a light-emitting element formed using a fluorescent compound as a light-emitting substance.

REFERENCE

Non-Patent Document

[Non-Patent Document 1] M. A. Baldo, etc., *Applied Physics Letters*, vol. 75, No. 1, pp. 4-6, 1999

SUMMARY OF THE INVENTION

In view of the foregoing, an object of the present invention is to provide, a novel benzoxazole derivative as a substance having high excitation energy, particularly as a substance having high triplet excitation energy, which is also a bipolar substance. Another object of the present invention is to improve element characteristics of a light-emitting element by applying the novel benzoxazole derivative to the light-emitting element. Still another object of the present invention is to provide a light-emitting device and an electronic device each having low power consumption and low driving voltage.

An embodiment of the present invention is a benzoxazole derivative represented by the following General Formula (G1).

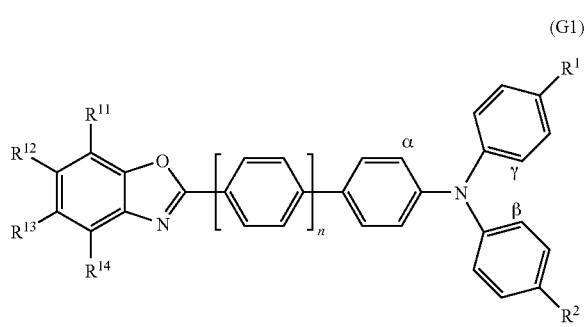

(G1)

In the formula, $R^1$ and $R^2$ independently represent any of a hydrogen atom, an alkyl group having 1 to 4 carbon atoms, and a substituted or unsubstituted aryl group having 6 to 13 carbon atoms. Note that $R^1$ and $R^2$ may have a spiro ring structure. Further, $R^{11}$ to $R^{14}$ independently represent any of a hydrogen atom, a halogen, an alkyl group having 1 to 4 carbon atoms, and an unsubstituted aryl group having 6 to 10 carbon atoms. Furthermore, a bond is formed between any two of α, β, and γ to form a carbazole skeleton. Note that n is 0 to 3.

An embodiment of the present invention is a benzoxazole derivative represented by the following General Formula (G2).

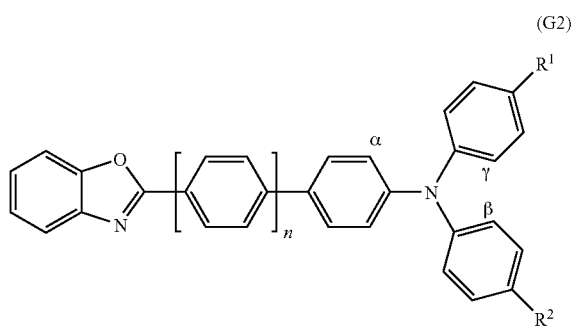

(G2)

In the formula, $R^1$ and $R^2$ independently represent any of a hydrogen atom, an alkyl group having 1 to 4 carbon atoms, and a substituted or unsubstituted aryl group having 6 to 13 carbon atoms. Note that $R^1$ and $R^2$ may have a spiro ring structure. Furthermore, a bond is formed between any two of α, β, and γ to form a carbazole skeleton. Note that n is 0 to 3.

An embodiment of the present invention is a benzoxazole derivative represented by the following General Formula (G3).

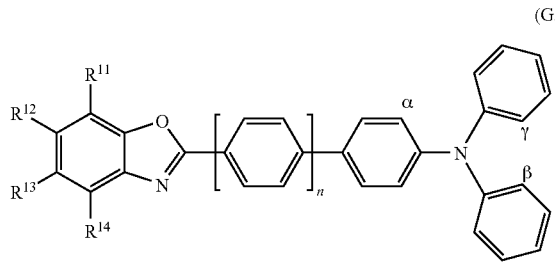

(G3)

In the formula, $R^{11}$ to $R^{14}$ independently represent any of a hydrogen atom, a halogen, an alkyl group having 1 to 4 carbon atoms, and an unsubstituted aryl group having 6 to 10 carbon atoms. Furthermore, a bond is formed between any two of α, β, and γ to form a carbazole skeleton. Note that n is 0 to 3.

Note that the above-described benzoxazole derivatives of the present invention have a light-emitting property. Accordingly, another structure of the present invention is a light-emitting element having, between a pair of electrodes, an EL layer which includes any of the above-described benzoxazole derivatives.

Further, the benzoxazole derivatives of the present invention have high excitation energy and can transport both hole and electrons. Therefore, the benzoxazole derivatives of the present invention are suitable for use as a host material of a light-emitting layer included in an EL layer. Accordingly, another structure of the present invention is a light-emitting element having, between a pair of electrodes, an EL layer in which a light-emitting layer includes any of the above-described benzoxazole derivatives and a light-emitting substance.

As the above light-emitting substance, a phosphorescent compound is particularly preferable since the benzoxazole derivatives of the present invention have high triplet excitation energy. With such a structure, a light-emitting element that is excellent in emission efficiency and driving voltage can be obtained.

Furthermore, another structure of the present invention is a light-emitting device formed using any of the above-described light-emitting elements and an electronic device formed using the light-emitting device.

The present invention also covers a light-emitting device having any of the above-described light-emitting elements and an electronic device having the light-emitting device. Note that the term "light-emitting device" in this specification includes an image display device, a light-emitting device, or a light source (including a lighting apparatus). Further, the following are all included in the "light-emitting device": a module in which a connector, for example, a flexible printed circuit (FPC), a tape automated bonding (TAB) tape, or a tape carrier package (TCP) is attached to a light-emitting device; a module provided with a printed wiring board at the end of the TAB tape or the TCP; and a module in which an integrated circuit (IC) is directly mounted to a light-emitting element by chip on glass (COG) method.

According to the present invention, benzoxazole derivatives which have high excitation energy, particularly high triplet excitation energy, and are also bipolar substances can be obtained. In addition, by forming a light-emitting element using any of the benzoxazole derivatives of the present invention, the light-emitting element with high current efficiency can be formed.

Furthermore, by using such a light-emitting element, a light-emitting device and an electronic device which have low power consumption and low driving voltage can be obtained.

DETAILED DESCRIPTION OF THE INVENTION

Figure 1A:
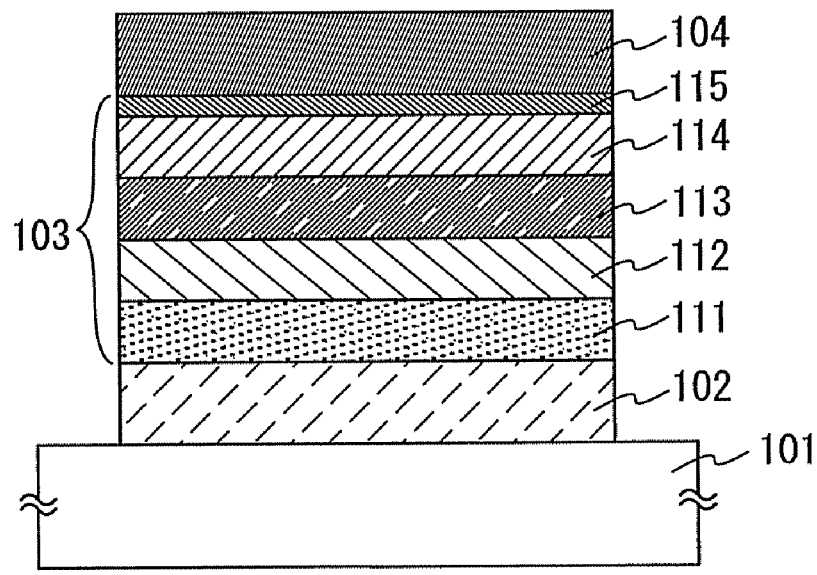
FIGS. 1A and 1B each illustrate a stack structure of a light-emitting element according to Embodiment 2.

Hereinafter, embodiments of the present invention will be described using the accompanying drawings. Note that the present invention is not limited to the description below, and the modes and details of the present invention can be easily modified in various ways by those skilled in the art without departing from the spirit and scope of the present invention. Therefore, the embodiments of the present invention should not be construed as being limited to the description of the embodiment modes and examples below.

Embodiment 1

In Embodiment 1, the benzoxazole derivatives of the present invention will be described.

An embodiment of the present invention is the benzoxazole derivative represented by General Formula (G1).

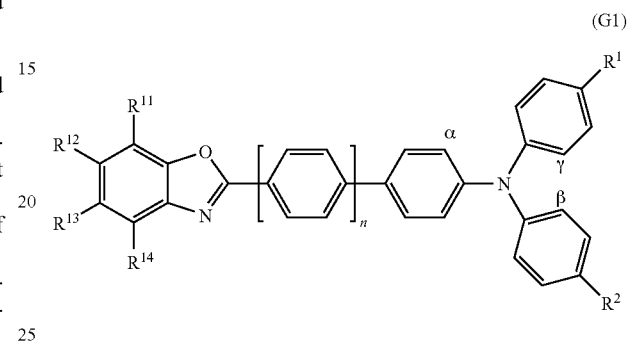

(G1)

In the formula, $R^1$ and $R^2$ independently represent a hydrogen atom, an alkyl group with 1 to 4 carbon atoms, or a substituted or unsubstituted aryl group with 6 to 13 carbon atoms. Note that substituents of the substituted aryl group may be bonded to form a ring which may form a spiro ring structure. Further, $R^{11}$ to $R^{14}$ independently represent a hydrogen atom, a halogen, an alkyl group with 1 to 4 carbon atoms, or an unsubstituted aryl group with 6 to 10 carbon atoms. Furthermore, a bond formed between any two of α, β, and γ forms a carbazole skeleton. Note that n is 0 to 3.

As specific structures of $R^1$ and $R^2$ in General Formula (G1), there are substituents represented by Structural Formulae (1-1) to (1-25).

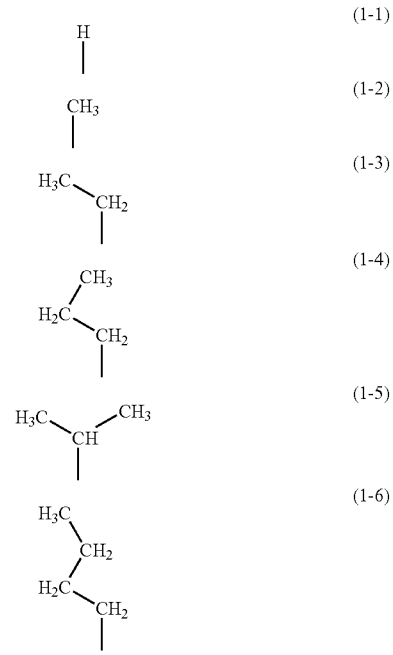

(1-7) 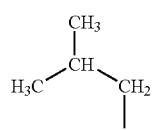
(1-8) 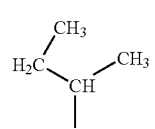
(1-9) 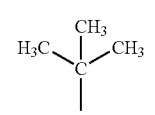
(1-10) 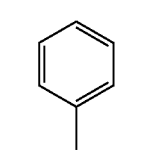
(1-11) 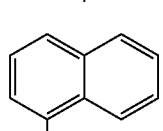
(1-12) 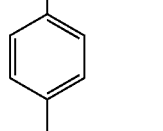
(1-13) 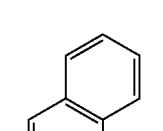
(1-14) 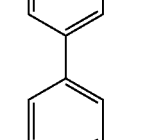
(1-15) 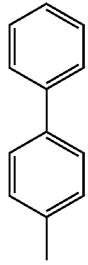
(1-16) 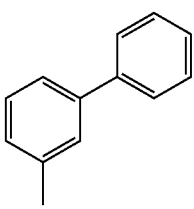
(1-17) 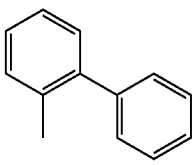
(1-18) 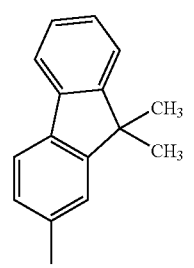
(1-19) 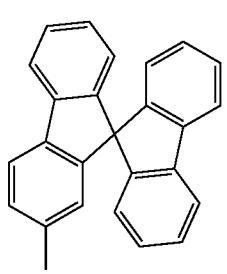
(1-20) 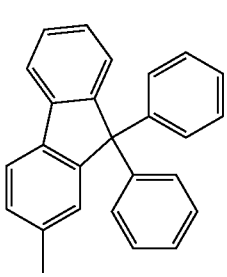

-continued (1-21) 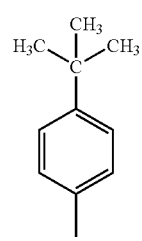

(1-22) 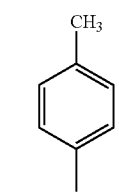

(1-23) 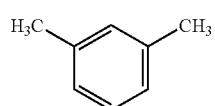

(1-24) 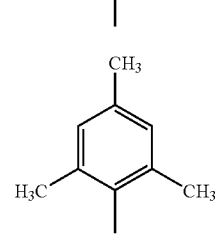

(1-25) 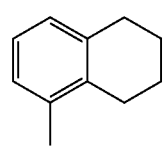

As specific structures of $R^{11}$ to $R^{14}$ in General Formula (G1), there are substituents represented by Structural Formulae (2-1) to (2-16).

(2-1) H—

(2-2) F—

(2-3) Cl—

(2-4) Br—

(2-5) I—

(2-6) CH₃—

(2-7) 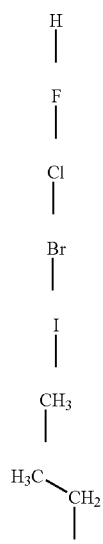

-continued (2-8) 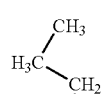

(2-9) 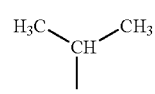

(2-10) 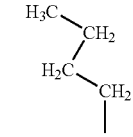

(2-11) 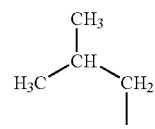

(2-12) 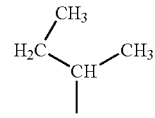

(2-13) 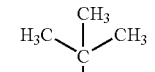

(2-14) 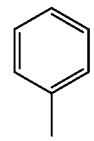

(2-15) 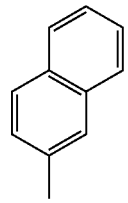

(2-16) 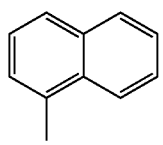

Specific examples of the benzoxazole derivatives of the present invention which are represented by General Formula (1) include, but not limited to, benzoxazole derivatives represented by Structural Formulae (100) to (433).

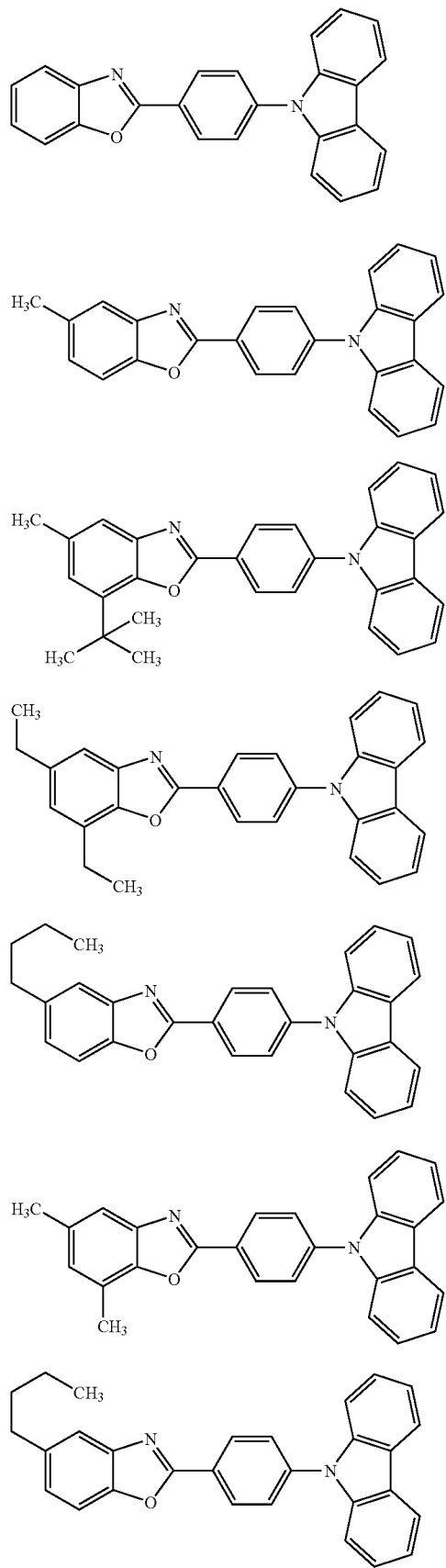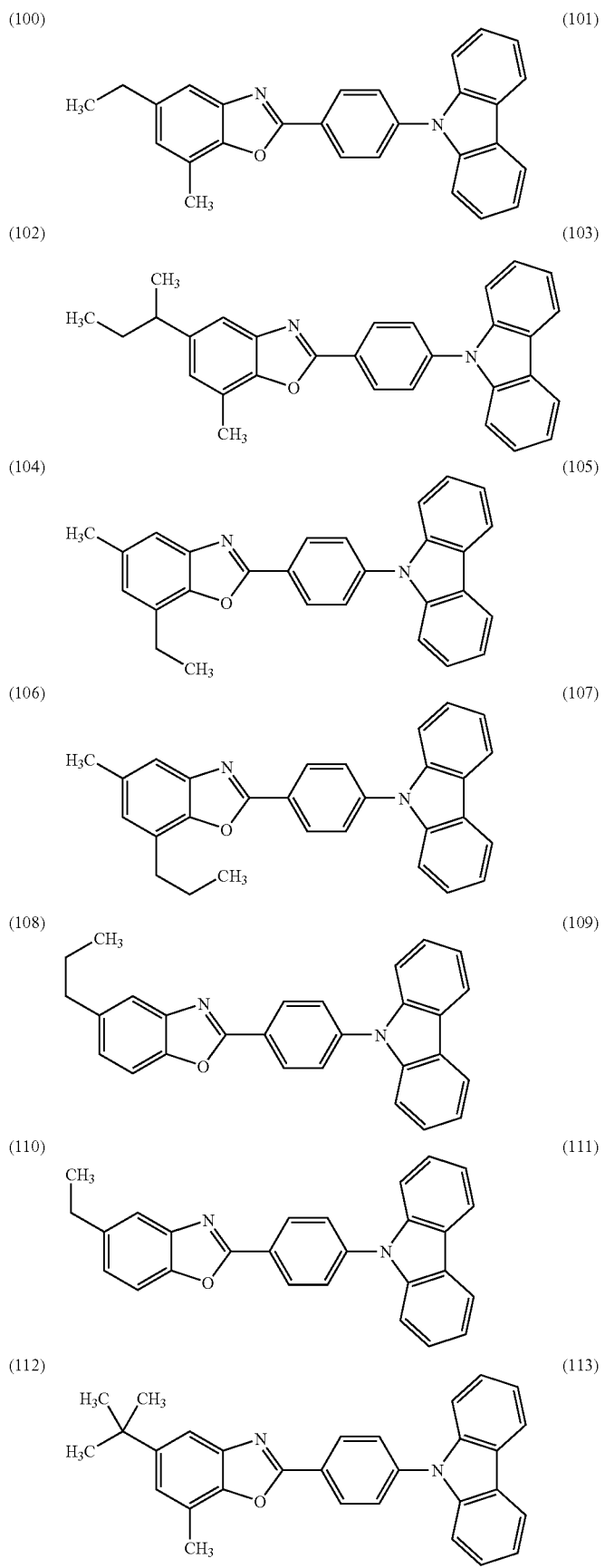

-continued
(114) 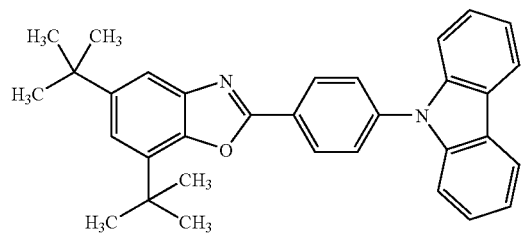
(115) 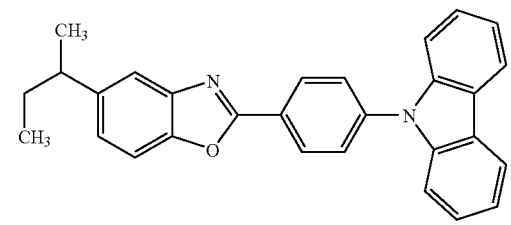
(116) 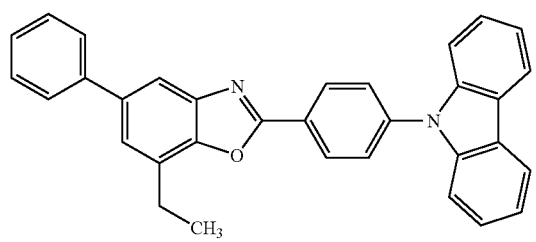
(117)
(118) 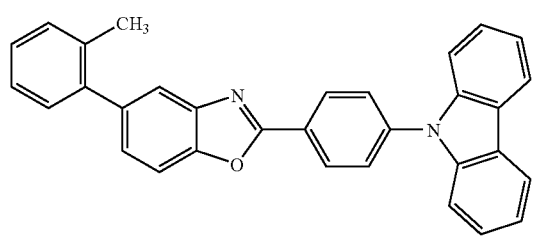
(119) 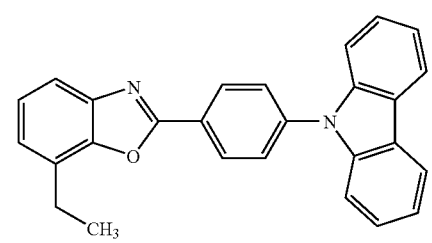
(120) 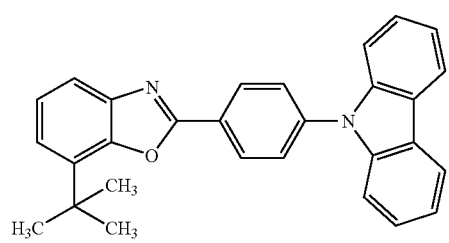
(121) 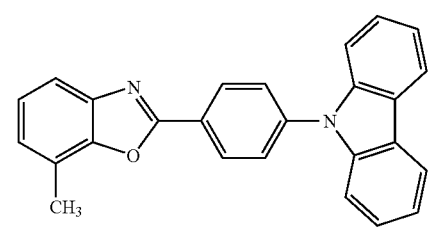
(122) 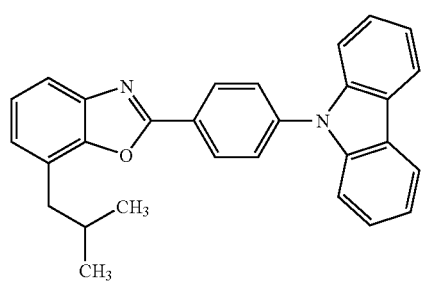
(123) 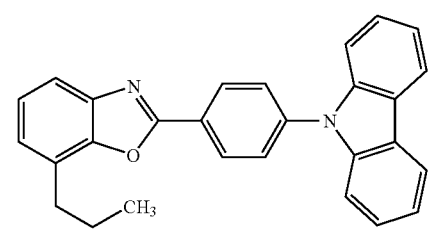
(124) 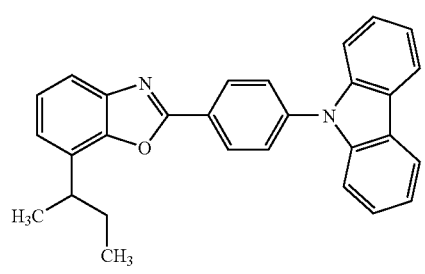
(125) 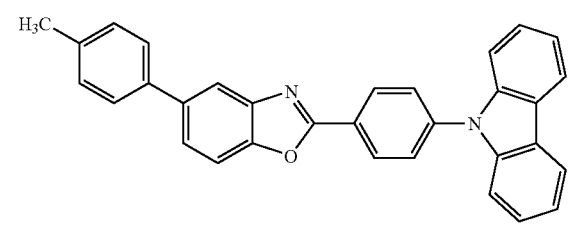

-continued
(126) 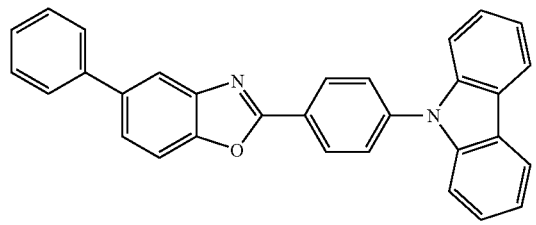
(127) 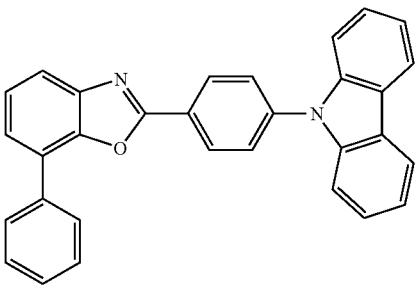
(128) 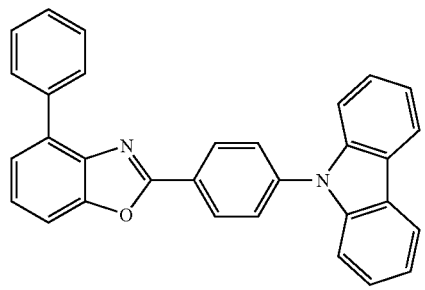
(129) 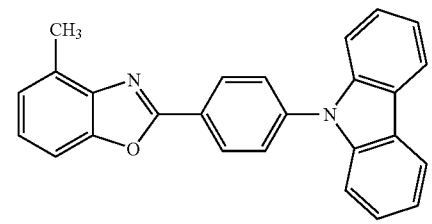
(130) 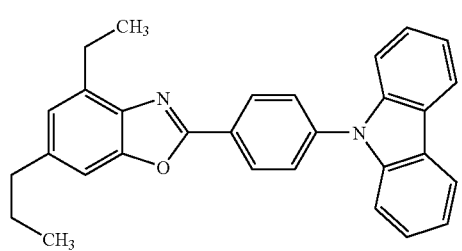
(131) 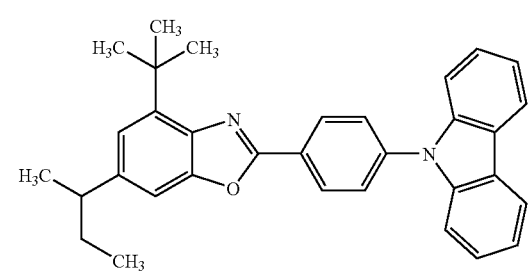
(132) 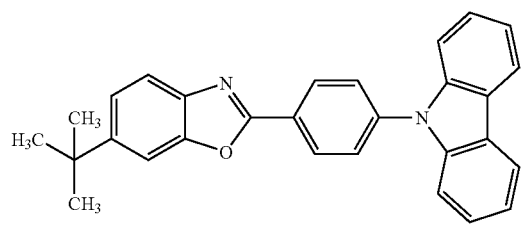
(133) 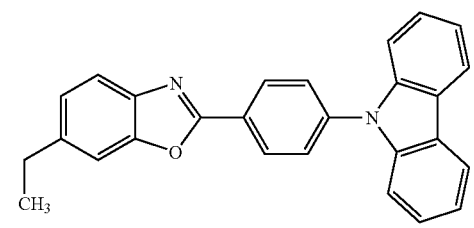
(134) 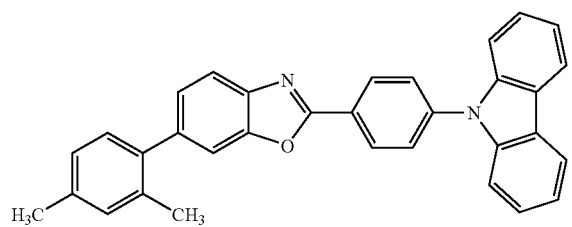
(135) 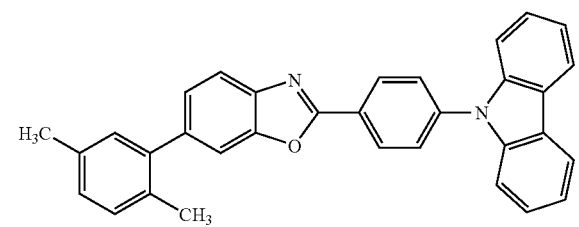
(138) 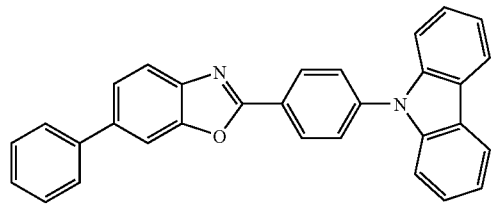
(139) 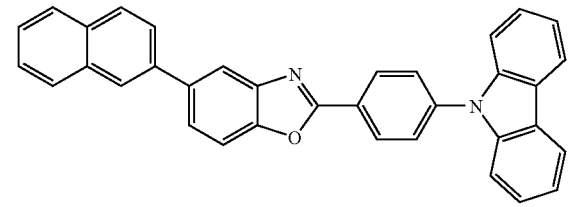

-continued
(140)
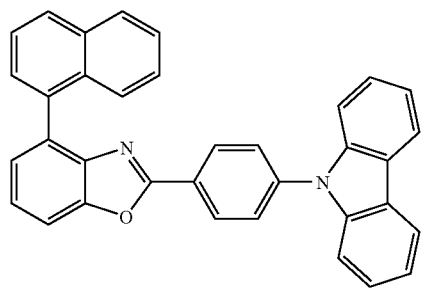
(141)
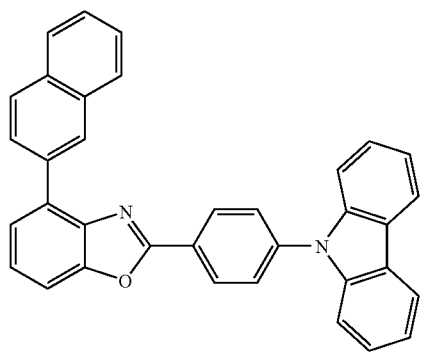
(142)
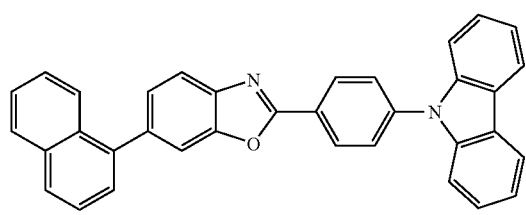
(143)
(144)
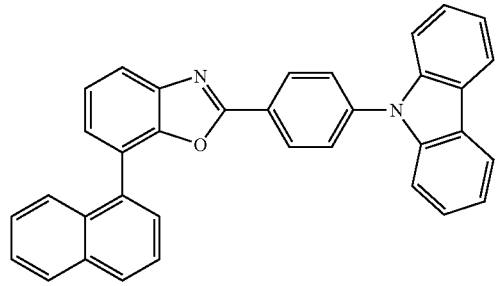
(145)
(146)
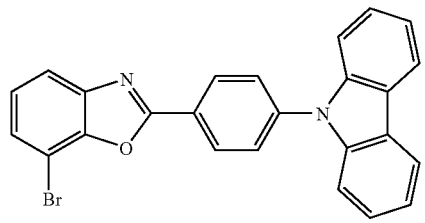
(147)
(148)
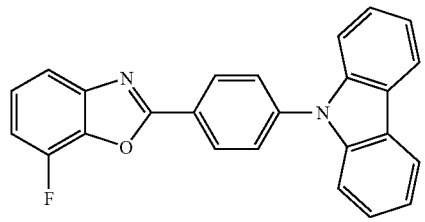
(149)
(150)
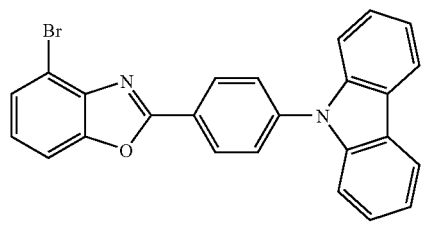
(151)
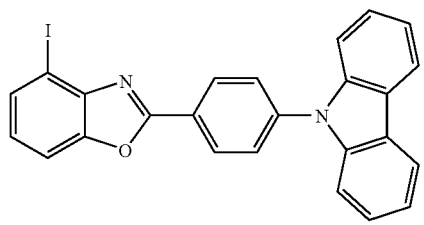

-continued
(152)
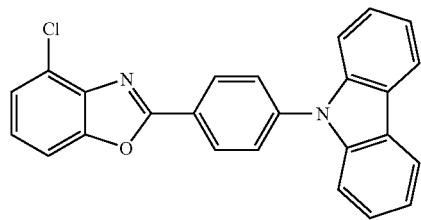
(153)
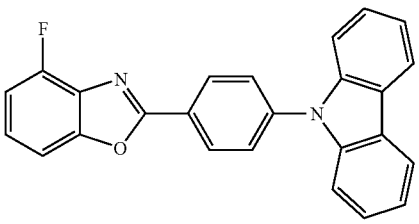
(154)
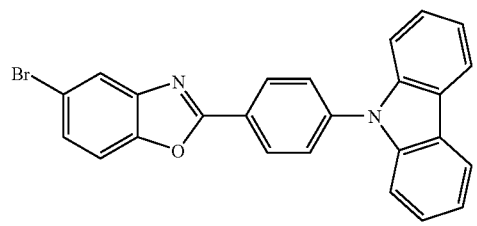
(155)
(156)
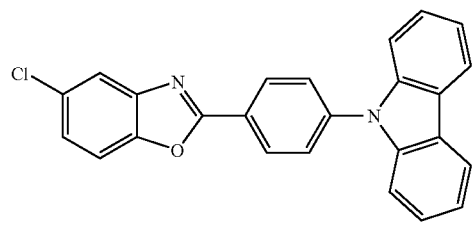
(157)
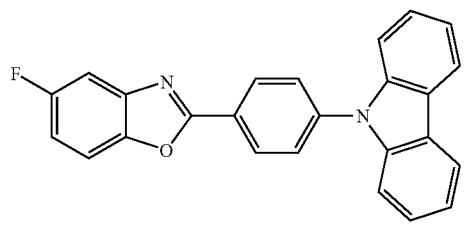
(158)
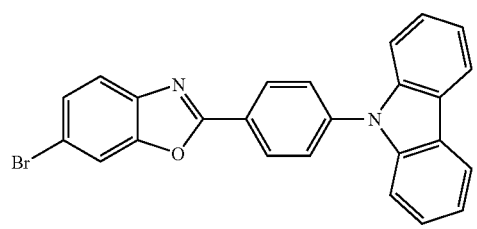
(159)
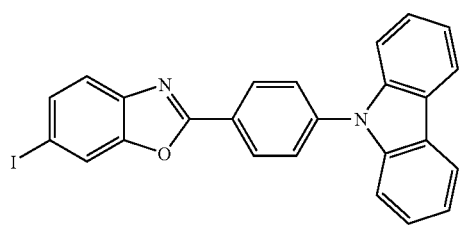
(160)
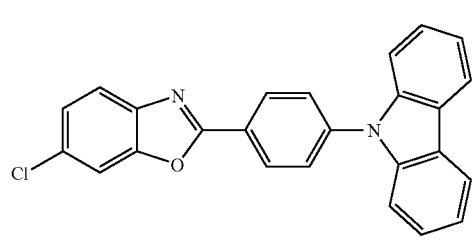
(161)
(162)
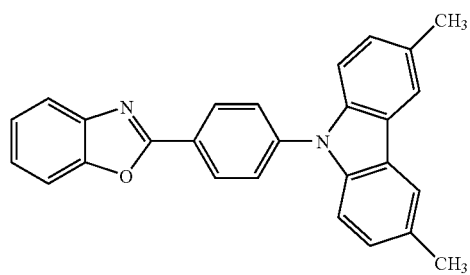
(163)
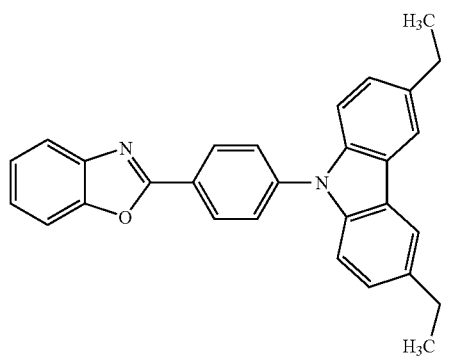

-continued
(164) 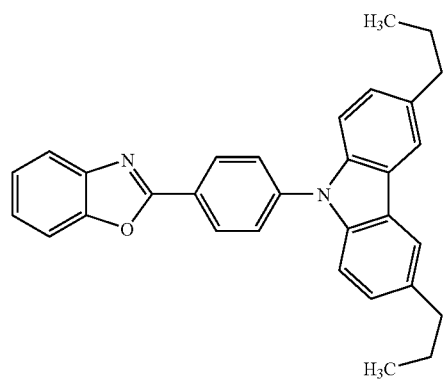
(165) 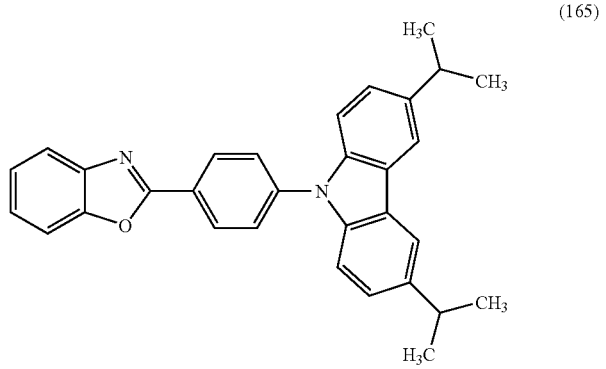
(166) 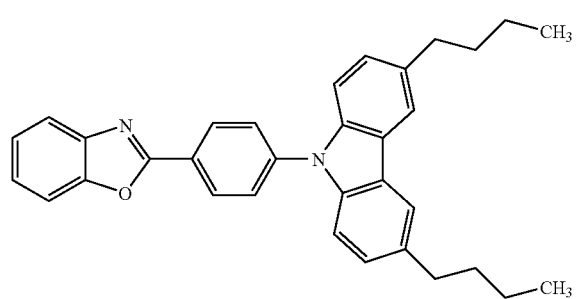
(167) 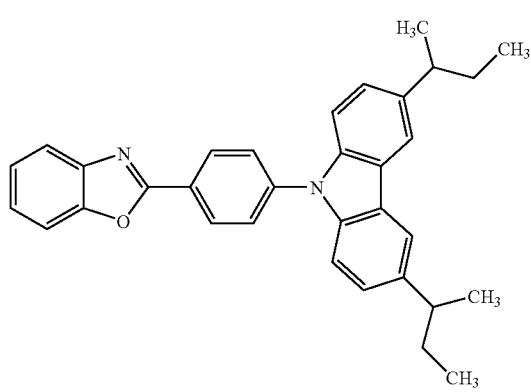
(168) 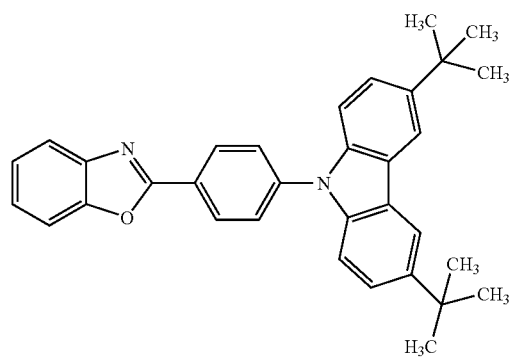
(169) 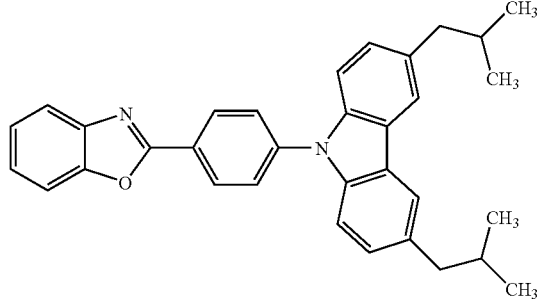
(170) 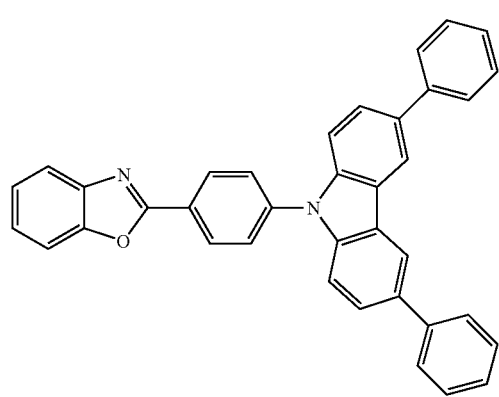
(171) 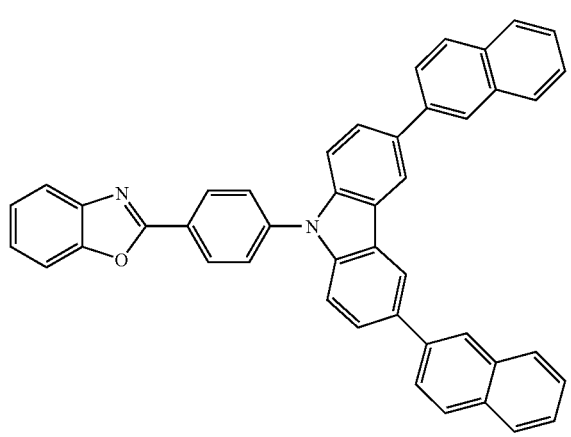

-continued
(172)
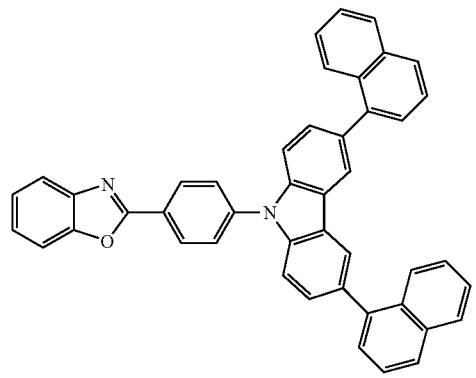
(173)
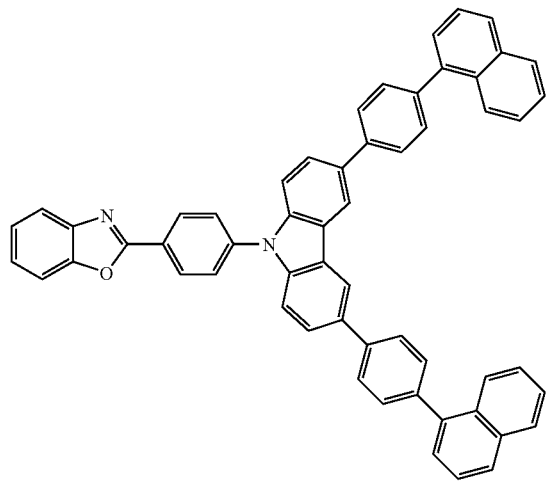
(174)
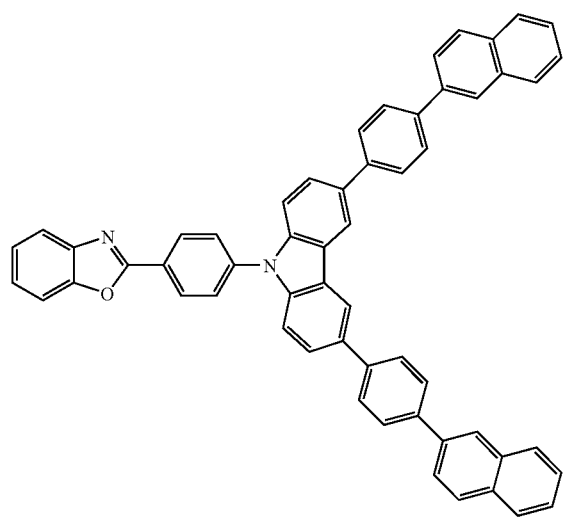
(175)
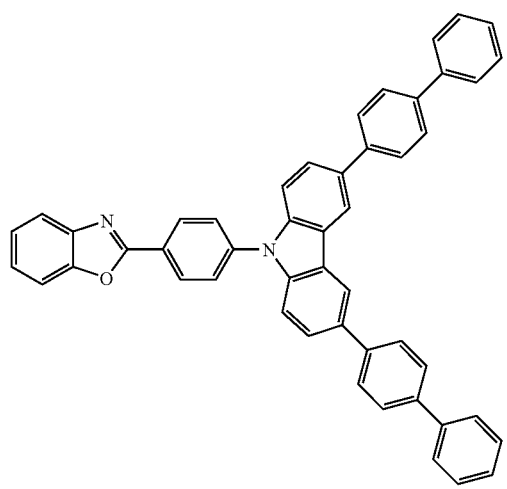
(176)
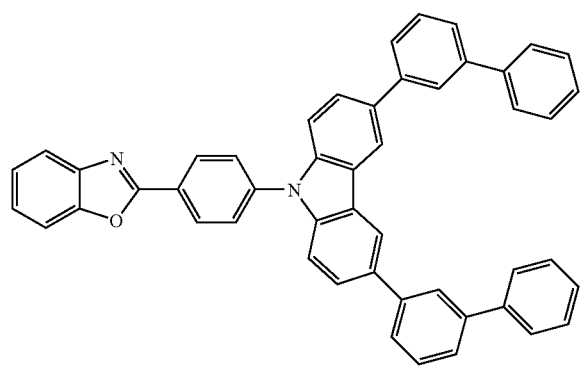
(177)
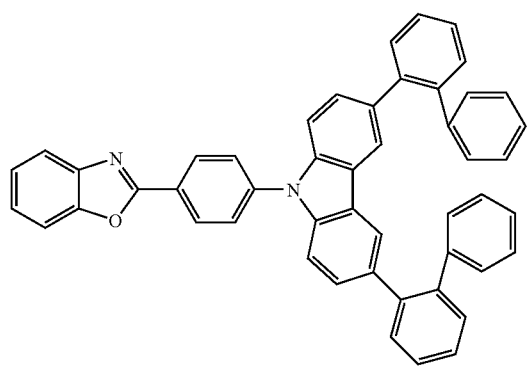

-continued
(178)
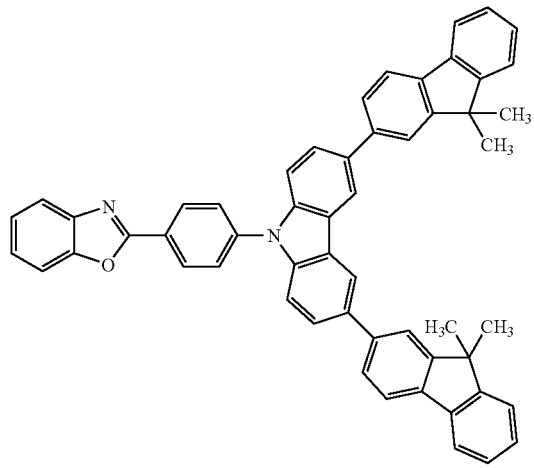
(179)
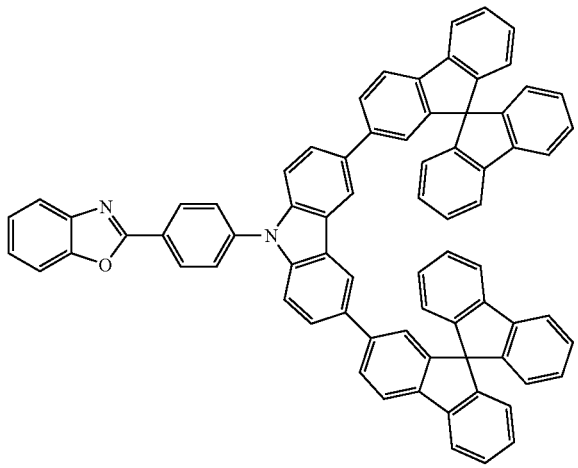
(180)
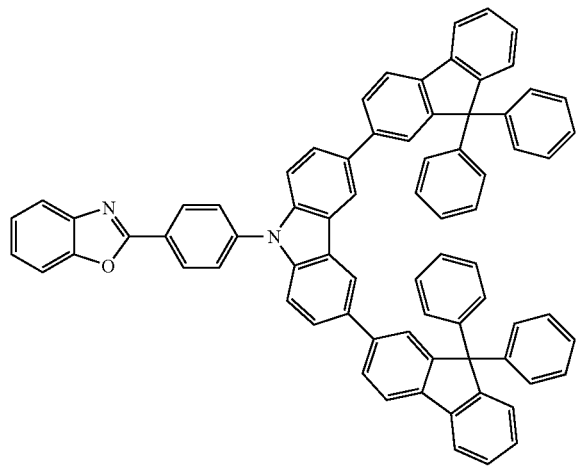
(181)
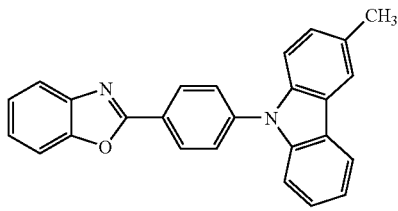
(182)
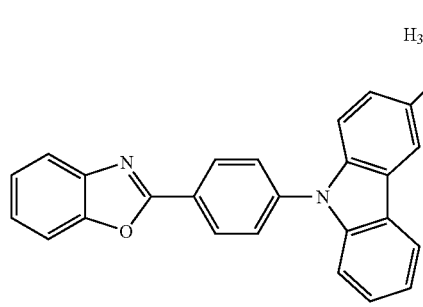
(183)
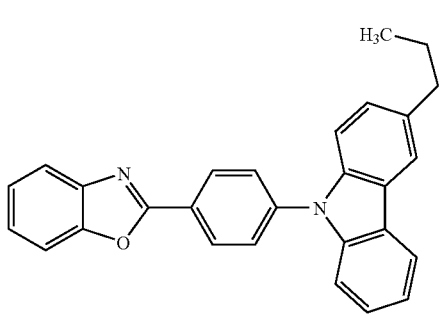
(184)
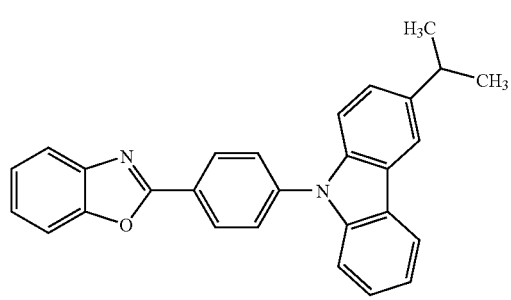
(185)
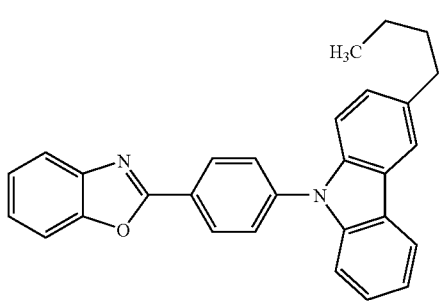

-continued
(186) 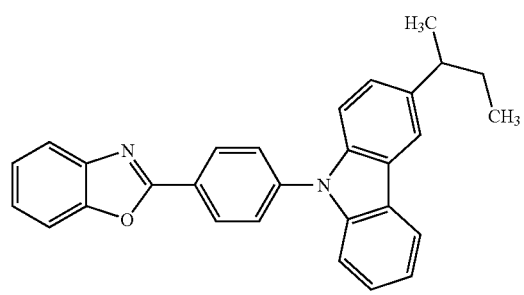
(187) 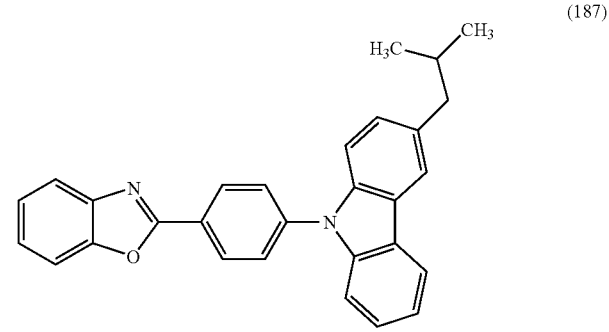
(188) 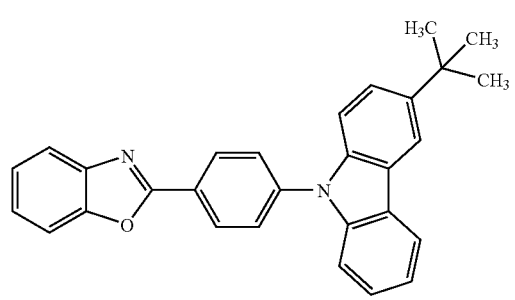
(189) 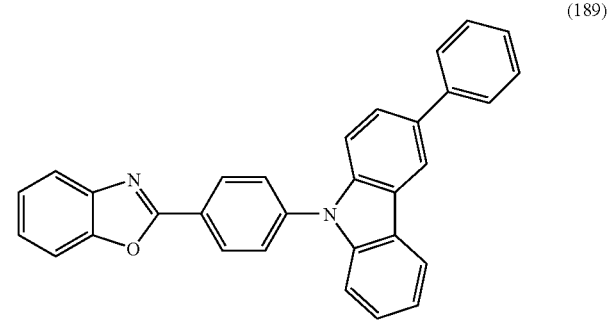
(190) 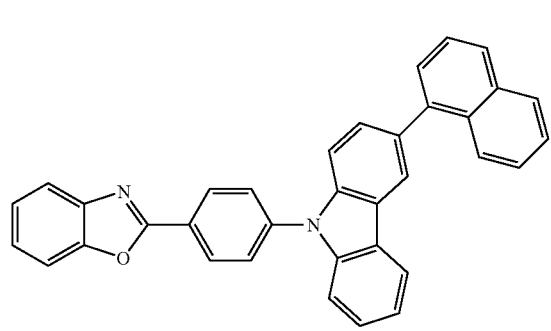
(191) 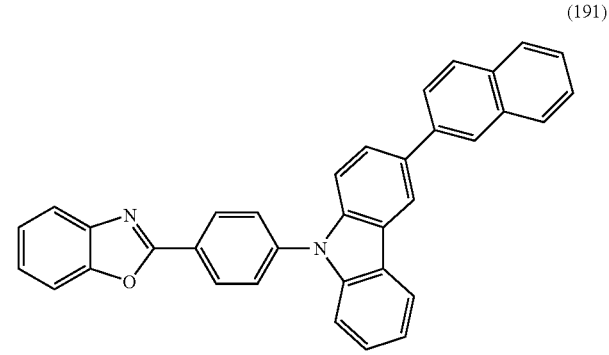
(192) 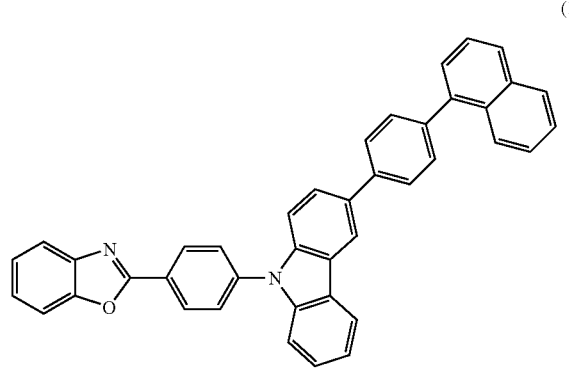
(193) 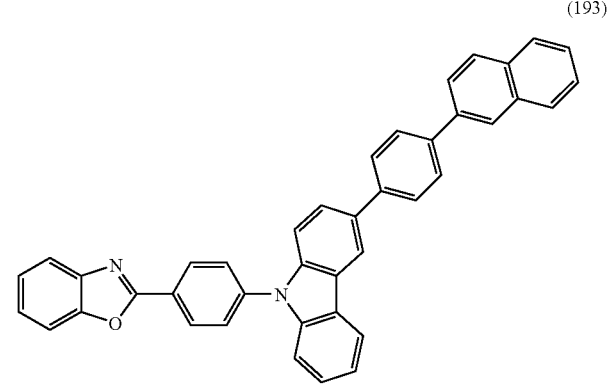

-continued
(194)
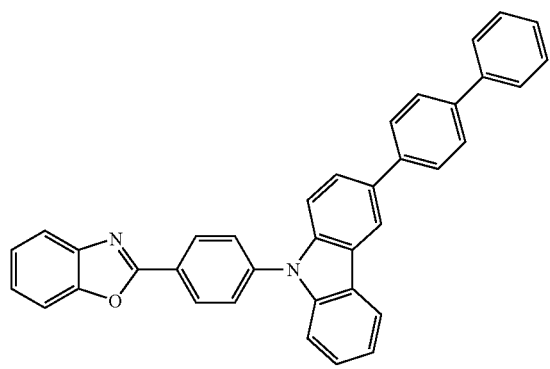
(195)
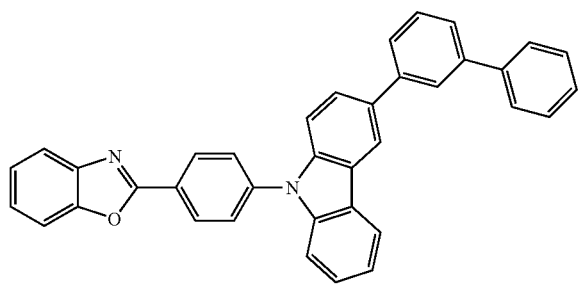
(196)
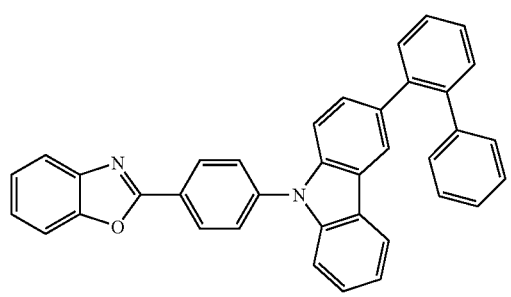
(197)
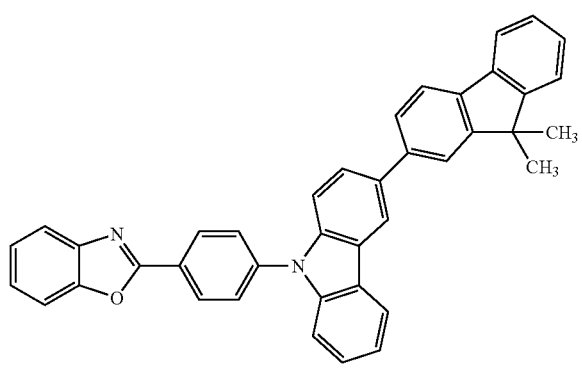
(198)
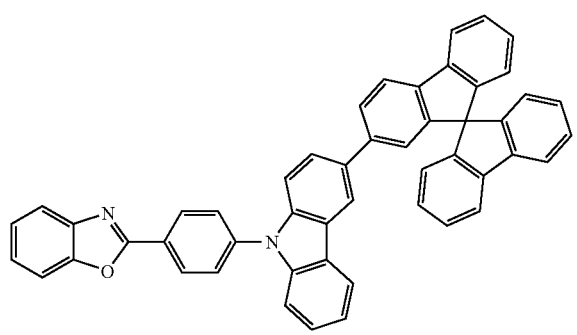
(199)
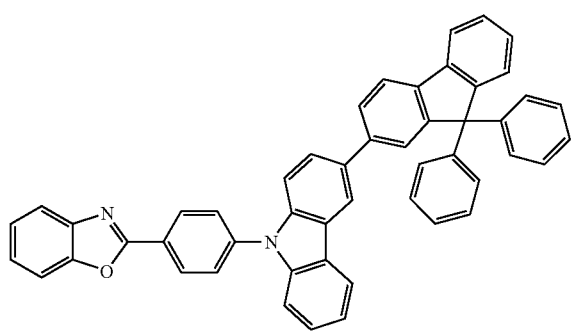
(200)
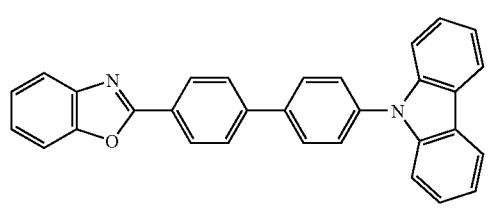
(201)
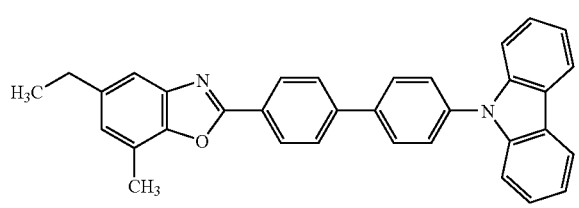
(202)
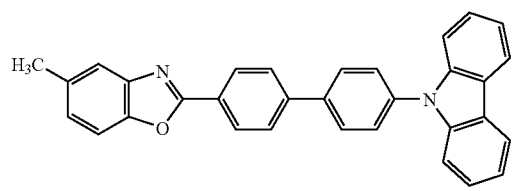
(203)
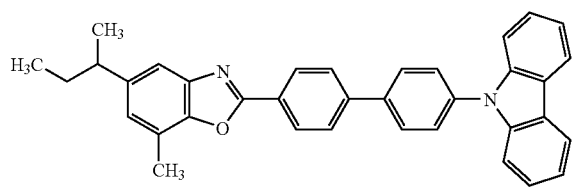

-continued
(204)
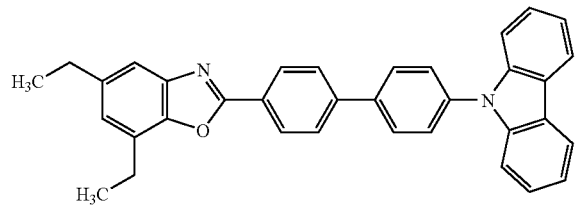
(205)
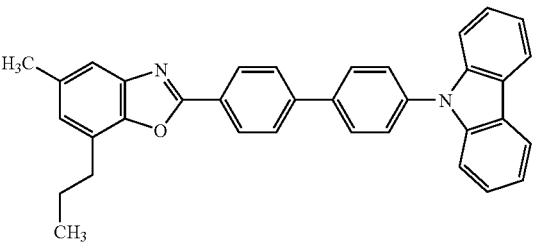
(206)
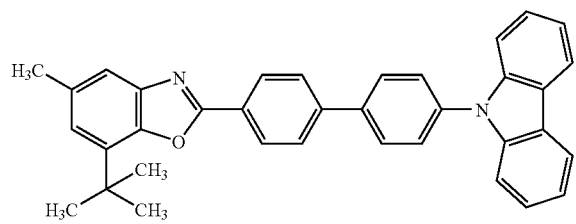
(207)
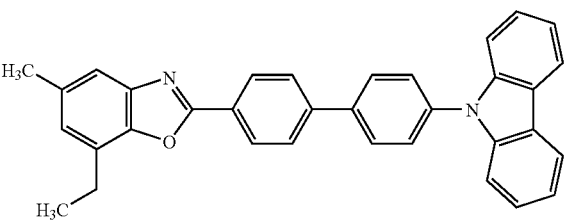
(208)
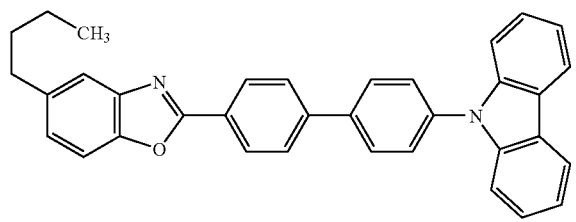
(209)
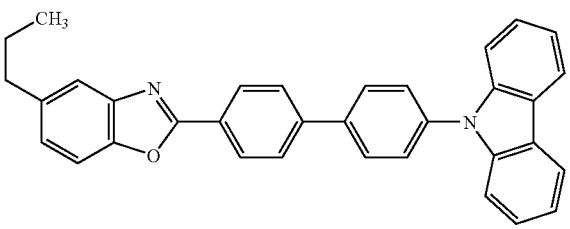
(210)
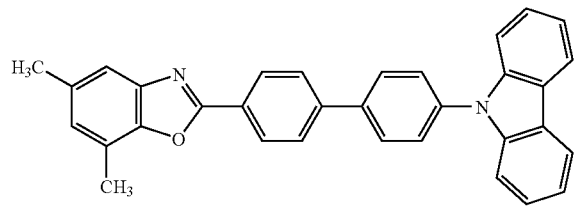
(211)
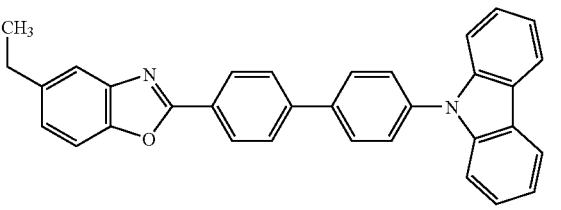
(212)
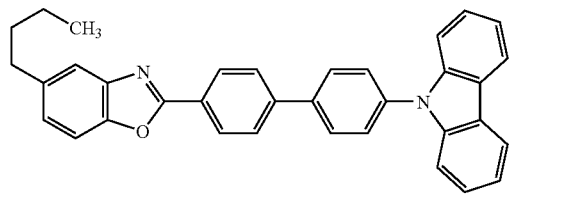
(213)
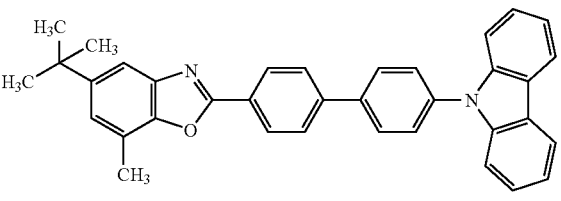
(214)
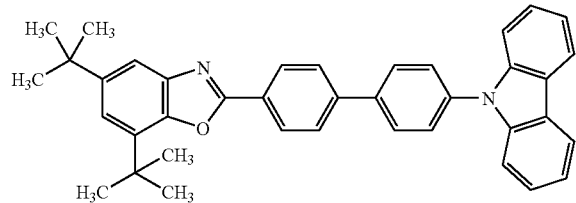
(215)
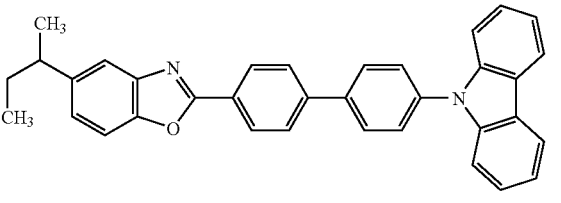

-continued
(216)
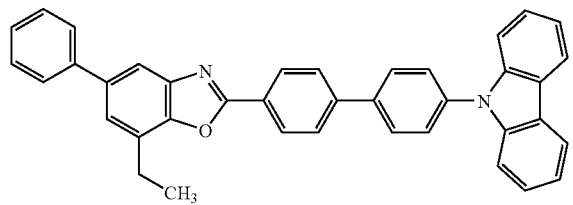
(217)
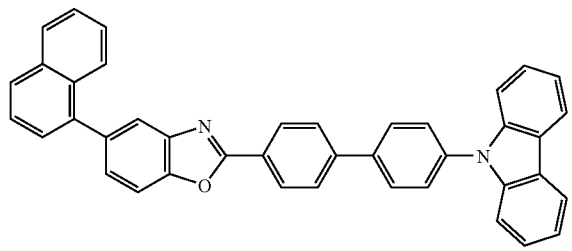
(218)
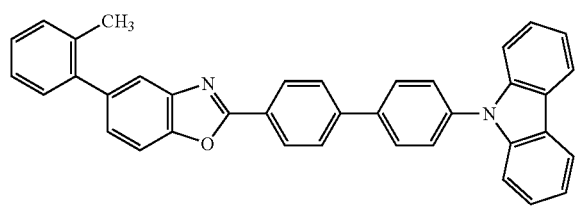
(219)
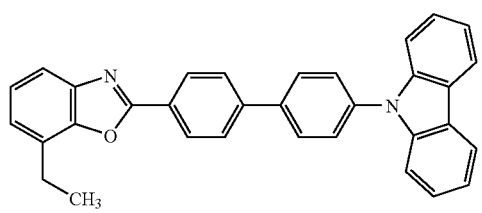
(220)
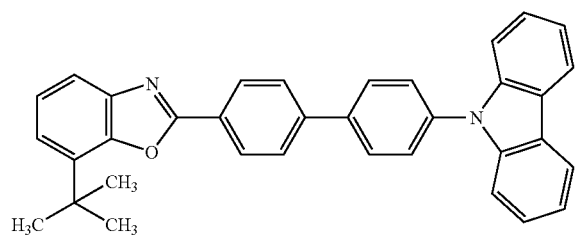
(221)
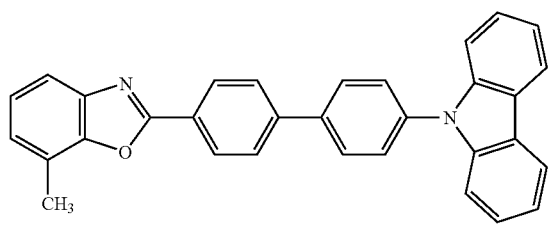
(222)
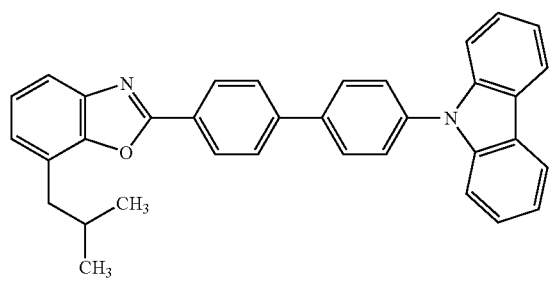
(223)
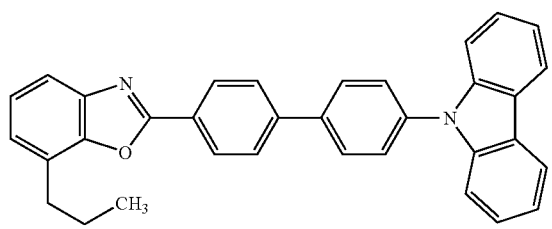
(224)
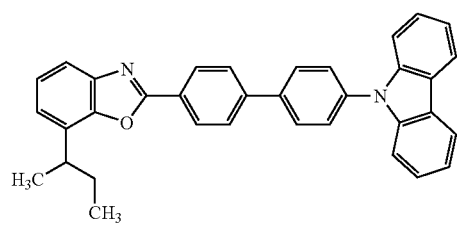
(225)
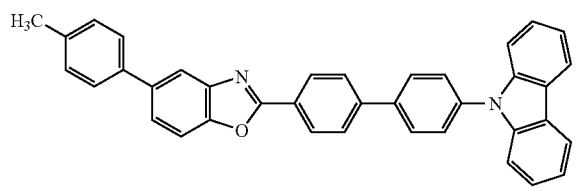
(226)
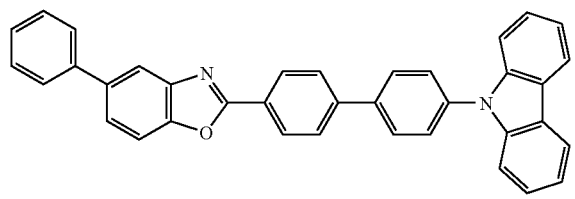
(227)
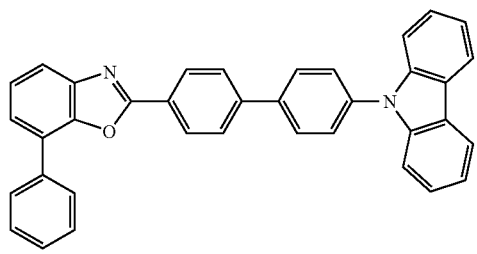

(228) 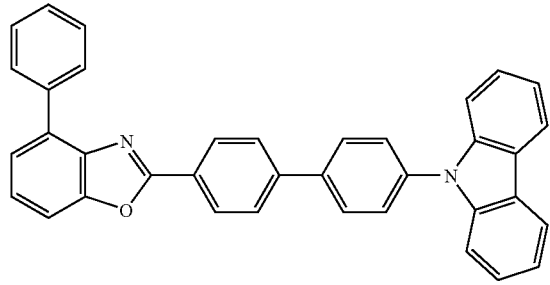
(229) 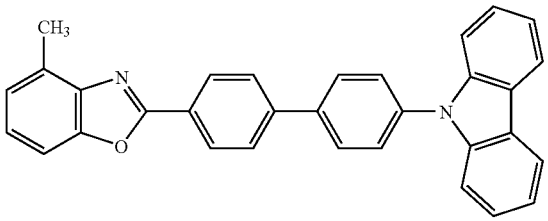
(230) 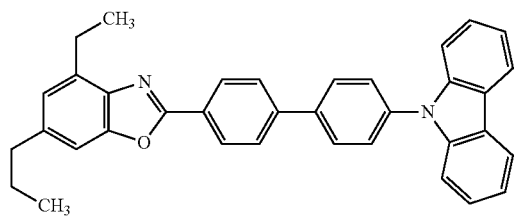
(231) 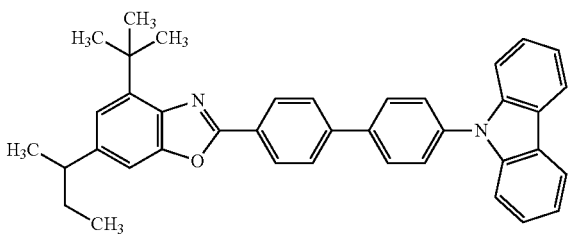
(232) 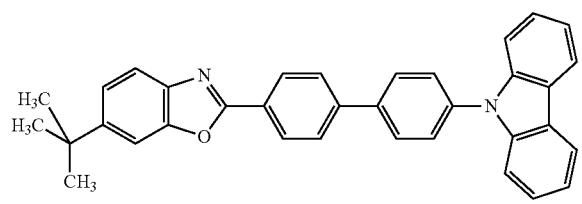
(233) 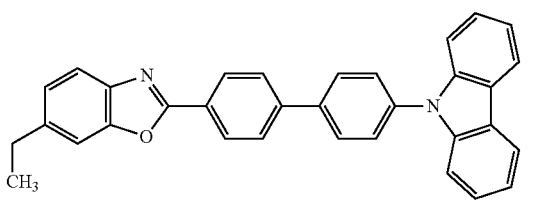
(234) 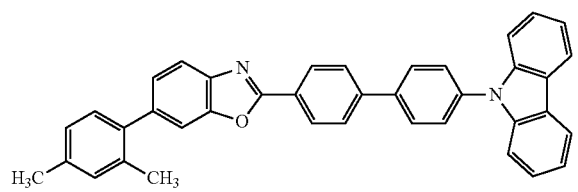
(235) 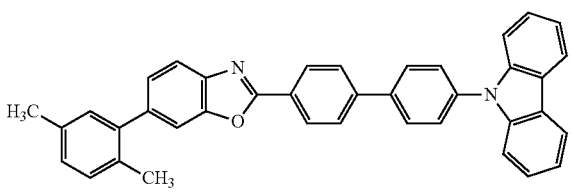
(236) 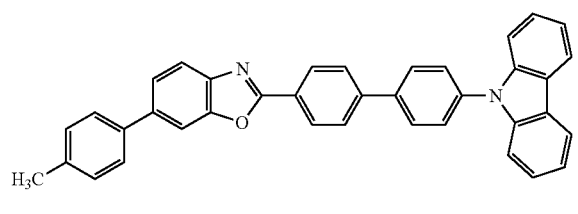
(237) 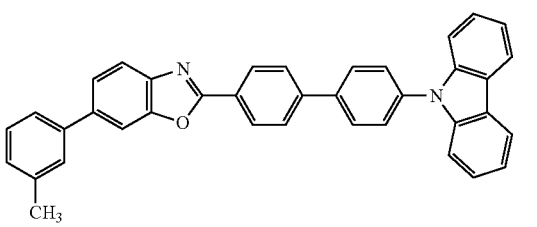
(238) 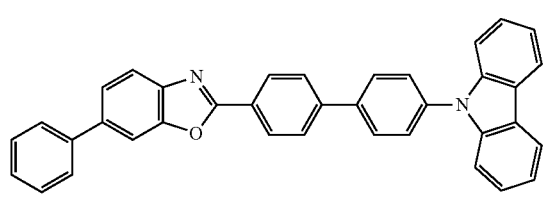
(239) 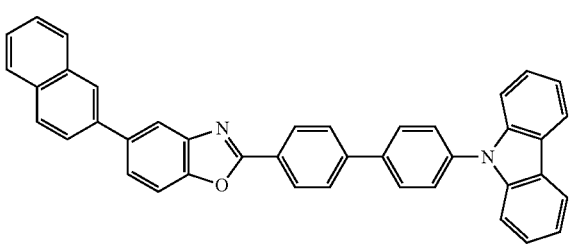

-continued
(240)
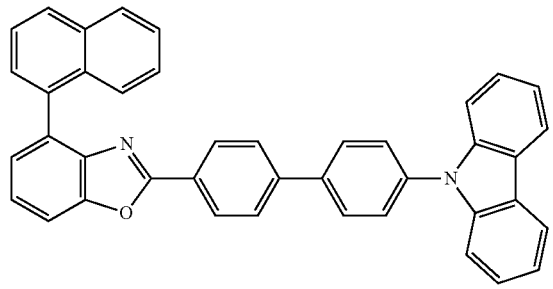
(241)
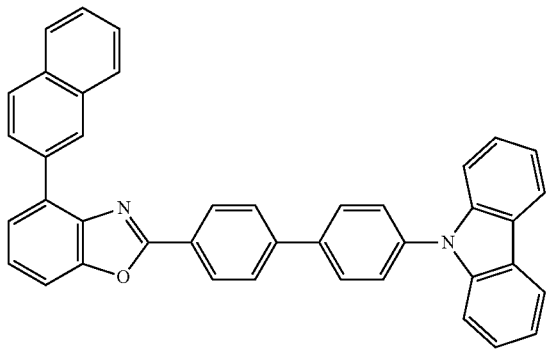
(242)
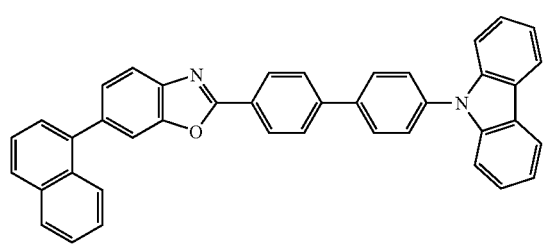
(243)
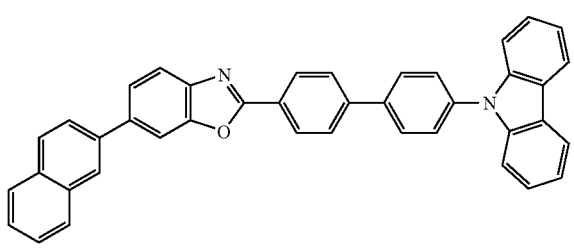
(244)
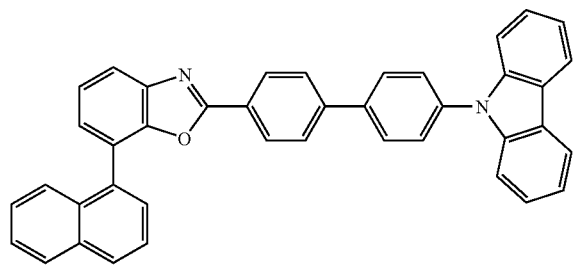
(245)
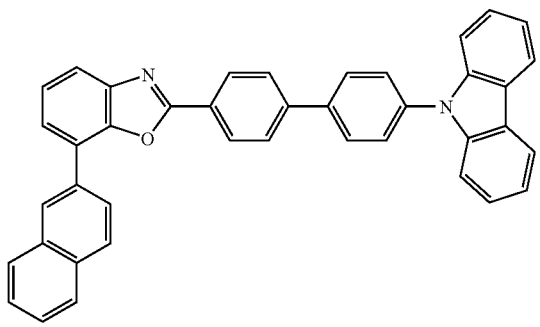
(246)
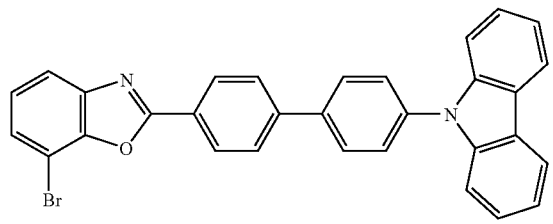
(247)
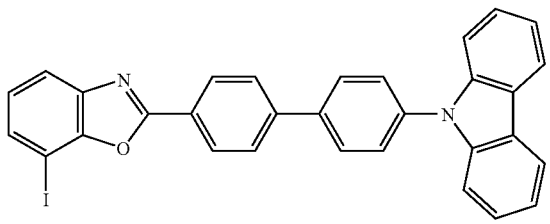
(248)
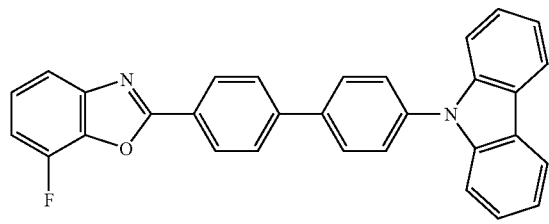
(249)
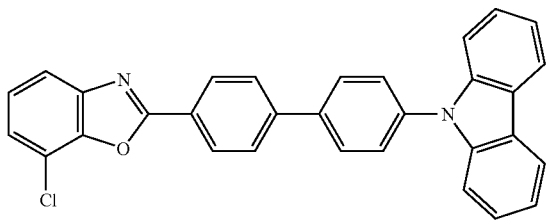

-continued
(250)
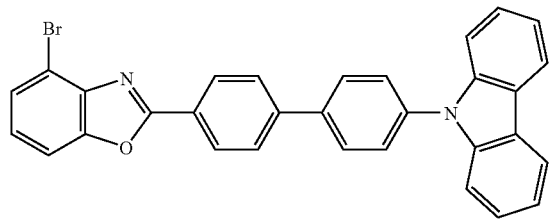
(251)
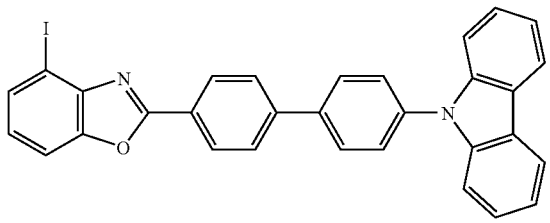
(252)
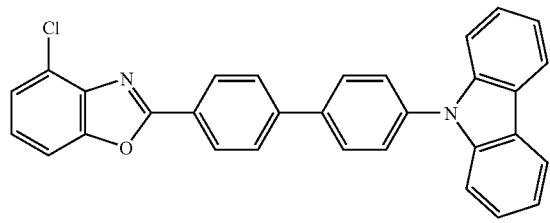
(253)
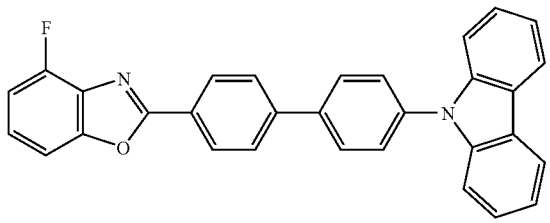
(254)
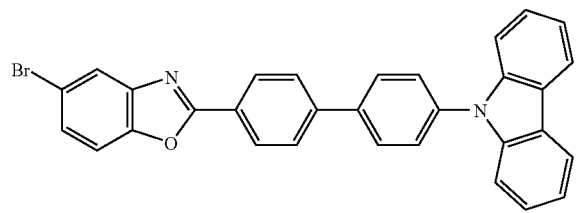
(255)
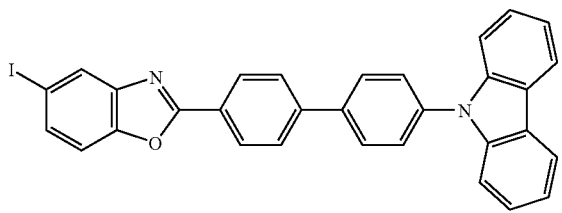
(256)
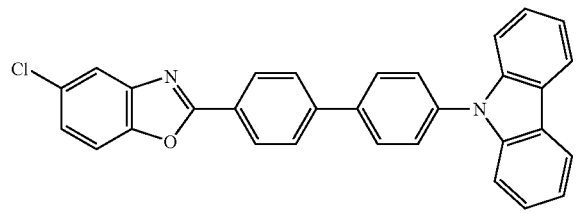
(257)
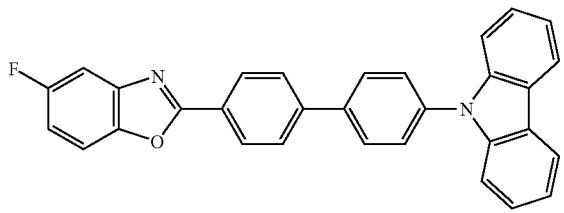
(258)
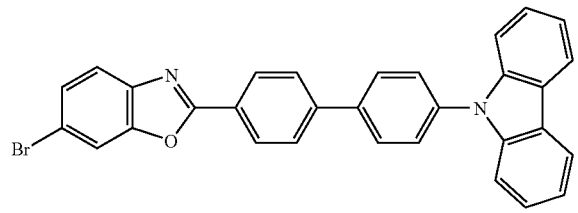
(259)
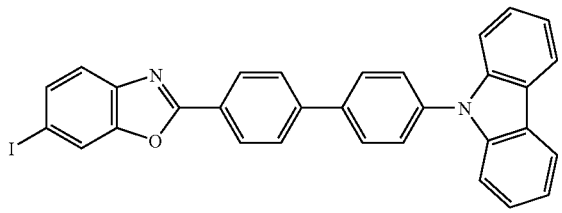
(260)
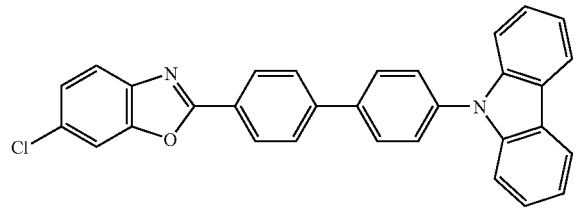
(261)
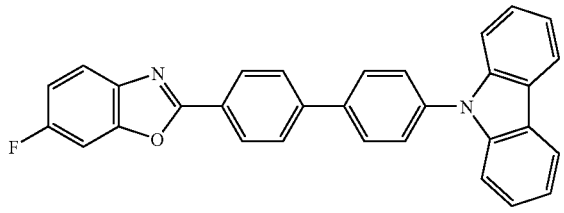

-continued
(262)
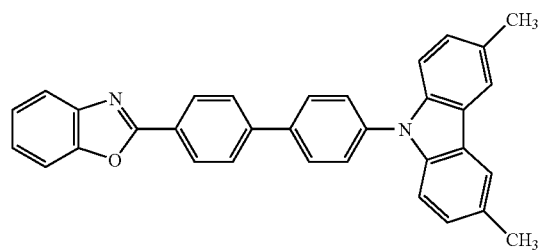
(263)
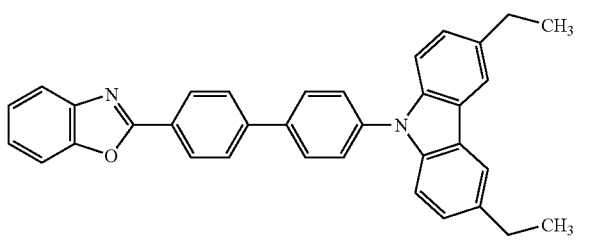
(264)
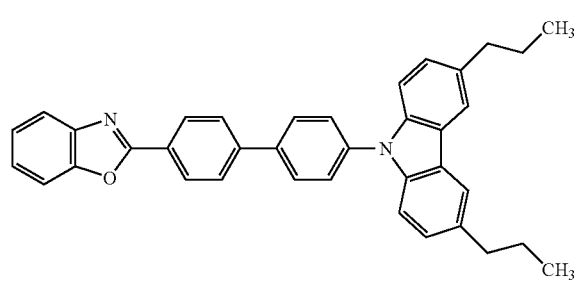
(265)
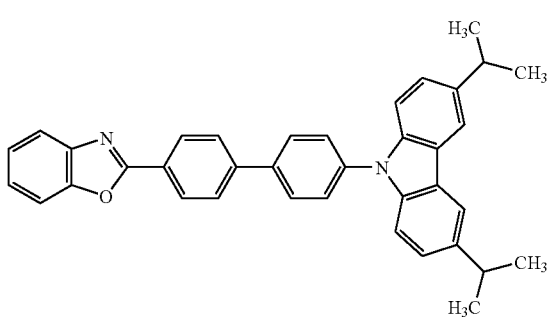
(266)
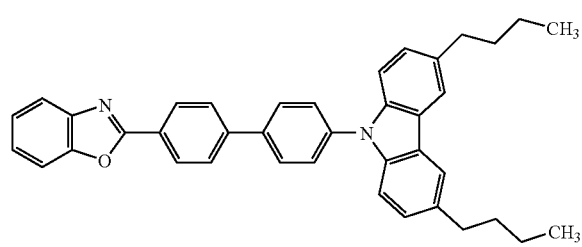
(267)
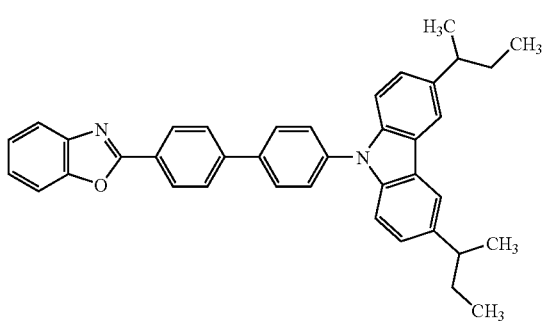
(268)
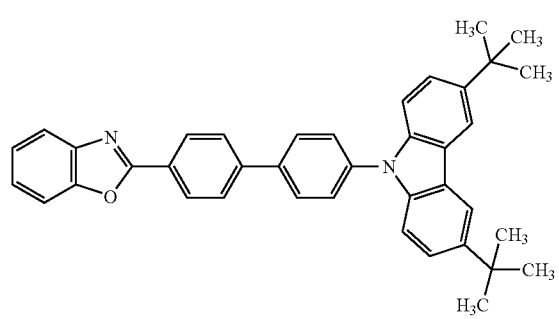
(269)
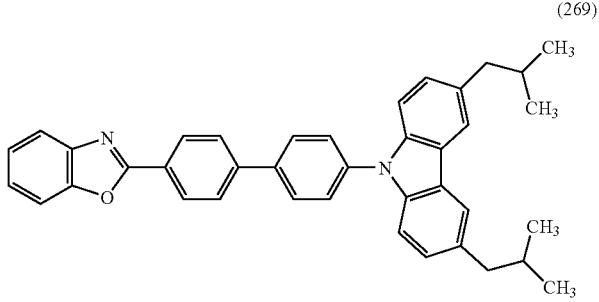

-continued
(270)
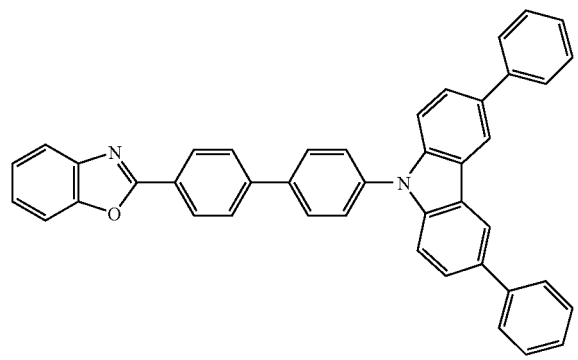
(271)
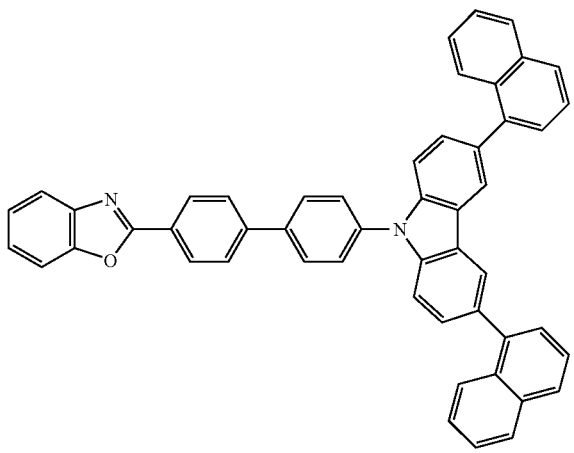
(272)
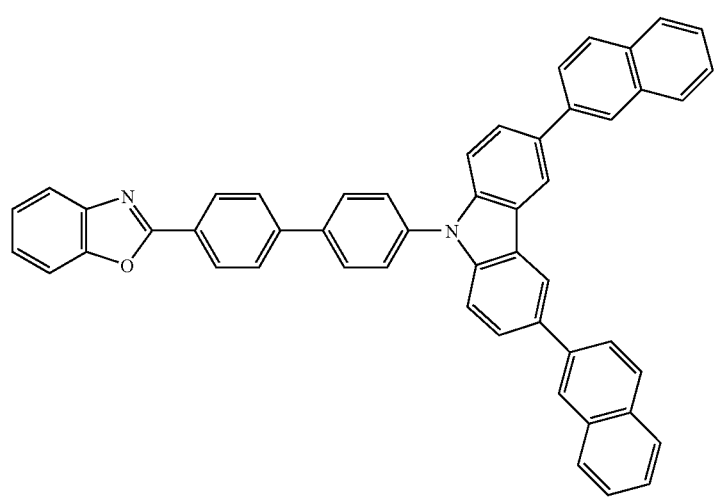
(273)
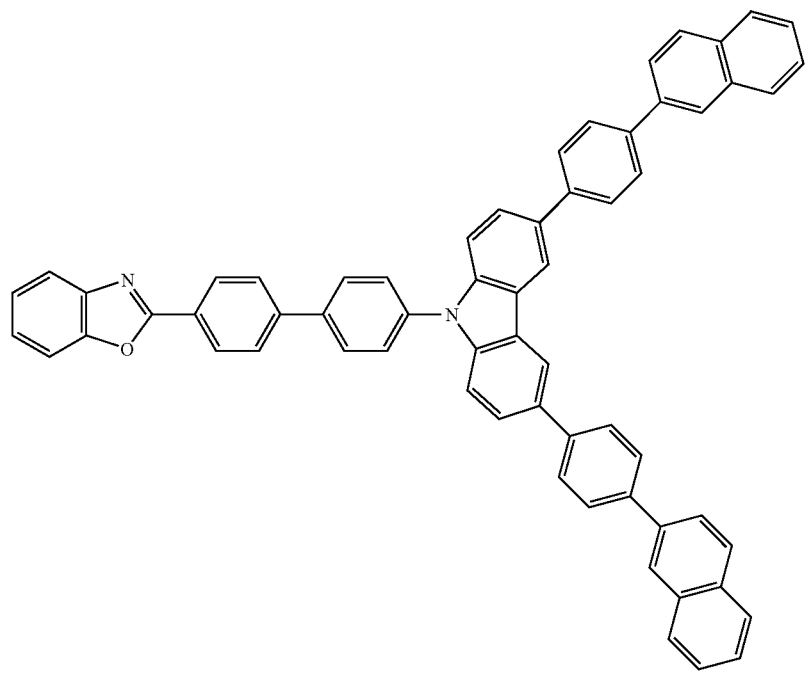

-continued
(274)
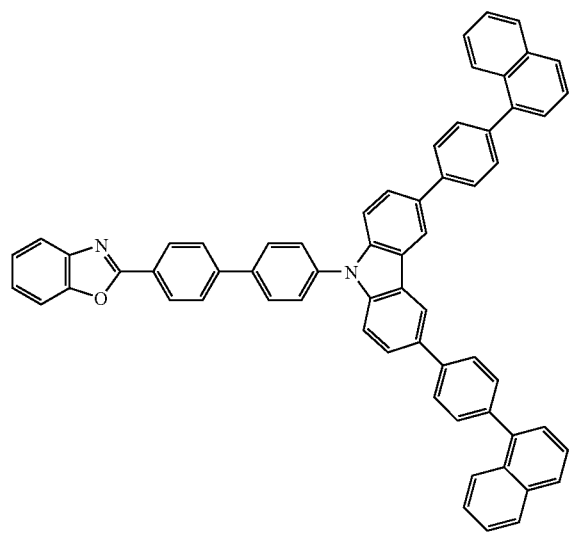
(275)
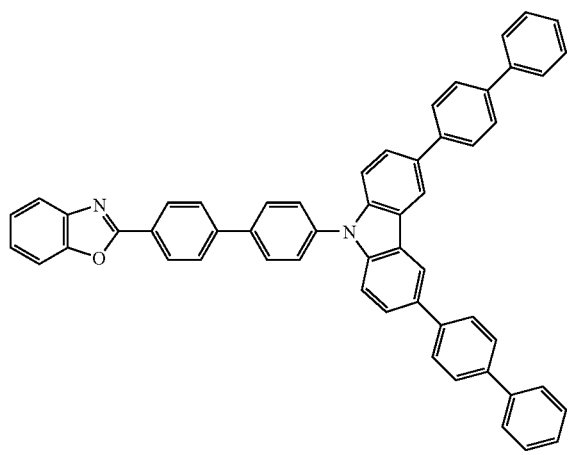
(276)
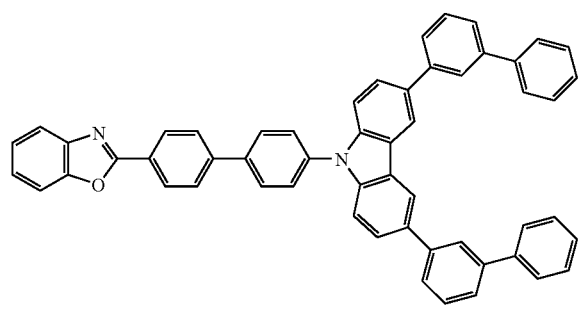
(277)
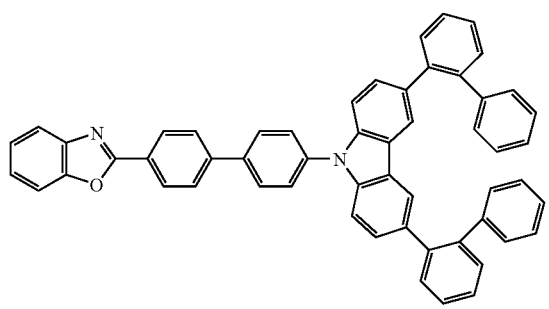
(278)
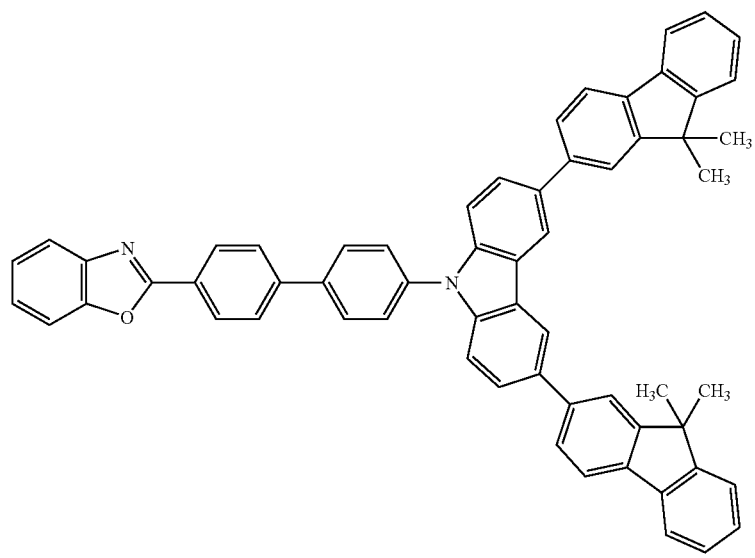

-continued
(279)
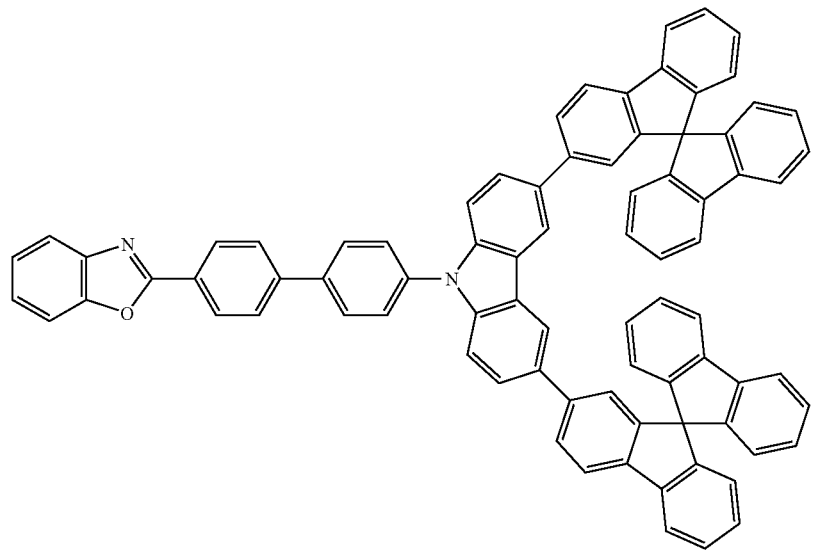
(280)
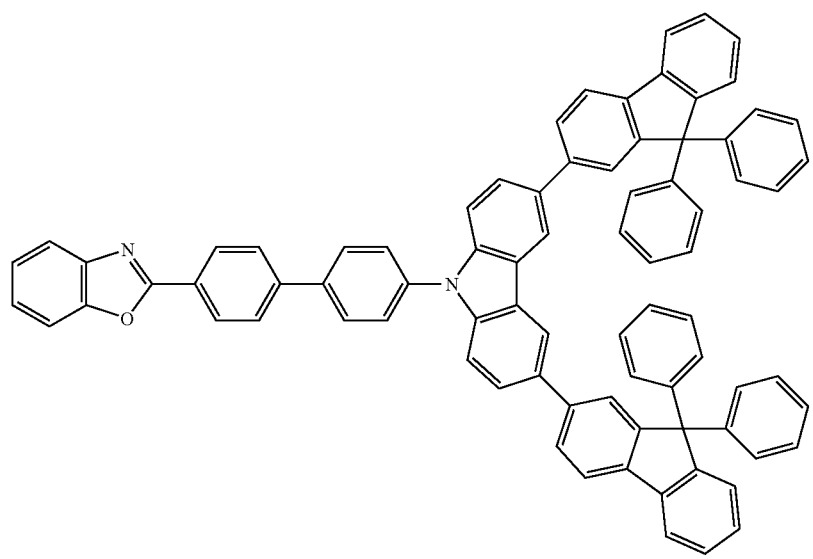
(281)
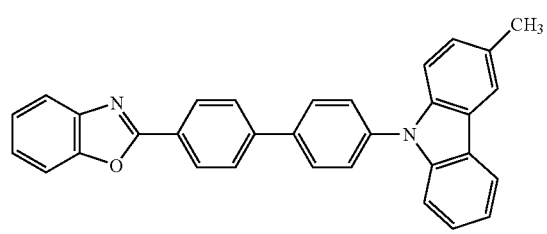
(282)
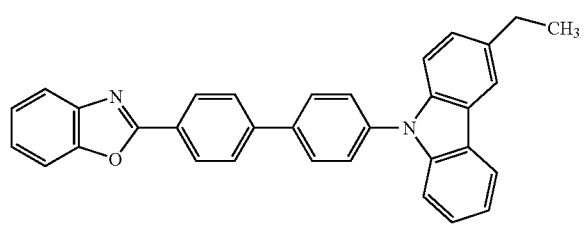
(283)
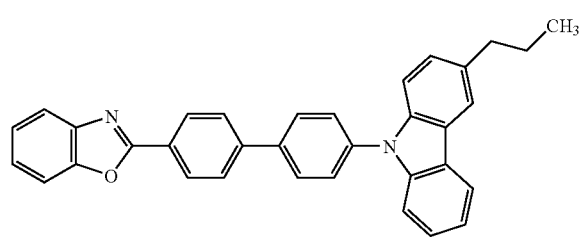
(284)
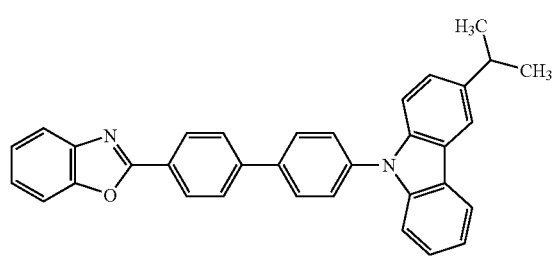

-continued
(285)
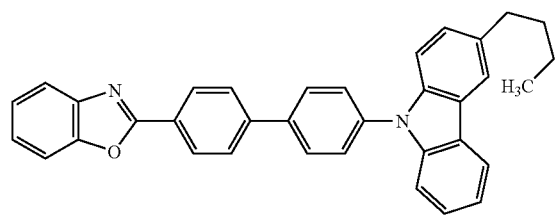
(286)
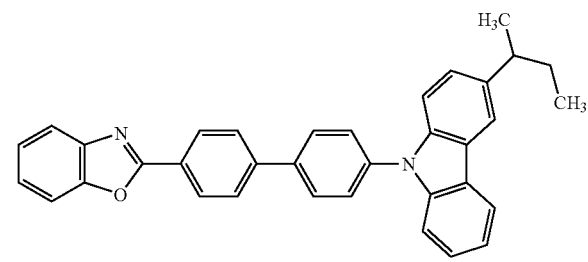
(287)
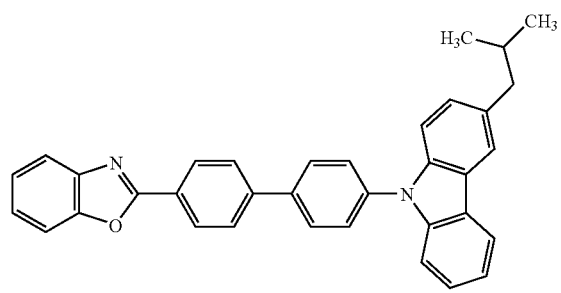
(288)
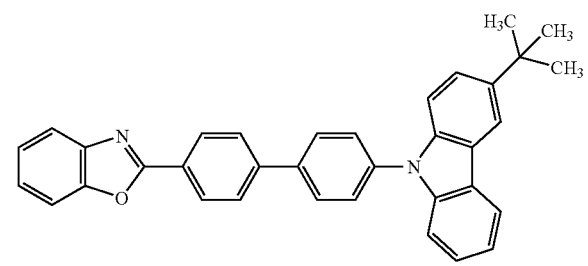
(289)
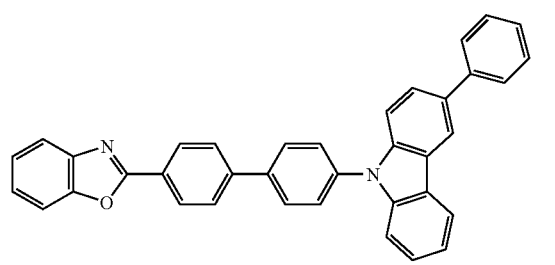
(290)
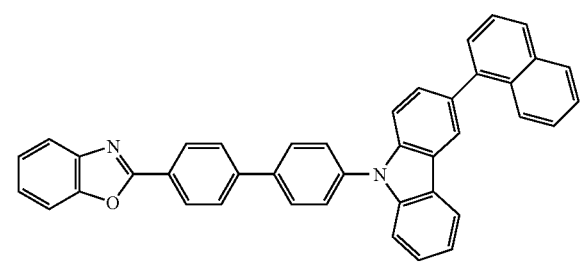
(291)
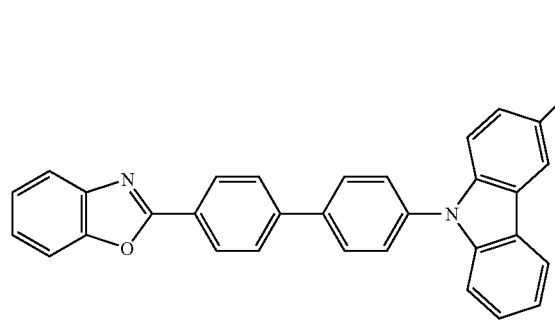
(292)
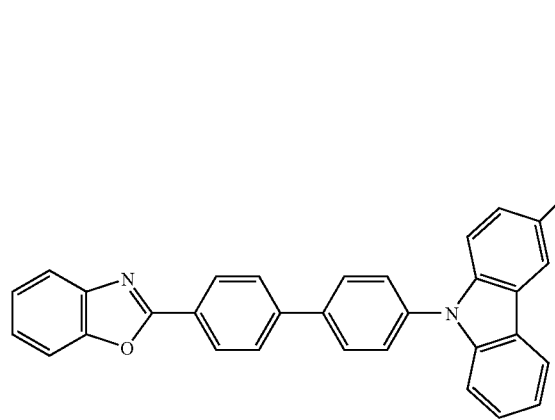

-continued
(293)
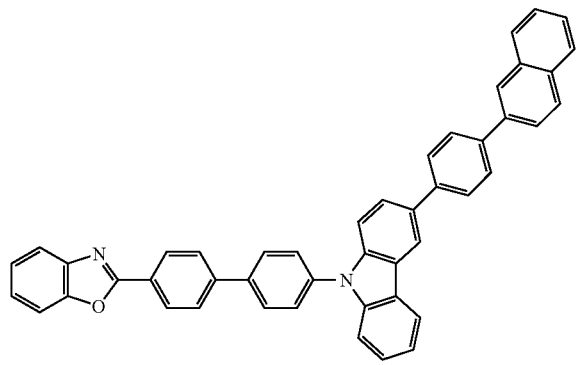
(294)
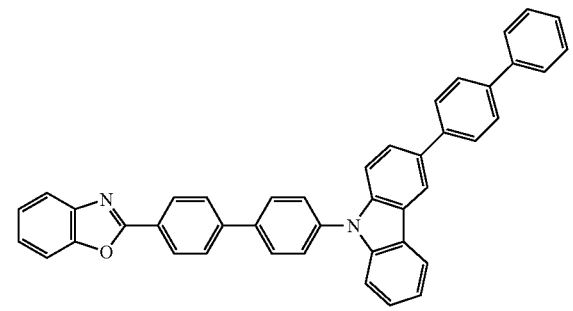
(295)
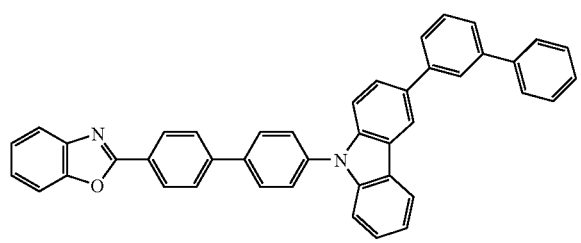
(296)
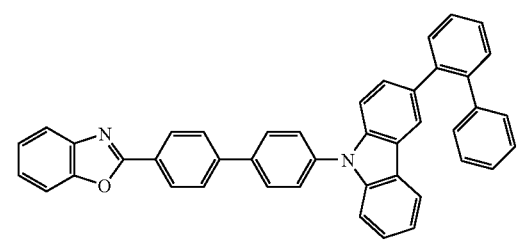
(297)
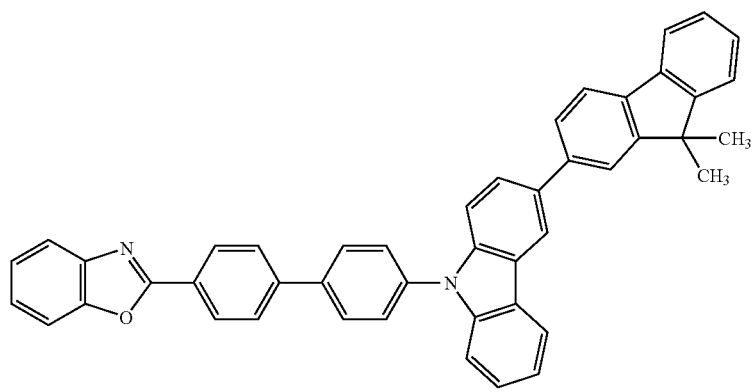
(298)
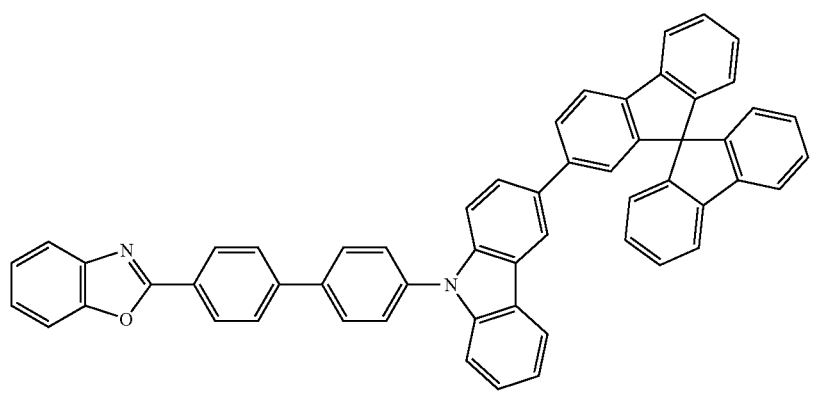

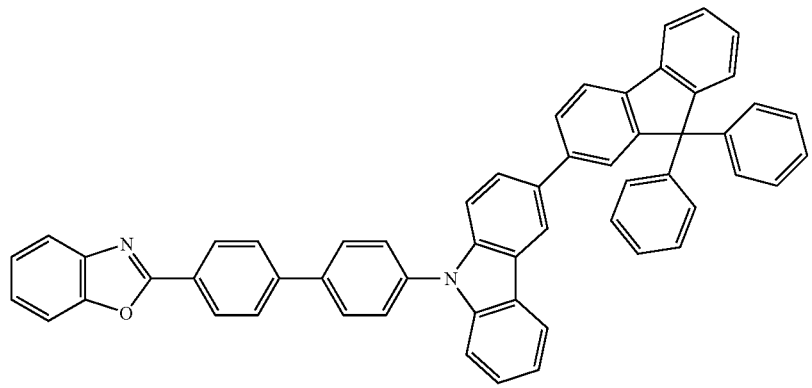
(299)
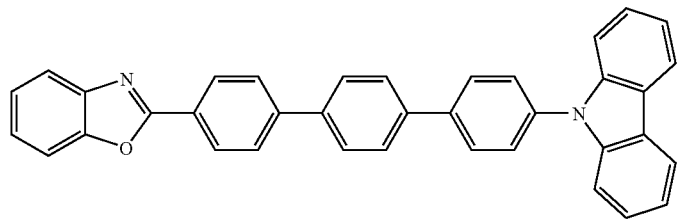
(300)
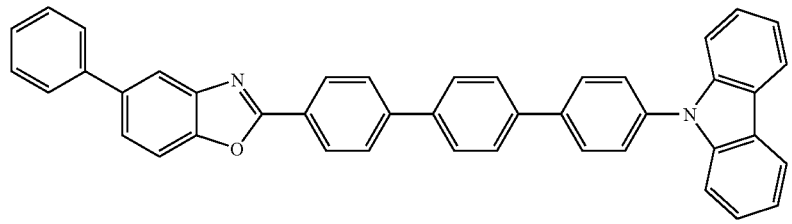
(301)
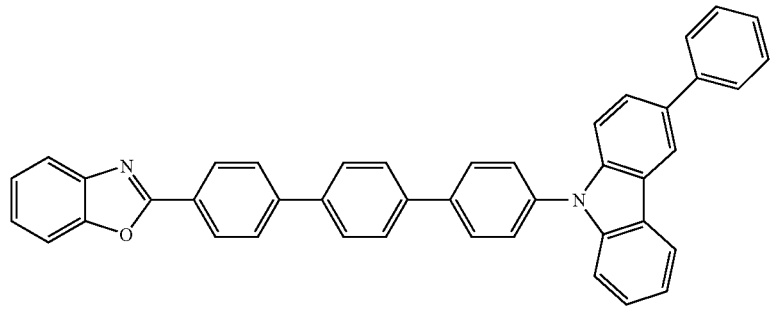
(302)
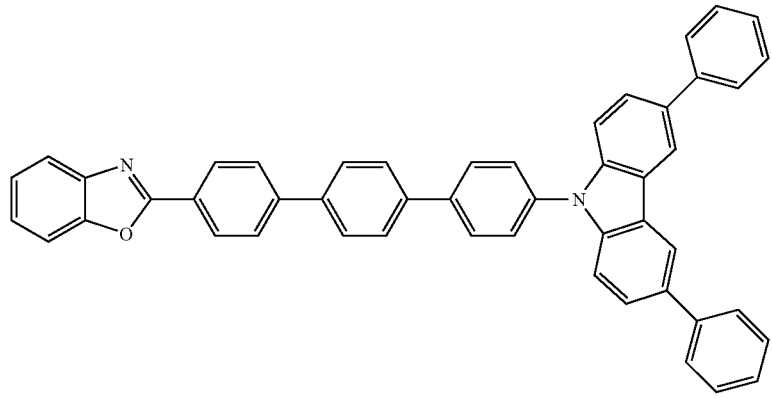
(303)

-continued
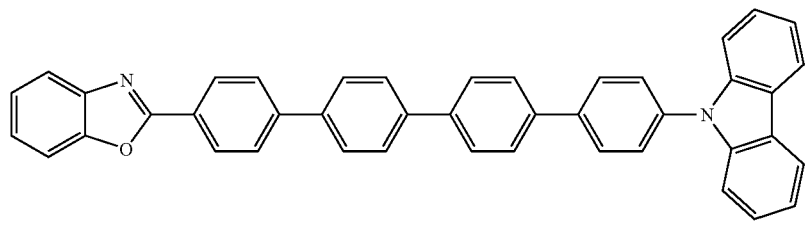
(304)
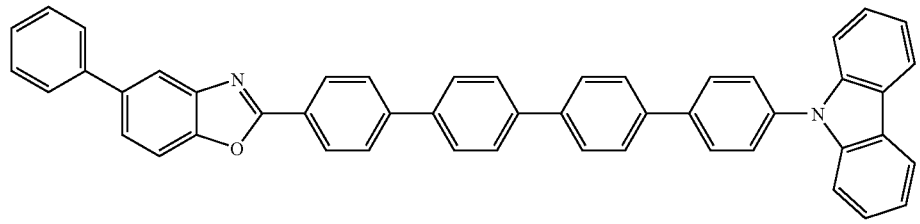
(305)
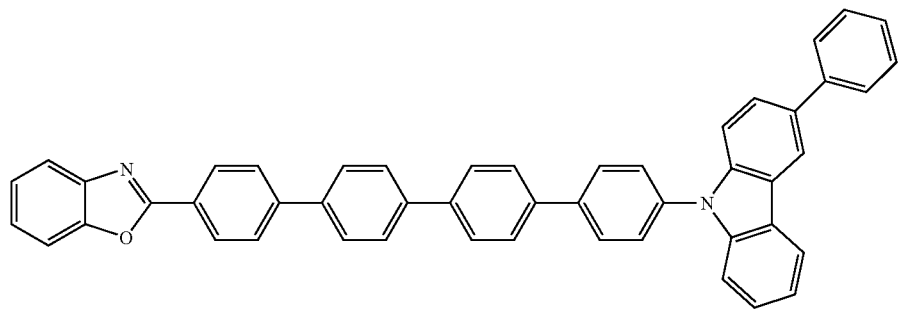
(306)
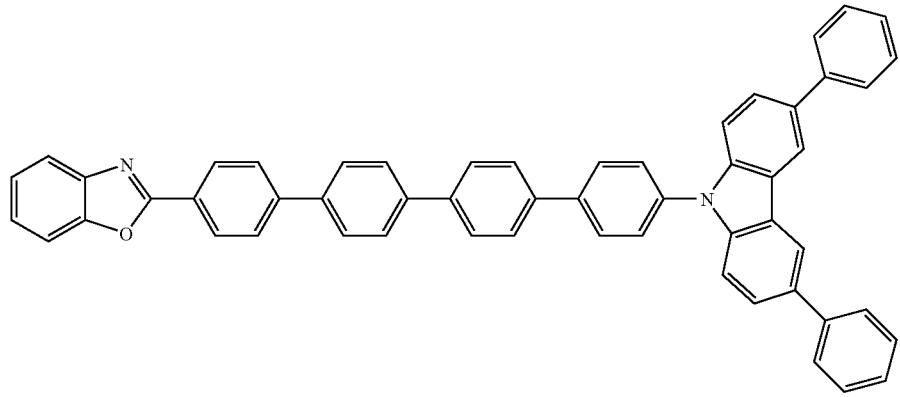
(307)
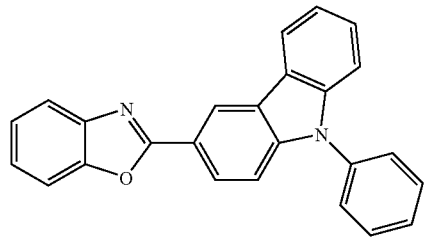
(308)
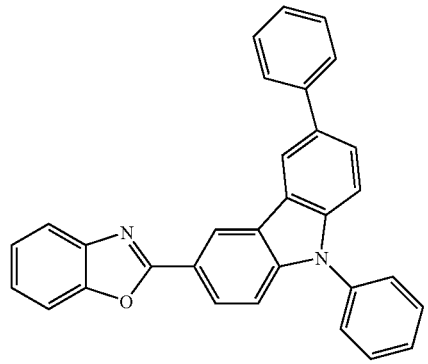
(309)

-continued
(310)
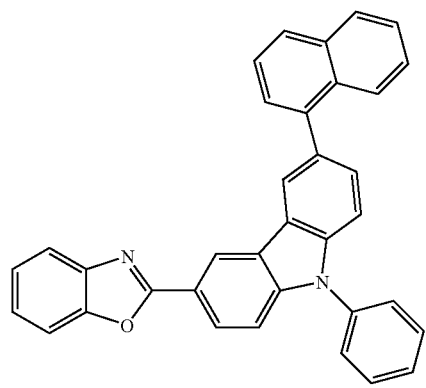
(311)
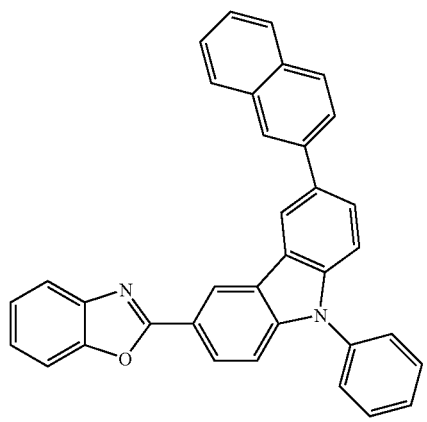
(312)
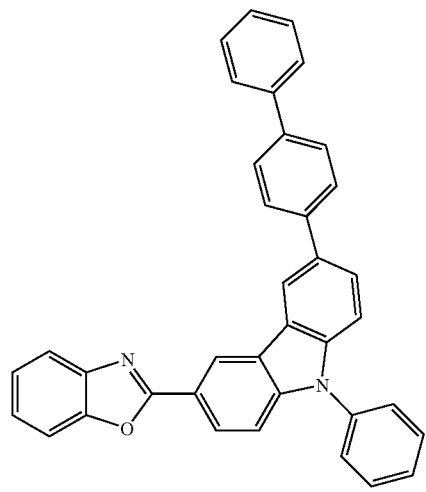
(313)
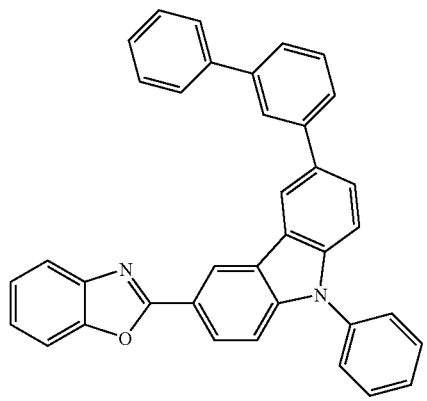
(314)
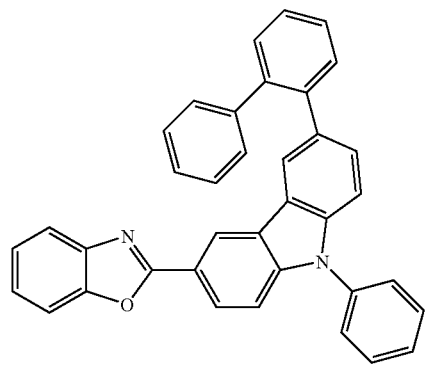
(315)
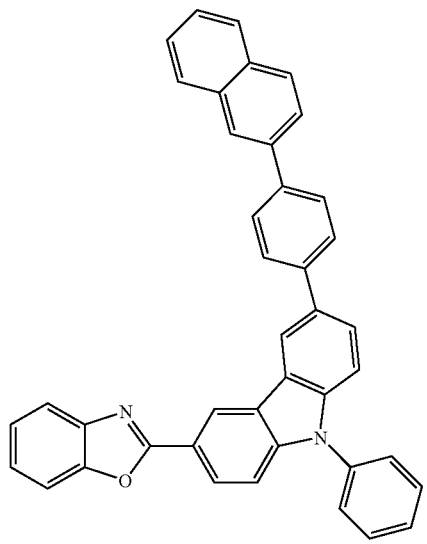

-continued
(316)
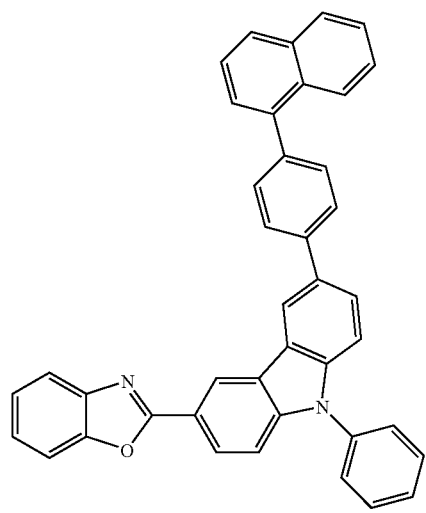
(317)
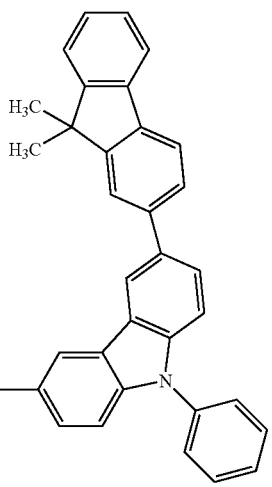
(318)
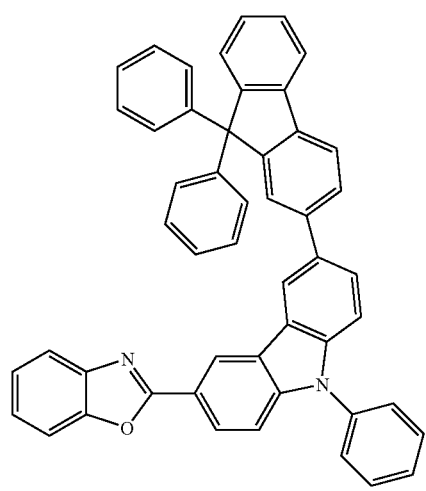
(319)
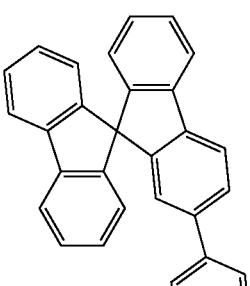
(320)
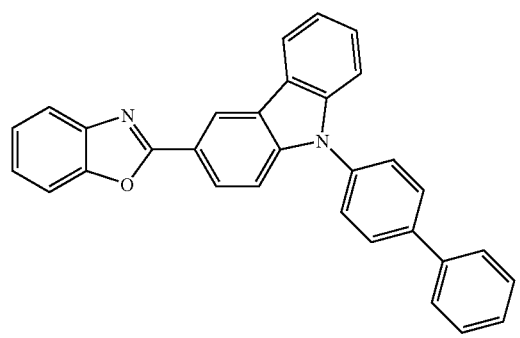
(321)
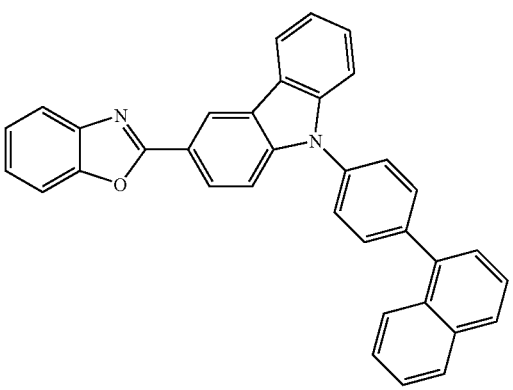
(322)
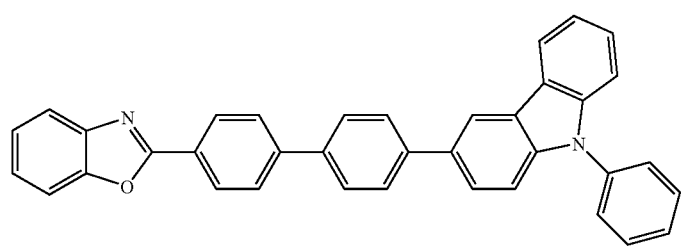

-continued
(323)
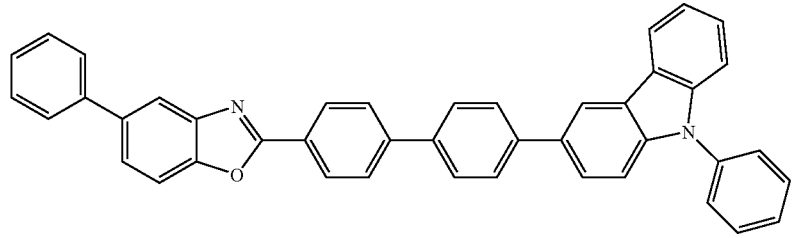
(324)
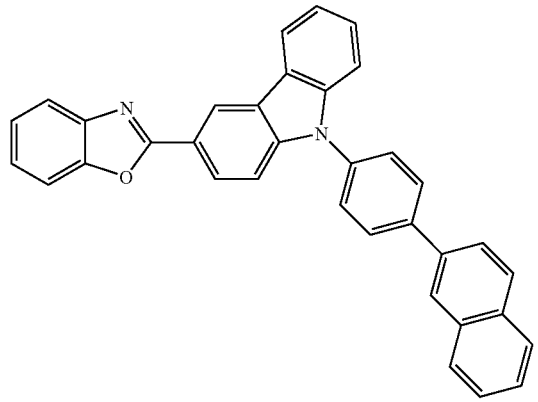
(325)
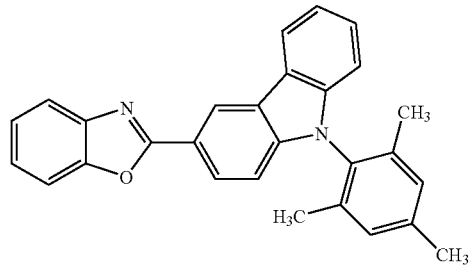
(326)
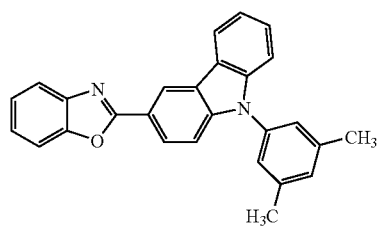
(327)
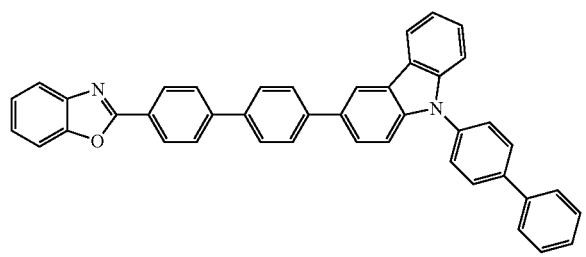
(328)
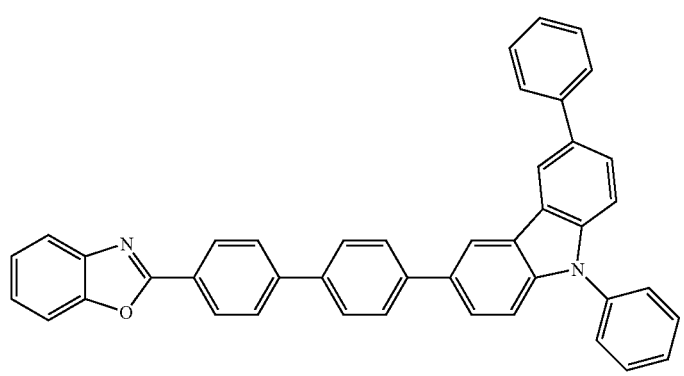
(329)
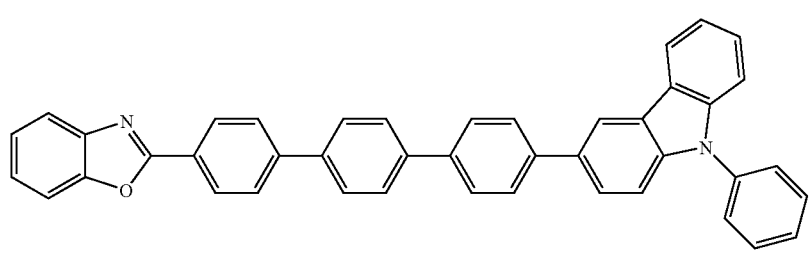

-continued
(330)
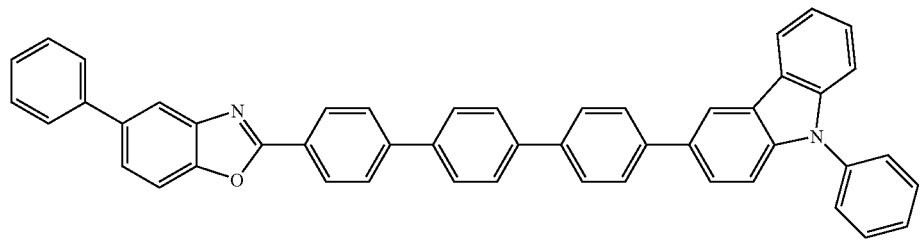
(331)
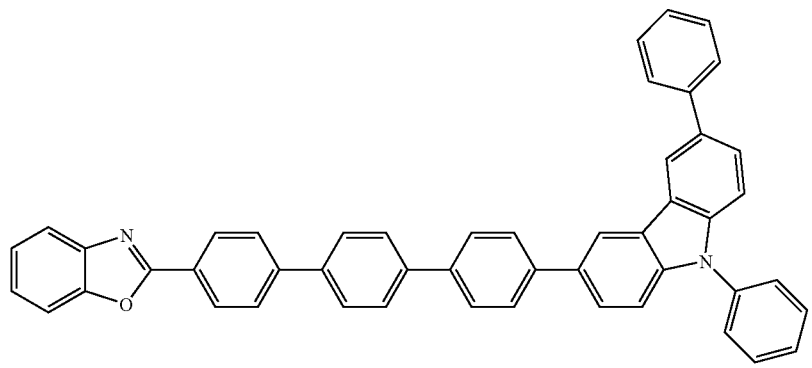
(332)
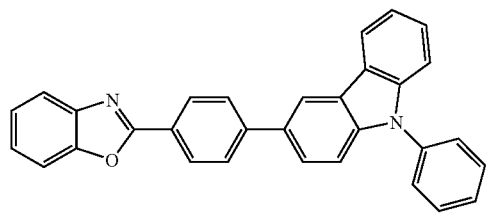
(333)
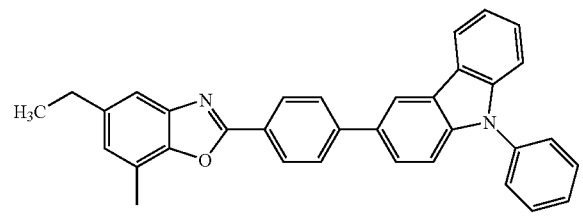
(334)
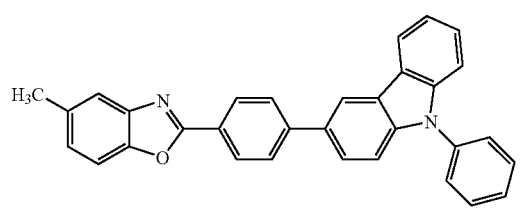
(335)
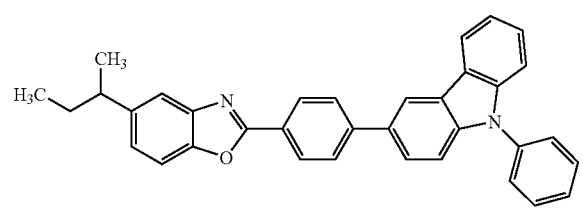
(336)
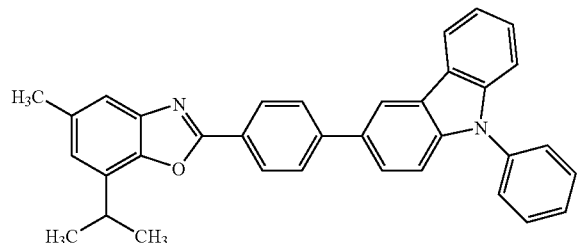
(337)
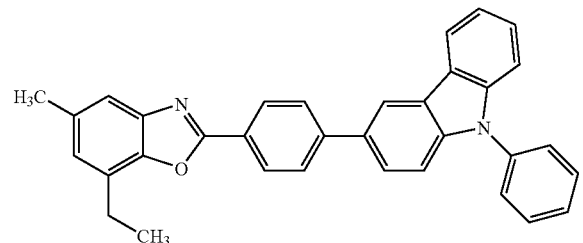
(338)
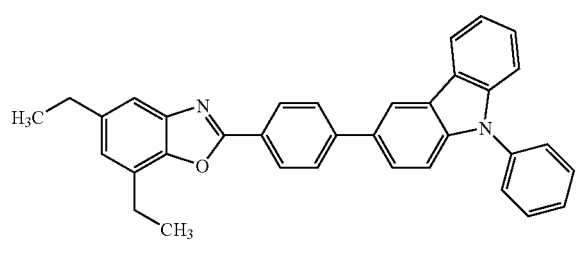
(339)
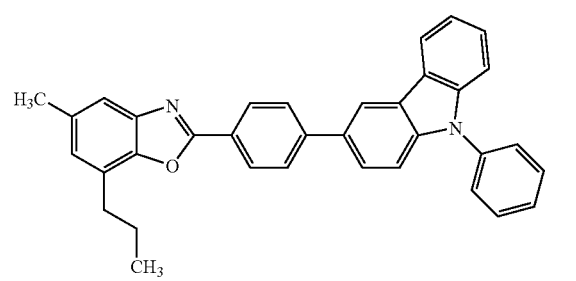

-continued
(340)
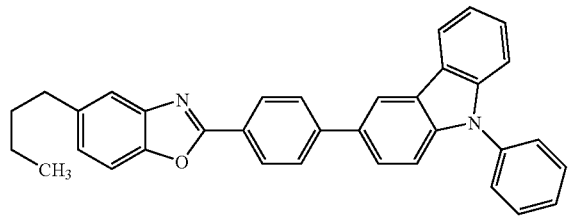
(341)
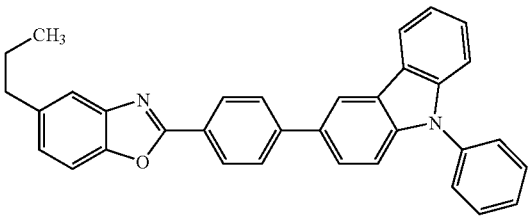
(342)
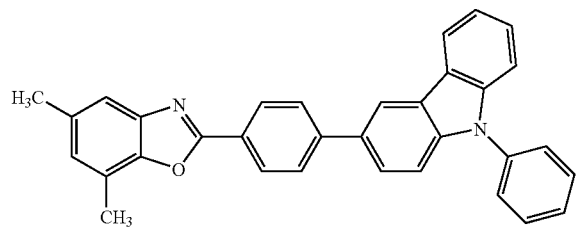
(343)
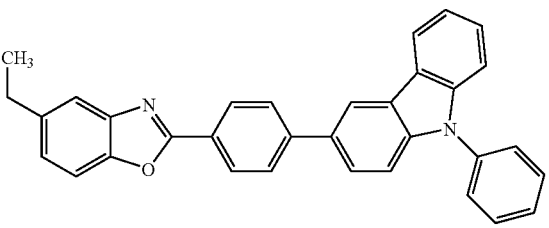
(344)
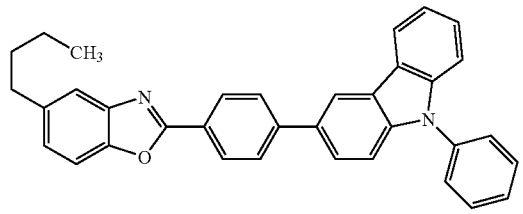
(345)
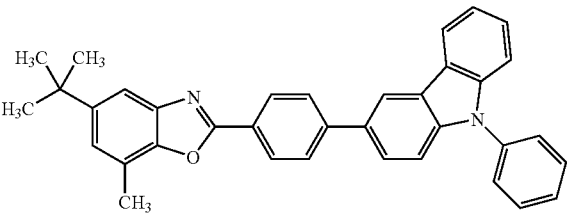
(346)
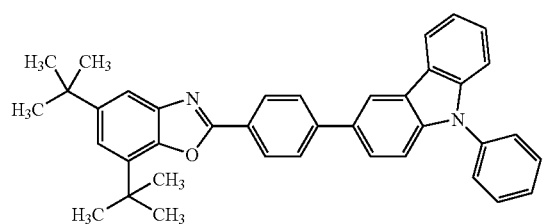
(347)
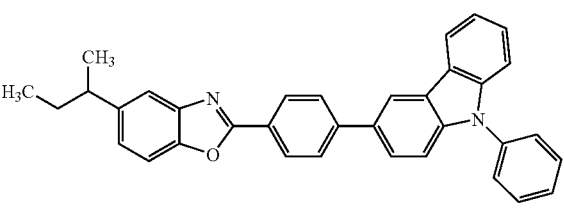
(348)
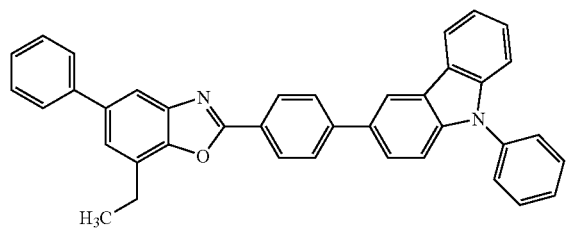
(349)
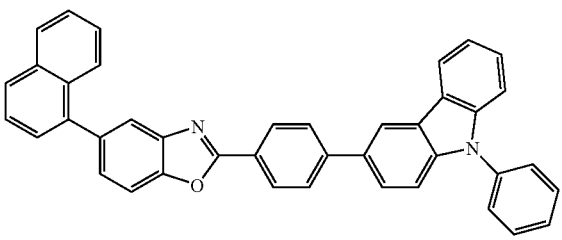
(350)
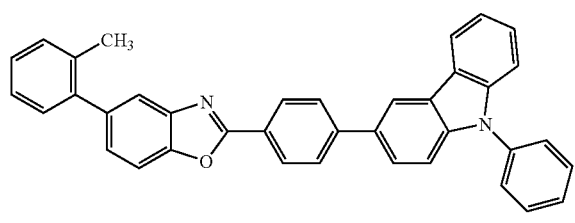
(351)
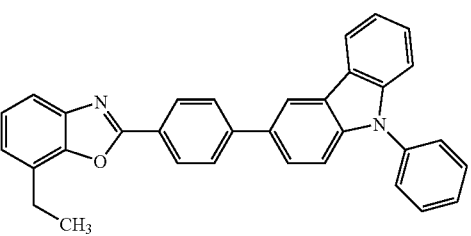

-continued
(352)
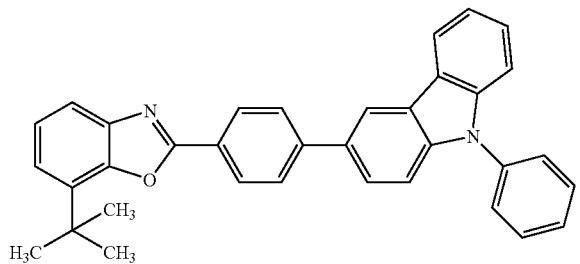
(353)
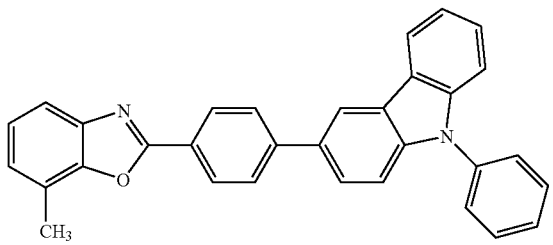
(354)
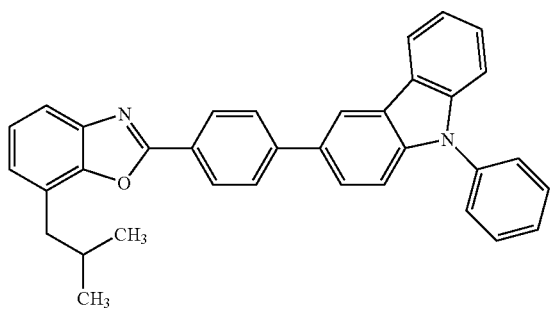
(355)
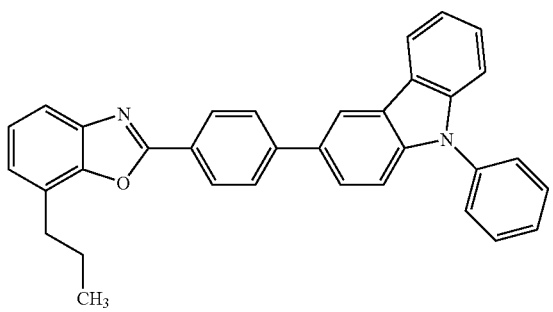
(356)
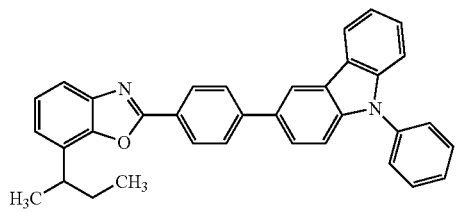
(357)
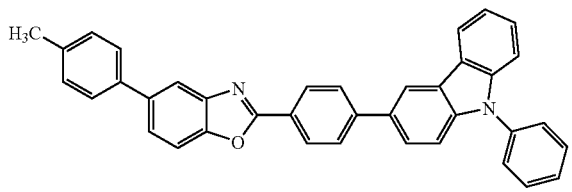
(358)
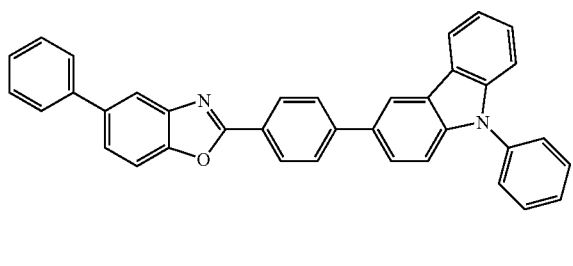
(359)
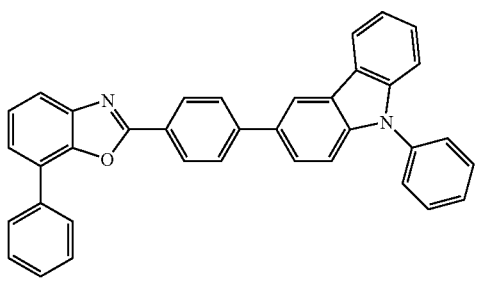
(360)
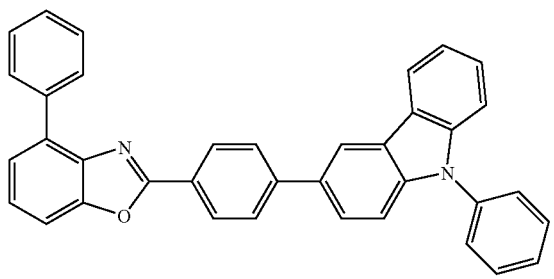
(361)
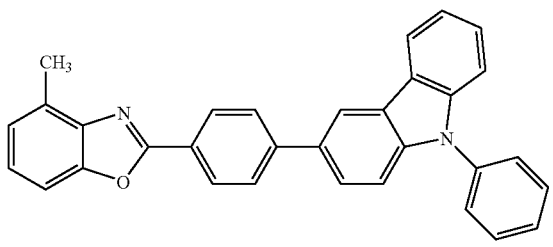

(362)
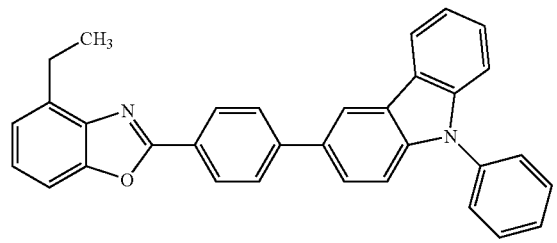
(363)
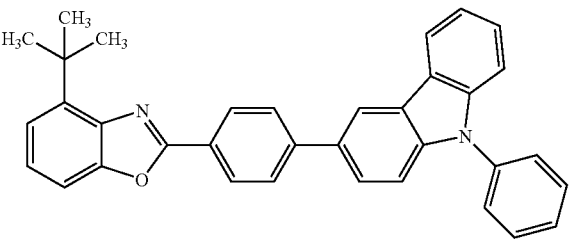
(364)
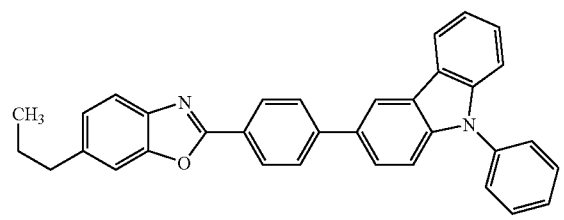
(365)
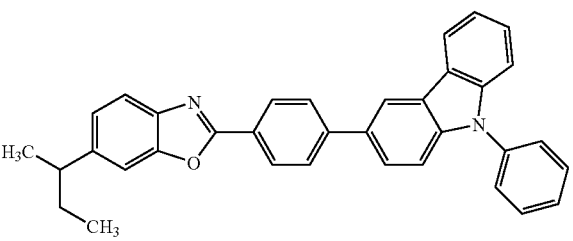
(366)
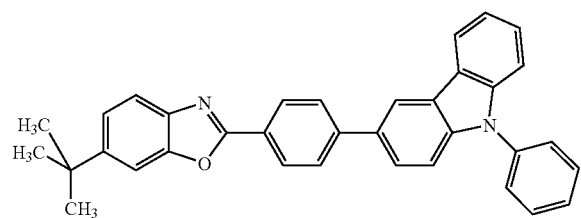
(367)
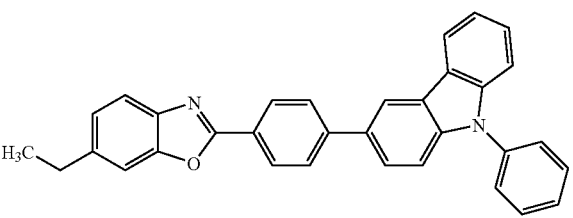
(368)
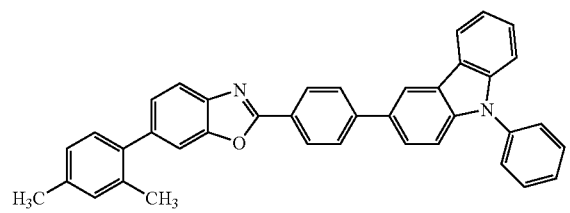
(369)
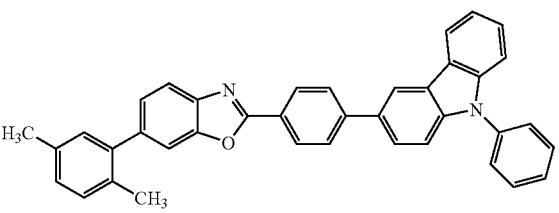
(370)
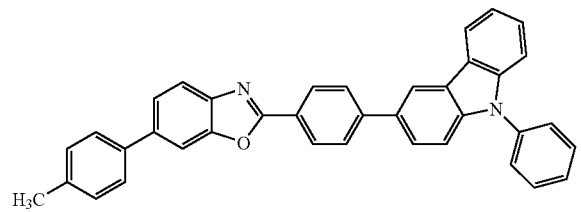
(371)
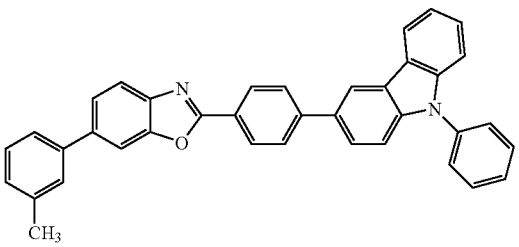
(372)
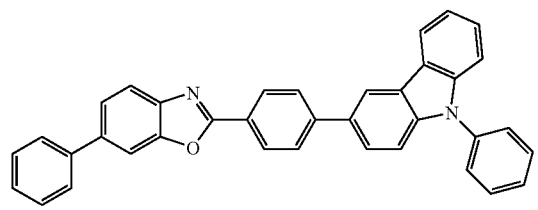
(373)
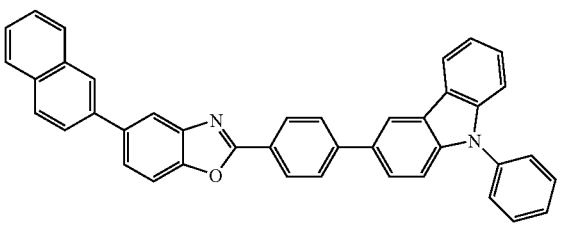

-continued
(374)
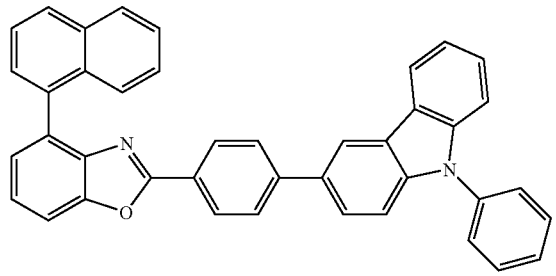
(375)
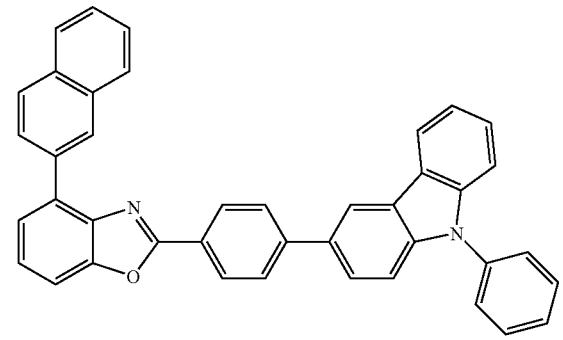
(376)
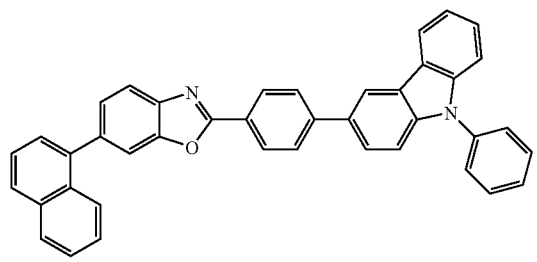
(377)
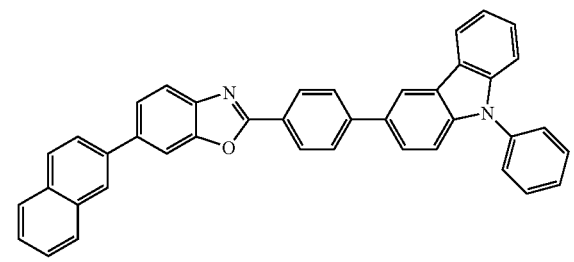
(378)
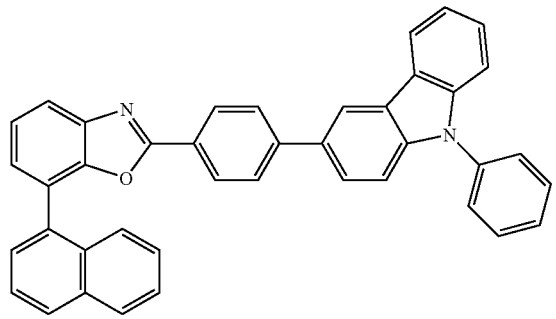
(379)
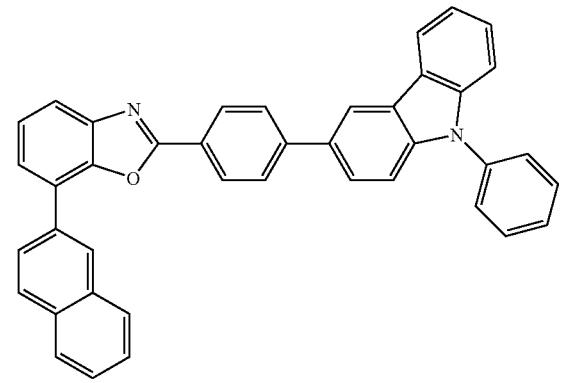
(380)
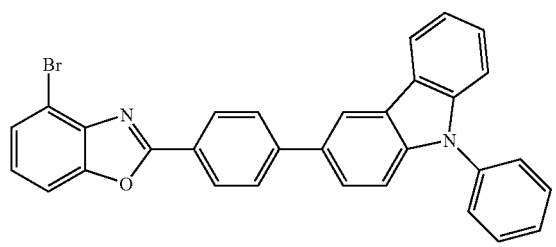
(381)
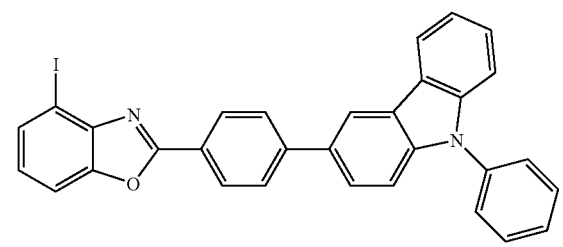
(382)
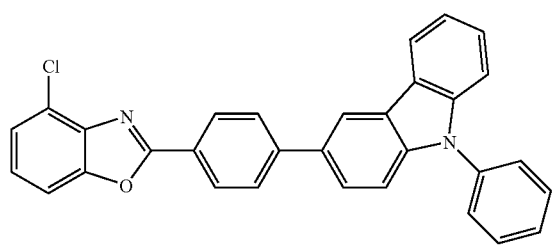
(383)
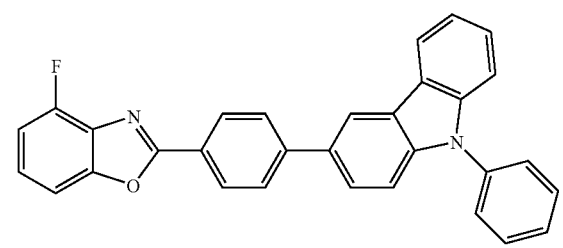

-continued
(384)
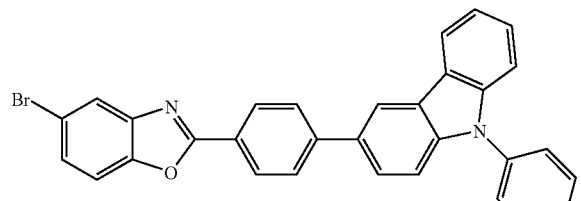
(385)
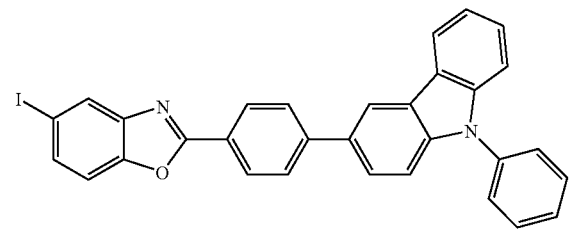
(386)
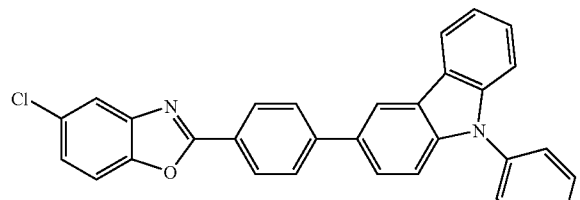
(387)
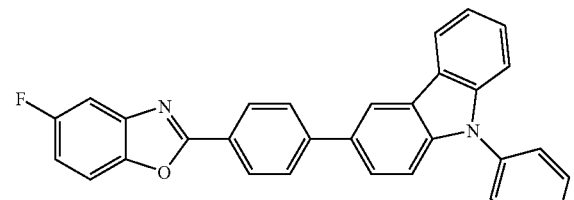
(388)
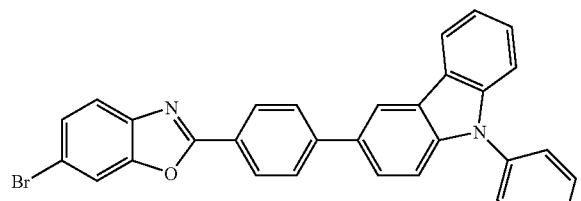
(389)
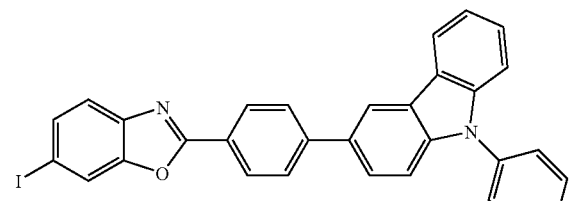
(390)
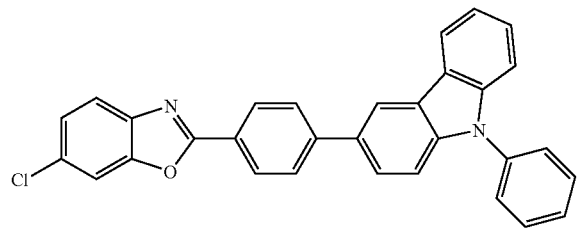
(391)
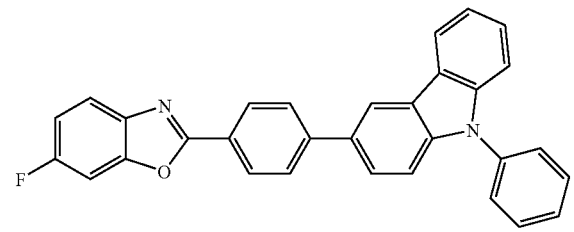
(392)
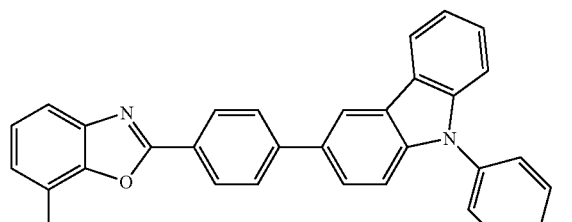
(393)
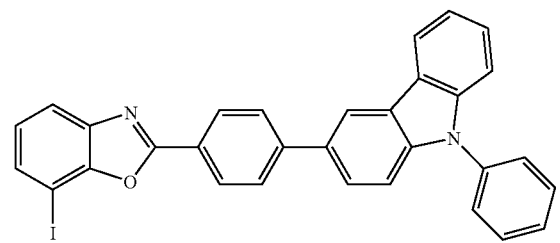
(394)
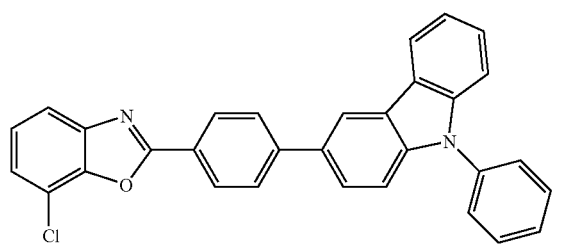
(395)
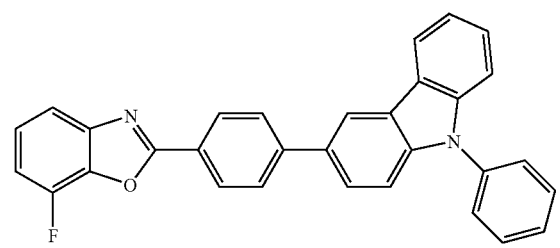

-continued
(396)
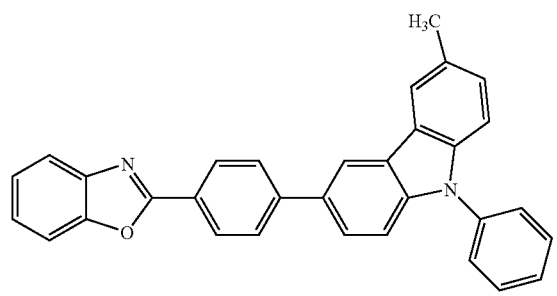
(397)
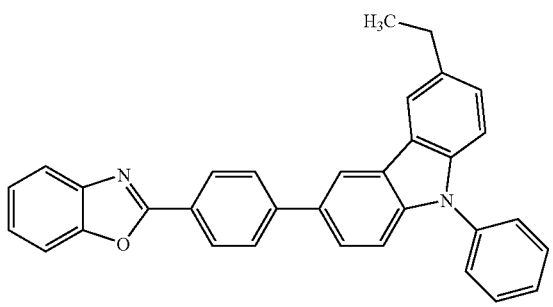
(398)
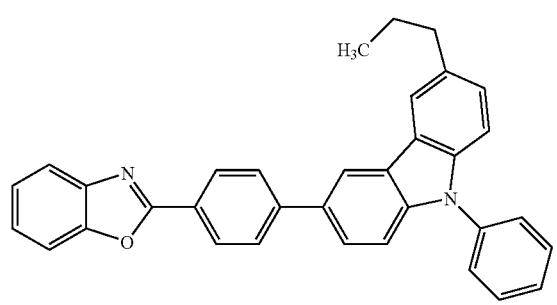
(399)
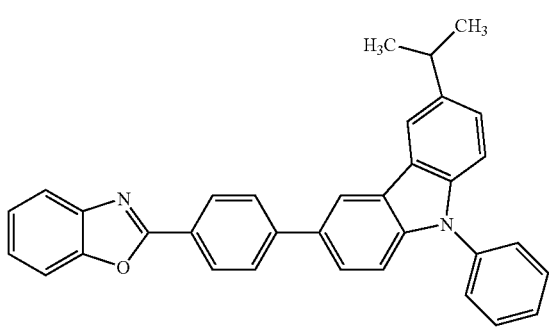
(400)
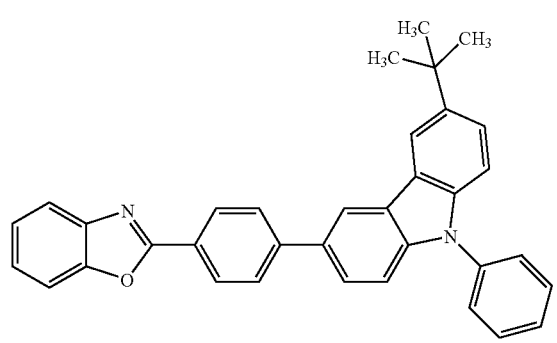
(401)
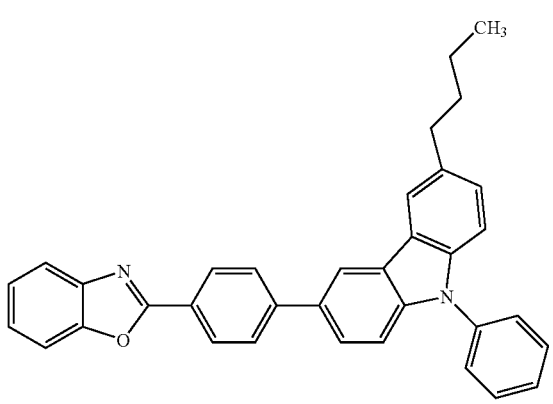
(402)
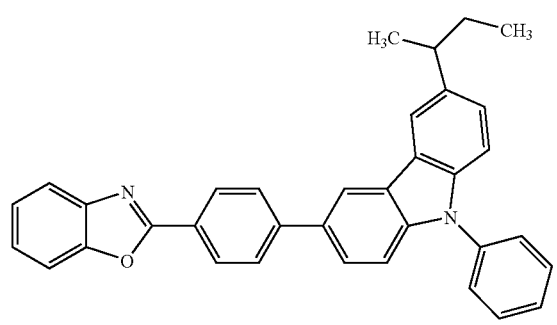
(403)
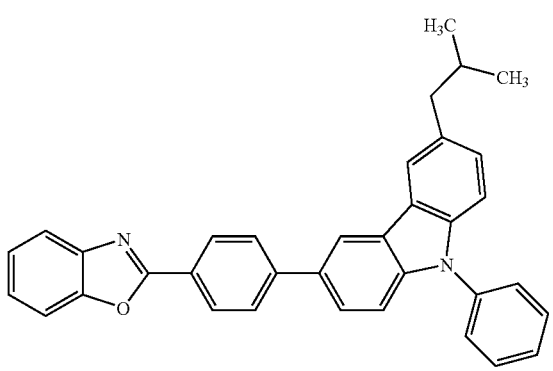

-continued
(404)
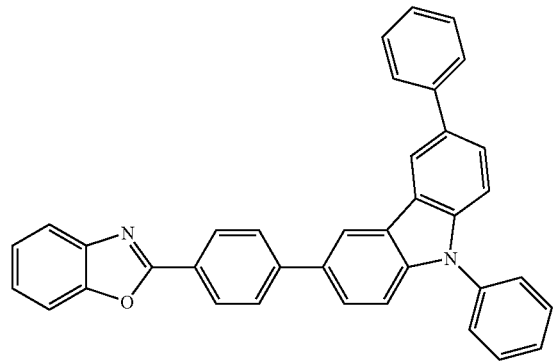
(405)
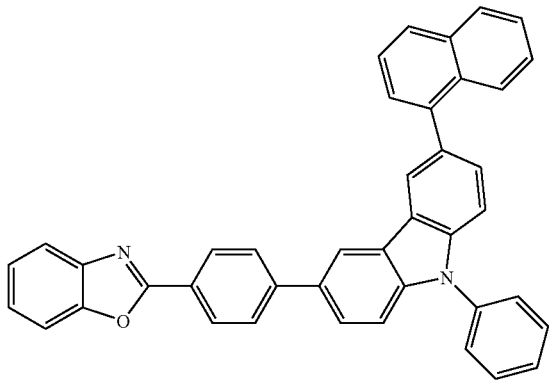
(406)
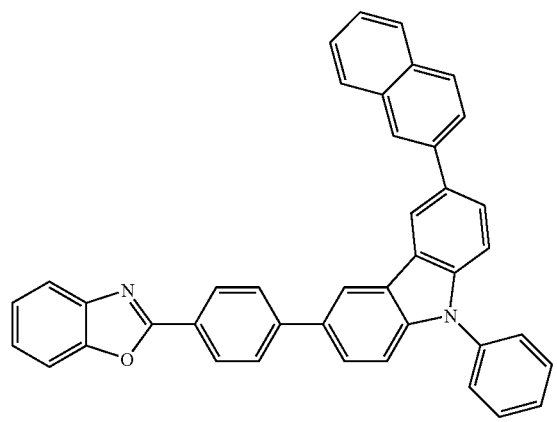
(407)
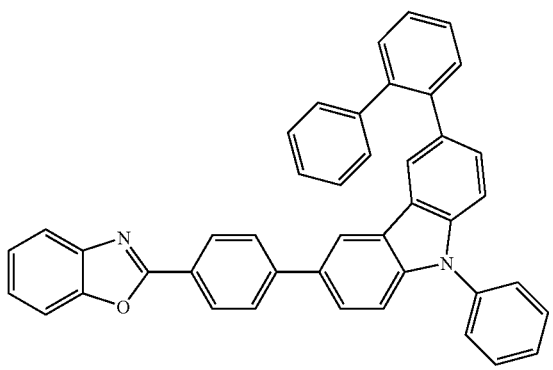
(408)
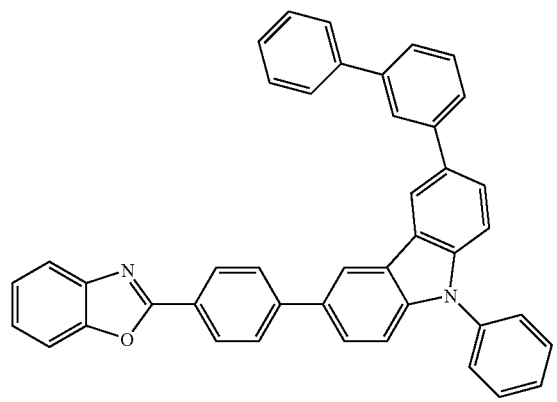
(409)
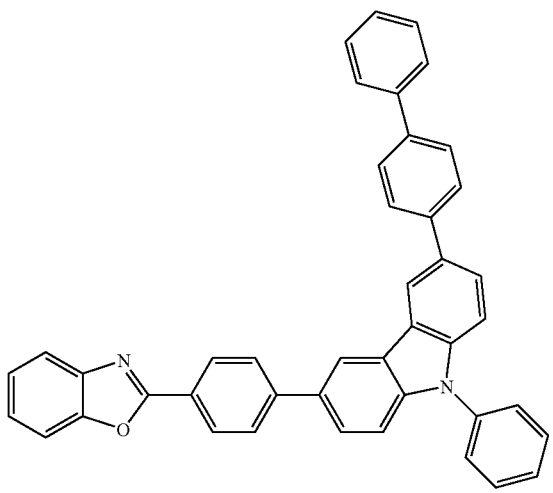

-continued
(410)
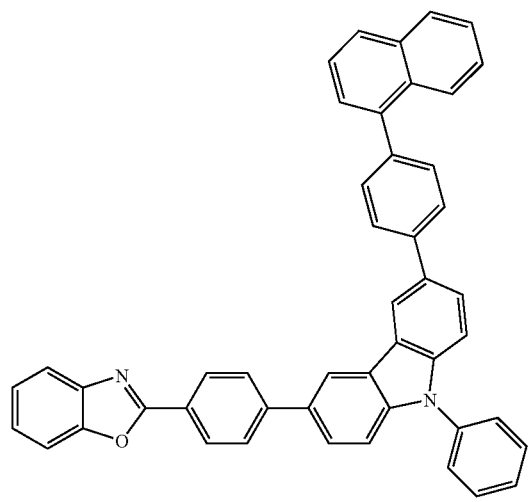
(411)
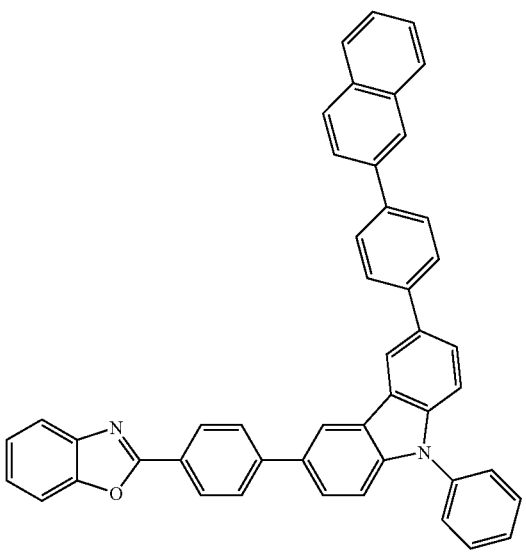
(412)
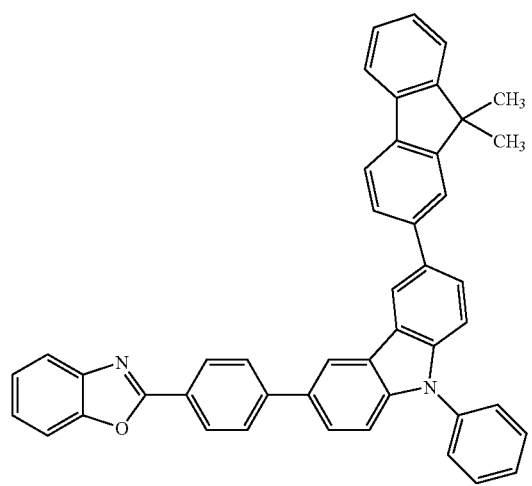
(413)
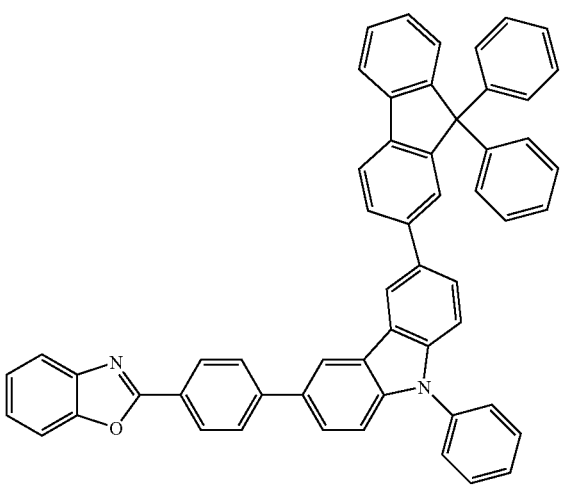
(414)
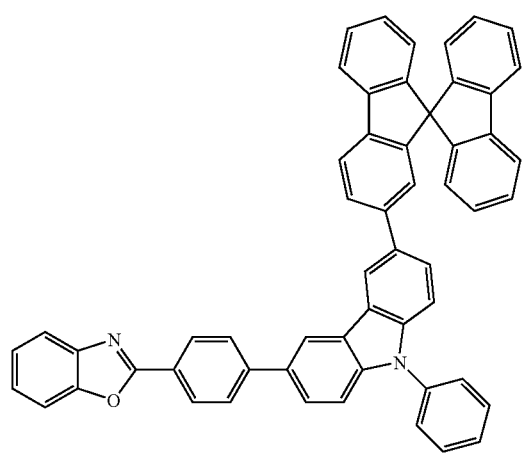
(415)
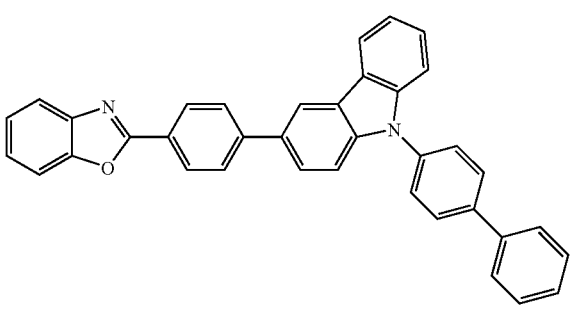

-continued
(416)
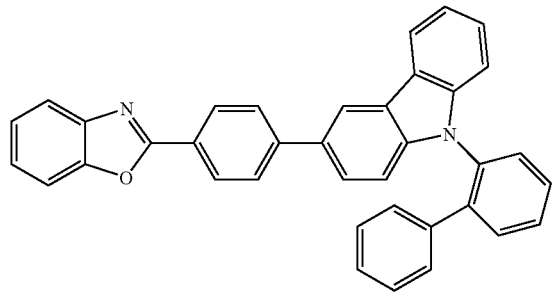
(417)
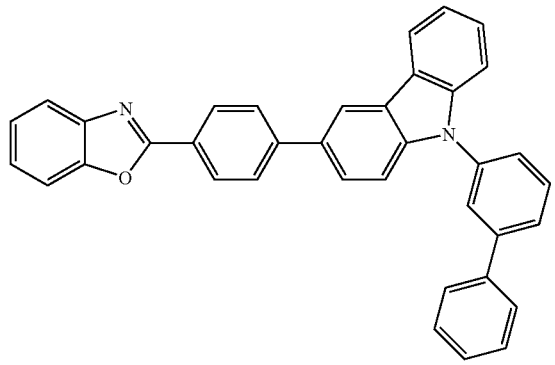
(418)
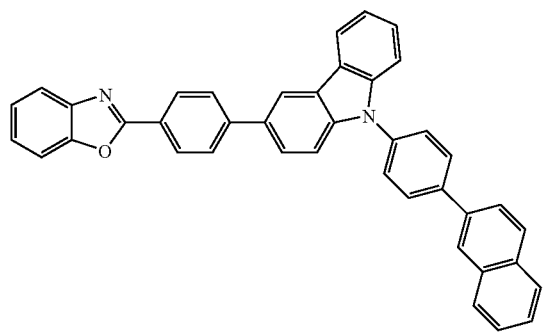
(419)
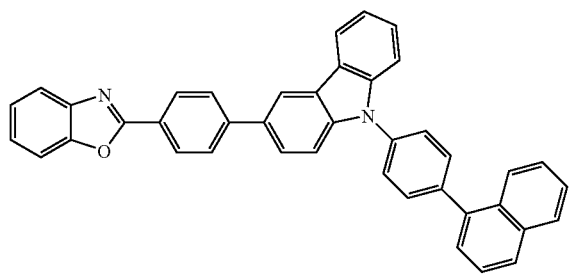
(420)
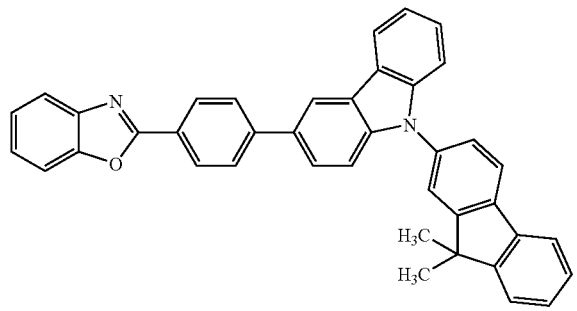
(421)
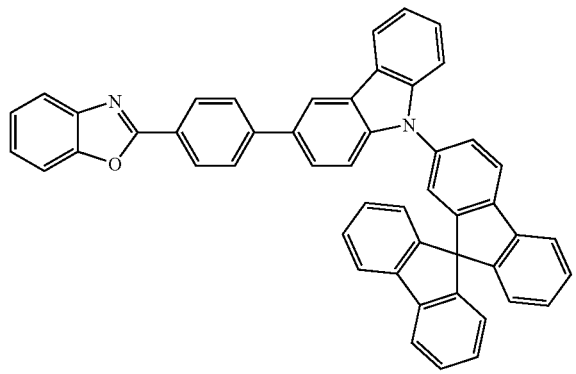
(422)
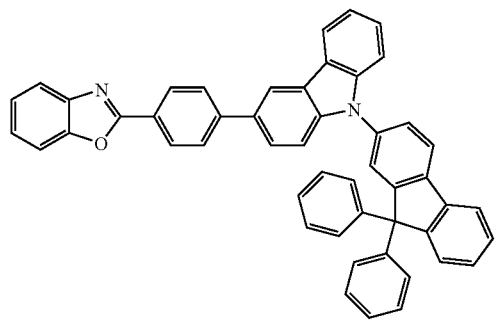
(423)
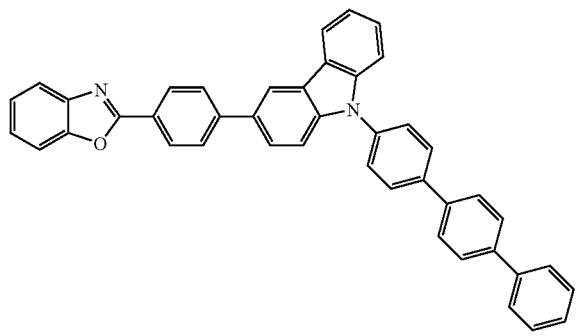

-continued
(424)
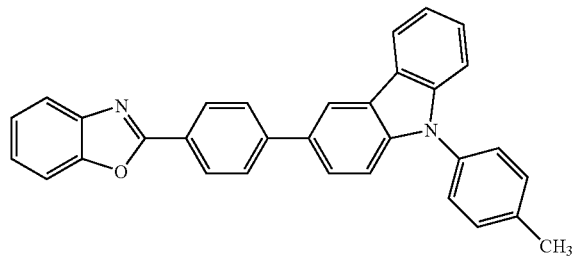
(425)
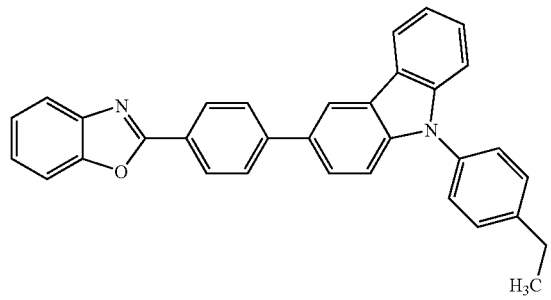
(426)
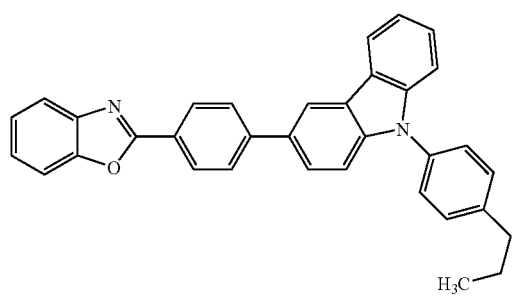
(427)
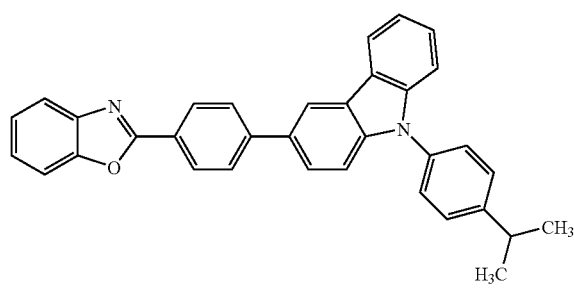
(428)
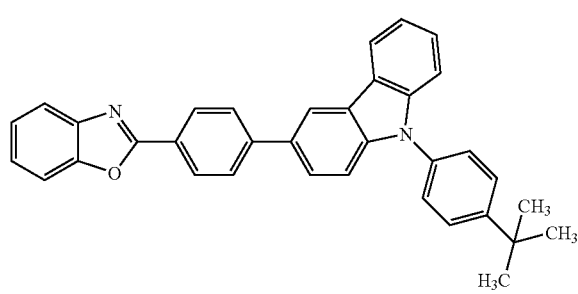
(429)
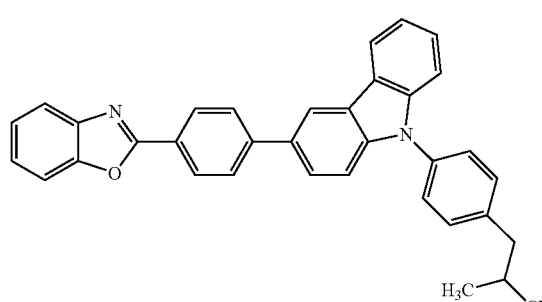
(430)
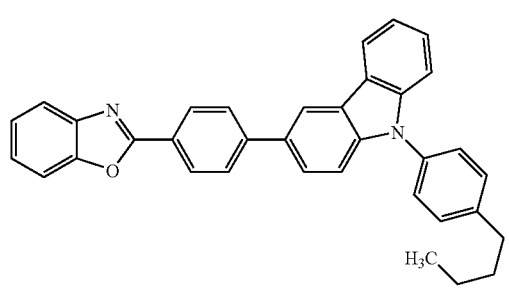
(431)
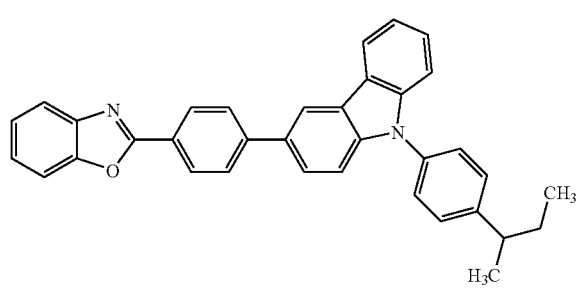
(432)
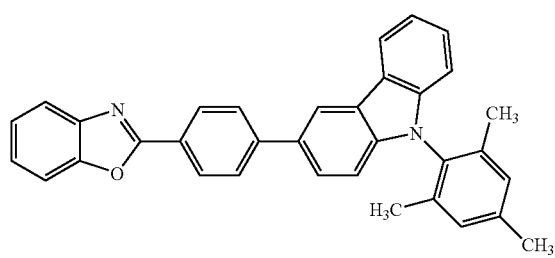
(433)
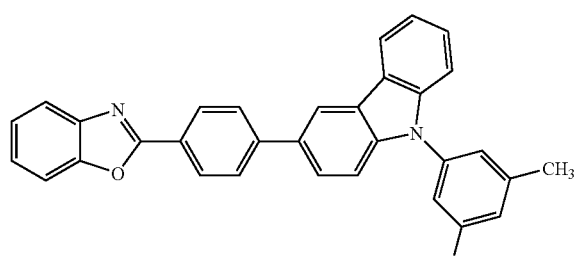

As methods for synthesizing the benzoxazole derivatives of the present invention, various reactions can be used. For example, the benzoxazole derivatives of the present invention which are represented by General Formula (G1) below can be synthesized by, for example, synthesis reactions described hereinbelow. Note that methods for synthesizing the benzoxazole derivatives of the present invention are not limited to the synthesis methods below.

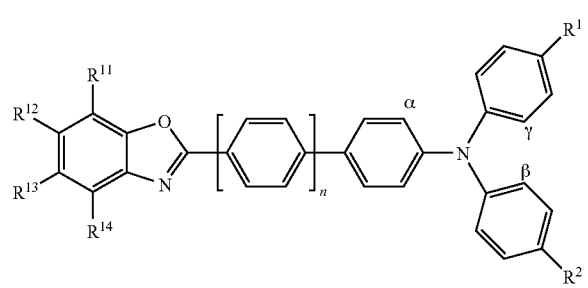

(G1)

<Method 1 for Synthesizing Benzoxazole Derivatives Represented by General Formula (G1)>

The benzoxazole compounds represented by General Formula (G1) can be synthesized by Synthesis Scheme (A-1). Specifically, the benzoxazole compounds (represented by General Formula (G1)) of the present invention can be obtained by coupling of a halide benzoxazole compound (Compound A1) and boronic acid of a carbazole compound or a compound in which a hydrogen atom of a 9H-carbazole compound is substituted with organoboron (Compound A2) according to a Suzuki-Miyaura reaction using a palladium catalyst.

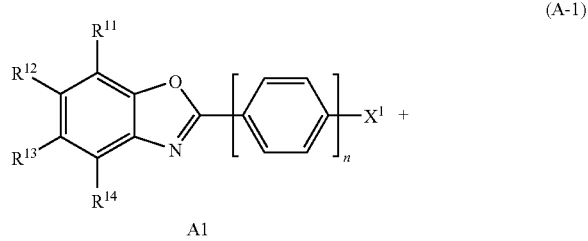

A1

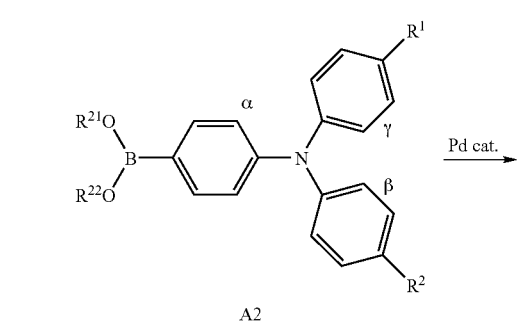

A2

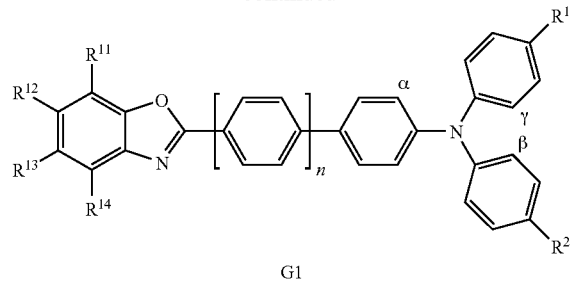

G1

In Synthesis Scheme (A-1), $X^1$ represents a halogen or a triflate group; as the halogen, iodine, bromine, or chlorine is used. Further, $R^{11}$ to $R^{14}$ independently represent a hydrogen atom, a halogen, an alkyl group with 1 to 4 carbon atoms, or an unsubstituted aryl group with 6 to 10 carbon atoms. Note that n is 0 to 3. Further, $R^1$ and $R^2$ independently represent a hydrogen atom, an alkyl group with 1 to 4 carbon atoms, or a substituted or unsubstituted aryl group with 6 to 13 carbon atoms. Note that substituents of the substituted aryl group may be bonded to form a ring which may form a spiro ring structure. Further, $R^{21}$ and $R^{22}$ independently represent hydrogen or an alkyl group with 1 to 4 carbon atoms and may be bonded to form a ring. Furthermore, a bond formed between any two of α, β, and γ forms a carbazole skeleton.

Examples of palladium catalysts that can be used in Synthesis Scheme (A-1) include palladium(II) acetate, tetrakis(triphenylphosphine)palladium(0), and the like. Examples of ligands of the palladium catalyst which can be used in Synthesis Scheme (A-1) include tri(ortho-tolyl)phosphine, triphenylphosphine, tricyclohexylphosphine, and the like.

Examples of bases that can be used in Synthesis Scheme (A-1) include an organic base such as sodium tert-butoxide, an inorganic base such as potassium carbonate, and the like.

Examples of solvents that can be used in Synthesis Scheme (A-1) include a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of an ether such as 1,2-dimethoxyethane and water; and the like. In addition, use of a mixed solvent of toluene and water or a mixed solvent of toluene, ethanol, and water is more preferable.

<Method 2 for Synthesizing Compounds Represented by General Formula (G1)>

The benzoxazole compound represented by General Formula (G1) can also be synthesized by Synthesis Scheme (B-1). Specifically, the benzoxazole compounds represented by General Formula (G1) of the present invention can also be obtained by coupling of boronic acid of a benzoxazole compound or a compound in which a hydrogen atom of a benzoxazole compound is substituted with organoboron (Compound B1) and a halide 9H-carbazole compound (Compound B2) according to a Suzuki-Miyaura reaction using a palladium catalyst.

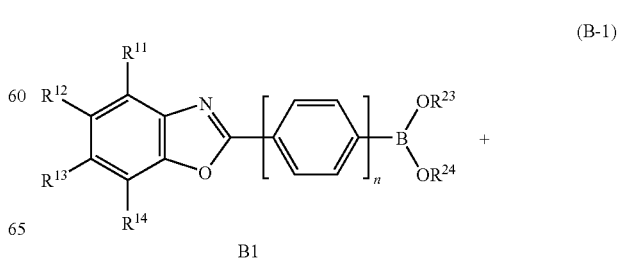

B1

(B-1)

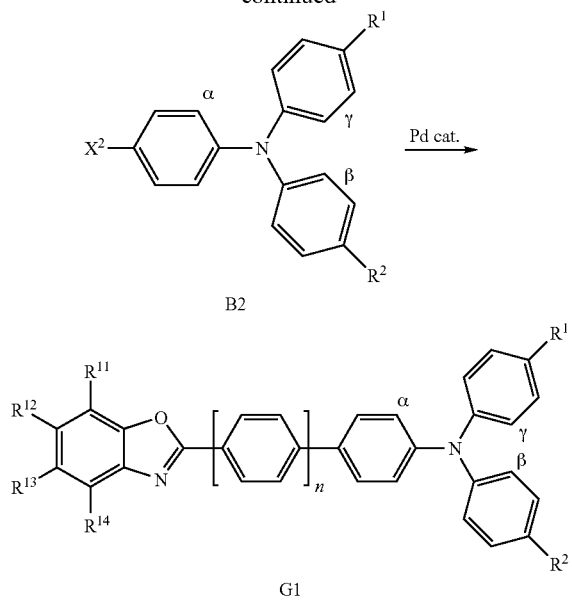

B2

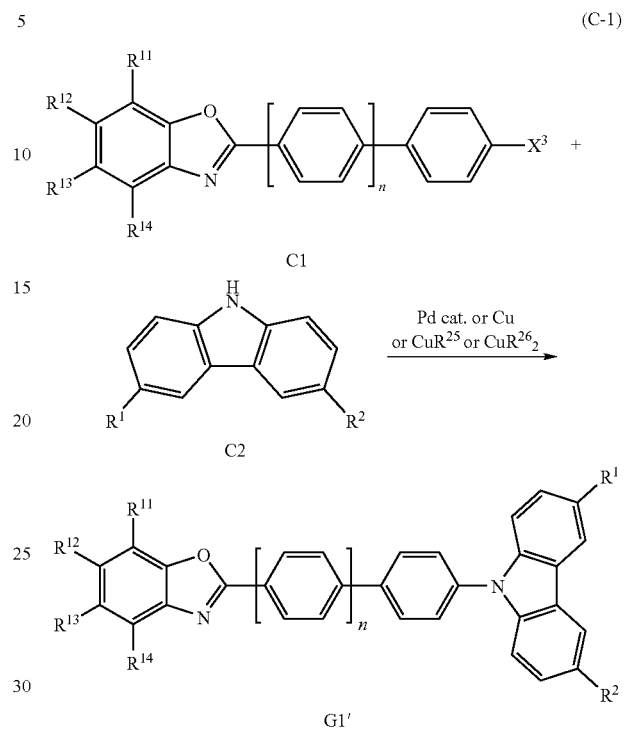

G1

In Synthesis Scheme (B-1), $X^2$ represents a halogen or a triflate group; as the halogen, iodine, bromine, or chlorine is used. Further, $R^1$ and $R^2$ independently represent a hydrogen atom, an alkyl group with 1 to 4 carbon atoms, or a substituted or unsubstituted aryl group with 6 to 13 carbon atoms. Note that substituents of the substituted aryl group may be bonded to form a ring which may form a spiro ring structure. Furthermore, a bond formed between any two of α, β, and γ forms a carbazole skeleton. $R^{11}$ to $R^{14}$ independently represent a hydrogen atom, a halogen, an alkyl group with 1 to 4 carbon atoms, or an unsubstituted aryl group with 6 to 10 carbon atoms. Further, $R^{23}$ and $R^{24}$ independently represent hydrogen or an alkyl group with 1 to 4 carbon atoms and may be bonded to form a ring. Note that n is 0 to 3.

Examples of palladium catalysts that can be used in Synthesis Scheme (B-1) include palladium(II) acetate, tetrakis (triphenylphosphine)palladium(0), and the like. Examples of ligands of the palladium catalyst which can be used in Synthesis Scheme (B-1) include tri(ortho-tolyl)phosphine, triphenylphosphine, tricyclohexylphosphine, and the like.

Examples of bases that can be used in Synthesis Scheme (B-1) include an organic base such as sodium tert-butoxide, an inorganic base such as potassium carbonate, and the like.

Examples of solvents that can be used in Synthesis Scheme (B-1) include a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of an ether such as 1,2-dimethoxyethane and water; and the like. In addition, use of a mixed solvent of toluene and water or a mixed solvent of toluene, ethanol, and water is more preferable.

<Method 3 for Synthesizing Compounds Represented by General Formula (G1))

The benzoxazole compound represented by General Formula (G1') can also be synthesized by Synthesis Scheme (C-1). Specifically, the benzoxazole compounds represented by General Formula (G1') of the present invention can be obtained by coupling of a halide benzoxazole compound (Compound C1) and a 9H-carbazole compound (Compound C2) with the use of a metal catalyst, metal, or a metal compound in the presence of a base.

In Synthesis Scheme (C-1), $X^3$ represents a halogen or a triflate group; as the halogen, iodine or bromine is used. Further, $R^{11}$ to $R^{14}$ independently represent a hydrogen atom, a halogen, an alkyl group with 1 to 4 carbon atoms, or an unsubstituted aryl group with 6 to 10 carbon atoms. Note that n is 0 to 3. Further, $R^1$ and $R^2$ independently represent a hydrogen atom, an alkyl group with 1 to 4 carbon atoms, or a substituted or unsubstituted aryl group with 6 to 13 carbon atoms. Note that substituents of the substituted aryl group may be bonded to form a ring which may form a spiro ring structure.

In Synthesis Scheme (C-1), when a Hartwig-Buchwald reaction is carried out, examples of palladium catalysts that can be used include bis(dibenzylideneacetone)palladium(0), palladium(II) acetate, and the like. Examples of ligands of the palladium catalyst which can be used in Synthesis Scheme (C-1) include tri(tert-butyl)phosphine, tri(n-hexyl)phosphine, tricyclohexylphosphine, and the like.

Examples of bases that can be used in Synthesis Scheme (C-1) include an organic base such as sodium tert-butoxide, an inorganic base such as potassium carbonate, and the like.

Examples of solvents that can be used in Synthesis Scheme (C-1) include toluene, xylene, benzene, tetrahydrofuran, and the like.

Further, the case in which an Ullmann reaction is carried out in Synthesis Scheme (C-1) is described. In Synthesis Scheme (C-1), $R^{25}$ and $R^{26}$ independently represent a halogen, an acetyl group, or the like; as the halogen, chlorine, bromine, or iodine can be used. Further, copper(I) iodide in which $R^{25}$ is iodine or copper(II) acetate in which $R^{26}$ is an acetyl group is preferable. As an alternative to the copper compound, copper can be used.

As bases that can be used in Synthesis Scheme (C-1), an inorganic base such as potassium carbonate is given.

Examples of solvents that can be used in Synthesis Scheme (C-1) include, but not limited to, 1,3-dimethyl-3,4,5,6-tetrahydro-2(1H)pyrimidinone (DMPU), toluene, xylene, benzene, and the like. In an Ullmann reaction, since a reaction temperature of 100° C. or more enables a desired object in a shorter time and a higher yield, DMPU or xylene, which has a high boiling point, is preferably used. In addition, since the reaction temperature is further preferably 150° C. or more, DMPU is more preferably used.

Embodiment 2

In Embodiment 2, a light-emitting element in which any of the benzoxazole derivatives of the present invention which are described in Embodiment 1 is used for a light-emitting layer will be described.

The light-emitting element in Embodiment 2 includes a first electrode which functions as an anode, a second electrode which functions as a cathode, and an EL layer provided between the first electrode and the second electrode. Note that the light-emitting element in Embodiment 2 can provide light emission when a voltage is applied to each electrode so that the potential of the first electrode is higher than that of the second electrode.

In addition, the EL layer of the light-emitting element in Embodiment 2 includes a first layer (hole-inject layer), a second layer (hole-transport layer), a third layer (light-emitting layer), a fourth layer (electron-transport layer), and a fifth layer (electron-inject layer), from the first electrode side.

Figure 1B:
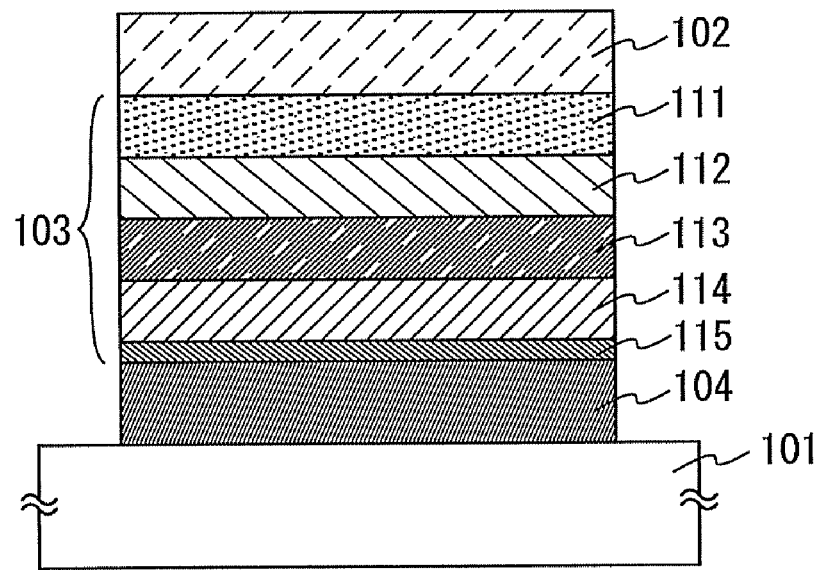

A structure of the light-emitting element in Embodiment 2 is described using FIGS. 1A and 1B. A substrate 101 is used as a support of the light-emitting element. For the substrate 101, glass, quartz, plastics, or the like can be used, for example.

Note that the above substrate 101 may remain in a light-emitting device or an electronic device which is a product utilizing the light-emitting element of the present invention, but may only have a function of a support of the light-emitting element without remaining in an end product.

For the first electrode 102 formed over the substrate 101, a metal, an alloy, an electrically conductive compound, a mixture thereof, or the like which has a high work function (specifically, a work function of 4.0 eV or more) is preferably used. Specific examples include indium oxide-tin oxide (ITO: indium tin oxide), indium oxide-tin oxide containing silicon or silicon oxide, indium oxide-zinc oxide (IZO: indium zinc oxide), and indium oxide containing tungsten oxide and zinc oxide, and the like. Other than these, there are gold (Au), platinum (Pt), nickel (Ni), tungsten (W), chromium (Cr), molybdenum (Mo), iron (Fe), cobalt (Co), copper (Cu), palladium (Pd), titanium (Ti), nitrides of metal materials (e.g., titanium nitride), and the like. Note that in the present invention, since the first layer 111 in the EL layer 103 which is formed in contact with the first electrode 102 includes a composite material which facilitates hole injection regardless of the work function of the first electrode 102, any known material can be used as long as the material can be used as an electrode material (e.g., a metal, an alloy, an electrically conductive compound, a mixture thereof, and an element belonging to Group 1 or Group 2 of the periodic table).

A film of such a material is usually formed by a sputtering method. For example, a film of indium oxide-zinc oxide (IZO) can be formed by a sputtering method using a target in which 1 to 20 wt % zinc oxide is added to indium oxide; and a film of indium oxide containing tungsten oxide and zinc oxide can be formed by a sputtering method using a target in which 0.5 to 5 wt % tungsten oxide and 0.1 to 1 wt % zinc oxide are added to indium oxide. Alternatively, a vacuum evaporation method, a coating method, an inkjet method, a spin coating method, or the like may be used.

Further, when a layer including a composite material which will be described later is used as a material used for the first layer 111 formed in contact with the first electrode 102 in the EL layer 103 formed over the first electrode 102, any of a variety of materials such as metals, alloys, and electrically conductive compounds; a mixture thereof; or the like can be used as a substance used for the first electrode 102 regardless of their work functions. For example, aluminum (Al), silver (Ag), an alloy containing aluminum (AlSi), or the like can also be used.

Alternatively, it is possible to use any of elements belonging to Group 1 or 2 of the periodic table which have a low work function, i.e., alkali metals such as lithium (Li) and cesium (Cs); alkaline earth metals such as magnesium (Mg), calcium (Ca), and strontium (Sr); alloys containing any of these metals (e.g., MgAg and AlLi); rare earth metals such as europium (Eu) and ytterbium (Yb); alloys containing any of these metals; or the like.

Note that in the case where the first electrode 102 is formed using an alkali metal, an alkaline-earth metal, or an alloy thereof, a vacuum evaporation method or a sputtering method can be used. Further alternatively, in the case where a silver paste or the like is used, a coating method, an inkjet method, or the like can be used.

For the EL layer 103 formed over the first electrode 102, a known substance can be used, and any of low molecular compounds or high molecular compounds can be used. Note that the substance forming the EL layer 103 is not limited to an organic compound and may include an inorganic compound.

The EL layer 103 is formed by stacking an appropriate combination of a hole-inject layer that includes a substance having a high hole-inject property, a hole-transport layer that includes a substance having a high hole-transport property, a light-emitting layer that includes a light-emitting substance, an electron-transport layer that includes a substance having a high electron-transport property, an electron-inject layer that includes a substance having a high electron-inject property, and the like.

Note that the EL layer 103 illustrated in FIG. 1A includes the first layer (hole-inject layer) 111, the second layer (hole-transport layer) 112, the third layer (light-emitting layer) 113, the fourth layer (electron-transport layer) 114, and the fifth layer (electron-inject layer) 115 which are in that order stacked from the first electrode 102 side.

The first layer 111 which is a hole-inject layer is a hole-inject layer that includes a substance having a high hole-inject property. As the substance having a high hole-inject property, molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, or the like can be used. Alternatively, as a low molecular organic compound, a phthalocyanine-based compound such as phthalocyanine (abbreviation: $H_2Pc$), copper(II) phthalocyanine (abbreviation: CuPc), or vanadyl phthalocyanine (abbreviation: VOPc) can be used.

Further, as examples of low molecular organic compounds, there are aromatic amine compounds such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N-phenylamino]phenyl}-N-phenylamino)biphenyl (abbreviation:

DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1), and the like.

Further alternatively, any of high molecular compounds (e.g., oligomers, dendrimers, or polymers) can be used. For example, any of the following high molecular compounds can be used: poly(N-vinylcarbazole) (abbreviation: PVK), poly (4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD). Alternatively, a high molecular compound to which acid is added, such as poly(3,4-ethylenedioxythiophene)/poly(styrenesulfonic acid) (PEDOT/PSS), or polyaniline/poly(styrenesulfonic acid) (PAni/PSS), can be used.

Alternatively, for the first layer 111, the composite material in which an acceptor substance is mixed into a substance having a high hole-transport property can be used. Note that by using the material in which an acceptor substance is mixed into a substance having a high hole-transport property, a material used to form an electrode may be selected regardless of the work function. That is, besides a material having a high work function, a material having a low work function may be used as the first electrode 102. Such a composite material can be formed by co-evaporation of a substance having a high hole-transport property and an acceptor substance. Note that in the present specification, "composition" means not only a simple mixture of two materials but also a mixture of a plurality of materials in a condition where an electric charge is given and received among the materials.

As an organic compound used for the composite material, any of a variety of compounds such as aromatic amine compounds, carbazole derivatives, aromatic hydrocarbons, or high molecular compounds (oligomers, dendrimers, polymers, etc.) can be used. Note that an organic compound used for the composite material preferably has a high hole-transport property. Specifically, a substance having a hole mobility of $10^{-6}$ cm$^2$/Vs or more is preferably used. Further, any other substance may be used as long as it is a substance in which the hole-transport property is higher than the electron-transport property. Organic compounds that can be used for the composite material are specifically given below.

For example, as the organic compounds that can be used for the composite material, there are aromatic amine compounds such as MTDATA, TDATA, DPAB, DNTPD, DPA3B, PCz-PCA1, PCzPCA2, PCzPCN1, 4,4'-bis[N-(1-naphthyl)-N-phenylamino]biphenyl (abbreviation: NPB or α-NPD), and N,N'-bis(3-methylphenyl)-N,N'-diphenyl-[1,1'-biphenyl]-4,4'-diamine (abbreviation: TPD); and carbazole derivatives such as 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)]phenyl-10-phenylanthracene (abbreviation: CzPA), and 1,4-bis[4-(N-carbazolyl)phenyl-2,3,5,6-tetraphenylbenzene.

Further, there are aromatic hydrocarbon compounds such as 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butyl-anthracene, 9,10-bis[2-(1-naphthyl)phenyl]anthracene, and 2,3,6,7-tetramethyl-9,10-di(1-naphthyl) anthracene.

Furthermore, there are aromatic hydrocarbon compounds such as 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), and 9,10-bis[4-(2,2-diphenylvinyl)phenyl] anthracene (abbreviation: DPVPA).

Further, as examples of the acceptor substance, there are organic compounds such as 7,7,8,8-tetracyano-2,3,5,6-tetrafluoroquinodimethane (abbreviation: F$_4$-TCNQ) and chloranil, and transition metal oxides. Furthermore, other examples include oxides of metals belonging to Group 4 to Group 8 of the periodic table. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable because it is stable in air and its hygroscopic property is low so that it can be easily handled.

Note that for the first layer 111, a composite material formed using any of the above-mentioned high molecular compounds such as PVK, PVTPA, PTPDMA, or Poly-TPD and any of the above-mentioned acceptor substances may be used.

The second layer 112 which is a hole-transport layer includes a substance having a high hole-transport property. As a substance having a high hole-transport property, a low molecular organic compound can be used, and examples thereof include aromatic amine compounds such as NPB (or α-NPD), TPD, 4,4'-bis[N-(9,9-dimethylfluoren-2-yl)-N-phenylamino]biphenyl (abbreviation: DFLDPBi), and 4,4'-bis[N-(spiro-9,9'-bifluoren-2-yl)-N-phenylamino]biphenyl (abbreviation: BSPB). The substances mentioned here are mainly substances having a hole mobility of $10^{-6}$ cm$^2$/Vs or more. However, any other substance may also be used as long as it is a substance in which the hole-transport property is higher than the electron-transport property. Note that the hole-transport layer is not limited to a single layer and may be a stack of two or more layers including any of the above-mentioned substances.

Alternatively, for the second layer 112, the above-mentioned composite material in which an acceptor substance is mixed into a substance having a high hole-transport property may be used.

Further alternatively, for the second layer 112, a high molecular compound such as PVK, PVTPA, PTPDMA, or Poly-TPD can be used.

The third layer 113 is a layer including a substance having a high light-emitting property. Note that in Embodiment 2, any of the benzoxazole derivatives of the present invention is used for the light-emitting layer. Any of the benzoxazole derivatives of the present invention can be used alone for the light-emitting layer or alternatively as a host material of the light-emitting layer in which a substance having a high light-emitting property (guest material) is dispersed in another substance (host material).

In the case where any of the benzoxazole derivatives described in Embodiment 1 is used as the host material and the guest material emits fluorescence, it is preferable to use, as the guest material, a substance whose lowest unoccupied molecular orbital (LUMO) level is lower than that of the benzoxazole derivative and whose highest occupied molecular orbital (HOMO) level is higher than that of the benzoxazole derivative. Examples of materials for blue light emission include N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), and the like. Examples of materials for green light emission include N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), and the like. Further, examples of materials for yellow light emission include rubrene, 5,12-bis(1,1'-biphenyl-4-yl)-6,11-diphenyltetracene (abbreviation: BPT), and the like. Further, examples of materials for red light emission include N,N,N', N'-tetrakis(4-methylphenyl)tetracene-5,11-diamine (abbreviation: p-mPhTD), 7,13-diphenyl-N,N,N',N'-tetrakis(4-methylphenyl)acenaphtho[1,2-α]fluoranthene-3,10-diamine (abbreviation: p-mPhAFD), and the like.

Alternatively, in the case where any of the benzoxazole derivatives described in Embodiment 1 is used as the host material and the guest material emits phosphorescence, it is preferable to use, as the guest material, a substance having lower triplet excitation energy than the benzoxazole derivative. Examples include organometallic complexes such as bis[2-(2'-benzo[4,5-α]thienyl)pyridinato-N,$C^{3'}$]iridium(III) acetylacetonate (abbreviation: Ir(btp)$_2$(acac)), bis(1-phenyl-isoquinolinato-N,$C^{2'}$)iridium(III) acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), and 2,3,7,8,12,13,17,18-octaethyl-21H,23H-porphyrin platinum(II) (abbreviation: PtOEP).

Since the benzoxazole derivatives described in Embodiment 1 have an electron-transport property, by using any of the benzoxazole derivatives for a light-emitting layer, the light-emitting layer can have a high electron-transport property. Such a light-emitting layer can provide light emission with high efficiency by using a guest material having high electron-trapping property.

In addition, as the substance (host material) in which a light-emitting substance (guest material) is dispersed, plural kinds of substances can be used. Therefore, the light-emitting layer may include a second host material in addition to the any of benzoxazole derivatives described in Embodiment 1.

Further, any of the benzoxazole derivatives of the present invention can be used alone or as a light-emitting substance (as a guest material).

The fourth layer 114 is an electron-transport layer that includes a substance having a high electron-transport property. For the fourth layer 114, for example, as a low molecular organic compound, a metal complex, such as Alq, Almq$_3$, BeBq$_2$, BAlq, Znq, ZnPBO, or ZnBTZ, or the like can be used. Alternatively, instead of the metal complex, a heterocyclic compound such as PBD, OXD-7, TAZ, TPBI, BPhen, or BCP can be used. The substances described here are mainly materials having electron mobility of $10^{-6}$ cm$^2$/Vs or more. Note that any substance other than the above substances may be used for the electron-transport layer as long as it is a substance in which the electron-transport property is higher than the hole-transport property. Further, the electron-transport layer may be either a single layer or a stack of two or more layers including the above mentioned substances.

For the fourth layer 114, a high molecular compound can also be used. For example, poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridine-6,6'-diyl)] (abbreviation: PF-BPy), and the like can be used.

The fifth layer 115 is an electron-inject layer that includes a substance having a high electron-inject property. For the fifth layer 115, an alkali metal, an alkaline earth metal, or a compound thereof, such as lithium fluoride (LiF), cesium fluoride (CsF), or calcium fluoride (CaF$_2$), can be used. Alternatively, a layer of an electron-transport substance which contains an alkali metal, an alkaline earth metal, or a compound thereof, specifically, a layer of Alq which contains magnesium (Mg), or the like may be used. Note that in this case, electrons can be more efficiently injected from the second electrode 104.

For the second electrode 104, a metal, an alloy, an electrically conductive compound, a mixture thereof, or the like which has a low work function (specifically, a work function of 3.8 eV or less) can be used. As specific examples of such cathode materials, there are elements belonging to Group 1 or Group 2 of the periodic table, i.e., alkali metals such as lithium (Li) and cesium (Cs); alkaline earth metals such as magnesium (Mg), calcium (Ca), and strontium (Sr); alloys containing any of these metals (e.g., MgAg and AlLi); rare earth metals such as europium (Eu) and ytterbium (Yb); alloys containing any of these metals; and the like.

Note that in the case where the second electrode 104 is formed using an alkali metal, an alkaline-earth metal, or an alloy thereof, a vacuum evaporation method or a sputtering method can be used. Alternatively, in the case of using a silver paste or the like, a coating method, an inkjet method, or the like can be used Note that by proving the fifth layer 115, the second electrode 104 can be formed using any of a variety of conductive materials such as Al, Ag, ITO, and indium oxide-tin oxide containing silicon or silicon oxide regardless of the work functions. A film of such a conductive material can be formed by a sputtering method, an inkjet method, a spin coating method, or the like.

Further, as a formation method of the EL layer 103 in which the first layer (hole-inject layer) 111, the second layer (hole-transport layer) 112, the third layer (light-emitting layer) 113, the fourth layer (electron-transport layer) 114, and the fifth layer (electron-inject layer) 115 are in that order stacked, any of a variety of methods can be employed regardless of whether the method is a dry process or a wet process. For example, a vacuum evaporation method, an inkjet method, a spin coating method, or the like can be used. Note that a different formation method may be employed for each layer.

The second electrode 104 can also be formed by a wet process such as a sol-gel method using a paste of a metal material instead of a dry process such as a sputtering method or a vacuum evaporation method.

In the above-described light-emitting element of the present invention, a current flows because of a potential difference generated between the first electrode 102 and the second electrode 104 and holes and electrons recombine in the EL layer 103, so that light is emitted. Then, this emitted light is extracted out through one or both of the first electrode 102 and the second electrode 104. Accordingly, one or both of the first electrode 102 and the second electrode 104 is/are an electrode having a light-transmitting property.

Figure 2A:
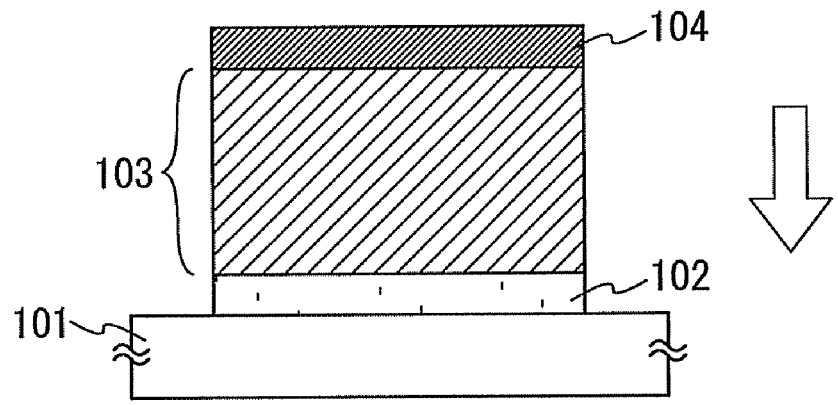
FIGS. 2A to 2C each illustrate an embodiment of light emission of a light-emitting element according to Embodiment 2.
Figure 2B:
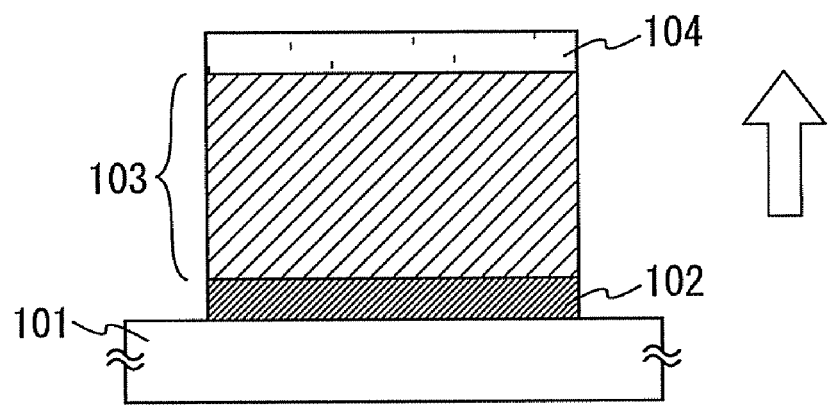
Figure 2C:
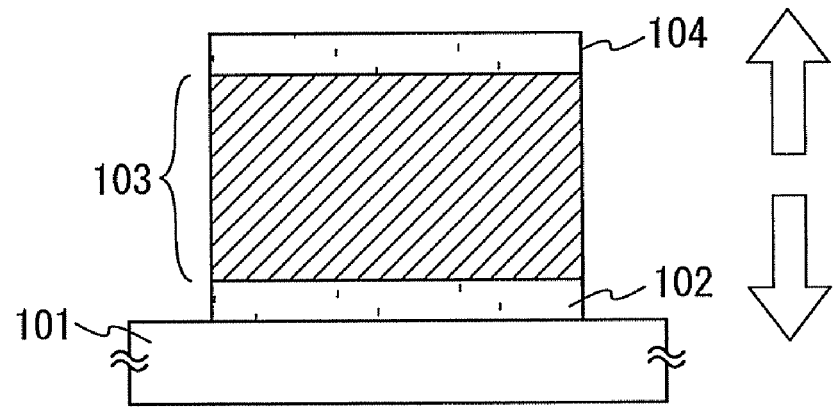

As illustrated in FIG. 2A, when only the first electrode 102 has a light-transmitting property, the emitted light is extracted from a substrate side through the first electrode 102. Alternatively, as illustrated in FIG. 2B, when only the second electrode 104 has a light-transmitting property, the emitted light is extracted from the side opposite to the substrate through the second electrode 104. As illustrated in FIG. 2C, when each of the first electrode 102 and the second electrode 104 has a light-transmitting property, the emitted light is extracted from both the substrate side and the side opposite to the substrate side through the first electrode 102 and the second electrode 104.

Note that the structure of the layers provided between the first electrode 102 and the second electrode 104 is not limited to the aforementioned one. Structures other than the above may be employed as long as at least the second layer 112 which is a hole-transport layer and the third layer 113 which is a light-emitting layer are included.

Alternatively, as illustrated in FIG. 1B, a structure may be employed in which the second electrode 104 functioning as a cathode, the EL layer 103, and the first electrode 102 functioning as an anode are stacked in that order over the substrate 101. Note that the EL layer 103 in this case has a structure in which the fifth layer 115, the fourth layer 114, the third layer 113, the second layer 112, the first layer 111, and the first electrode 102 are stacked in that order over the second electrode 104.

Note that by use of the light-emitting element of the present invention, a passive matrix light-emitting device or an active matrix light-emitting device in which drive of the light-emitting element is controlled by a thin film transistor (TFT) can be fabricated.

Note that there is no particular limitation on the structure of the TFT in the case of fabricating an active matrix light-emitting device. For example, a staggered TFT or an inverted staggered TFT can be used as appropriate. Further, a driver circuit formed over a TFT substrate may be formed using both of an n-type TFT and a p-type TFT or only either an n-type TFT or a p-type TFT. Furthermore, there is no particular limitation on the crystallinity of a semiconductor film used for the TFT. Either an amorphous semiconductor film or a crystalline semiconductor film may be used for the TFT.

Since the light-emitting elements described in Embodiment 2 have the third layer (light-emitting layer) 113 formed using any of the benzoxazole derivatives of the present invention which are bipolar substances, element efficiency of the light-emitting element, such as current efficiency, can be improved.

Note that in Embodiment 2, an appropriate combination of the structures described in Embodiment 1 can be used.

Embodiment 3

Figure 3:
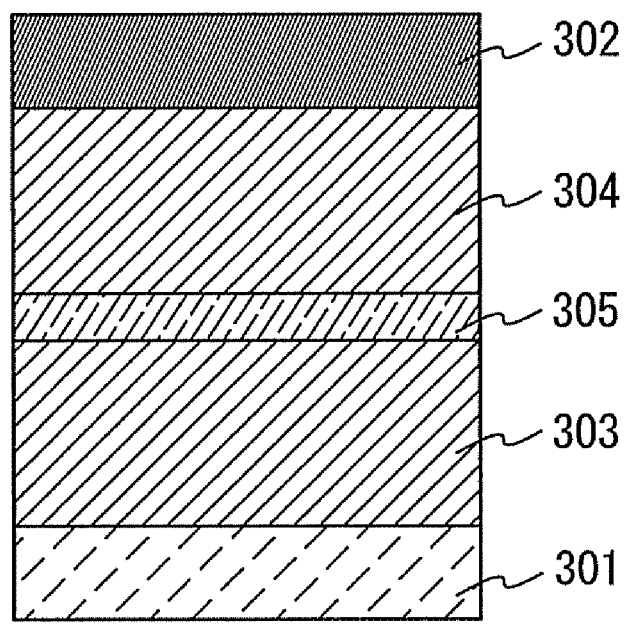
FIG. 3 illustrates a stack structure of a light-emitting element according to Embodiment 3.

In Embodiment 3, a light-emitting element having a stack of plural EL layers of the light-emitting elements described in Embodiment 2 (hereinafter, referred to as a stacked-type element) is described using FIG. 3. This light-emitting element is a stacked-type light-emitting element that has a plurality of EL layers (a first EL layer 303 and a second EL layer 304) between a first electrode 301 and a second electrode 302. Note that although a structure in which two EL layers are formed is described in Embodiment 3, three or more EL layers may be formed.

In Embodiment 3, the first electrode 301 functions as an anode, and the second electrode 302 functions as a cathode. Note that for the first electrode 301 and the second electrode 302, structures similar to those described in Embodiment 2 can be employed. Further, for the plurality of EL layers (the first EL layer 303 and the second EL layer 304), a structures similar to those described in Embodiment 2 can be employed. Note that structures of the first EL layer 303 and the second EL layer 304 may be the same or different from each other and can be similar to those described in Embodiment 2.

Further, a charge generation layer 305 is provided between the plurality of EL layers (the first EL layer 303 and the second EL layer 304). The charge generation layer 305 has a function of injecting electrons into one of the EL layers and injecting holes into the other of the EL layers when a voltage is applied to the first electrode 301 and the second electrode 302. In Embodiment 3, when a voltage is applied so that the potential of the first electrode 301 is higher than that of the second electrode 302, the charge generation layer 305 injects electrons into the first EL layer 303 and injects holes into the second EL layer 304.

Note that the charge generation layer 305 preferably has a light-transmitting property in terms of light extraction efficiency. Further, the charge generation layer 305 functions even when it has lower electric conductivity than the first electrode 301 or the second electrode 302.

The charge generation layer 305 may have either a structure in which an acceptor substance is added to a substance having a high hole-transport property or a structure in which a substance having a donor property is added to a substance having a high electron-transport property. Alternatively, both of these structures may be stacked.

In the case of the structure in which an acceptor substance is added to a substance having a high hole-transport property, examples of the substances having a high hole-transport property which can be used include aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluoren-2-yl)-N-phenylamino]-1,1'-biphenyl (abbreviation: BSPB), and the like. The substances described here are mainly materials having hole mobility of $10^{-6}$ cm$^2$/Vs or more. However, any substance other than the above substances may be used as long as it is a substance in which the hole-transport property is higher than the electron-transport property.

In addition, examples of the acceptor substance include 7,7,8,8-tetracyano-2,3,5,6-tetrafluoroquinodimethane (abbreviation: F$_4$-TCNQ) and chloranil and transition metal oxides. Other examples are oxides of metals belonging to Group 4 to Group 8 of the periodic table. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable because it is stable in air and its hygroscopic property is low so that it can be easily handled.

On the other hand, in the case of the structure in which a donor substance is added to a substance having a high electron-transport property, as the substance having a high electron-transport property, a metal complex having a quinoline skeleton or a benzoquinoline skeleton, such as tris(8-quinolinolato)aluminum (abbreviation: Alq), tris(4-methyl-8-quinolinolato)aluminum (abbreviation: Almq$_3$), bis(10-hydroxybenzo[h]-quinolinato)beryllium (abbreviation: BeBq$_2$), or bis(2-methyl-8-quinolinolato)(4-phenylphenolato)aluminum (abbreviation: BAlq), or the like can be used. Alternatively, a metal complex having an oxazole-based or thiazole-based ligand, such as bis[2-(2-hydroxyphenyl)benzoxazolato]zinc (abbreviation: $Zn(BOX)_2$) or bis[2-(2-hydroxyphenyl)-benzothiazolato]zinc (abbreviation: $Zn(BTZ)_2$), or the like can be used. Besides the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The substances described here are mainly materials having electron mobility of $10^{-6}$ $cm^2/Vs$ or more. Note that any substance other than the above substances may be used as long as it is a substance in which the electron-transport property is higher than the hole-transport property.

Further, as the donor substance, an alkali metal, an alkaline earth metal, a rare earth metal, a metal belonging to Group 13 of the periodic table, or an oxide or carbonate thereof can be used. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the donor substance.

Note that forming the charge generation layer 305 by using the above materials can suppress an increase in drive voltage caused by the stack of the EL layers.

In Embodiment 3, the light-emitting element having two EL layers is described. However, the present invention can be applied to a light-emitting element in which three or more EL layers are stacked, in a similar manner. As in the light-emitting element according to Embodiment 3, by arranging a plurality of EL layers between a pair of electrodes so that the plurality of EL layers can be partitioned by a charge generation layer, light emission in a high luminance region can be achieved with current density kept low; thus, a light-emitting element having long lifetime can be realized. Further, when the light-emitting element is applied to a lighting apparatus, voltage drop due to the resistance of the electrode materials can be suppressed; thus, uniform light emission in a large area can be achieved. Furthermore, a light-emitting device capable of low-voltage driving with low power consumption can be realized.

Further, by forming EL layers to emit light of different colors from each other, a light-emitting element as a whole can provide light emission of a desired color. For example, by forming a light-emitting element having two EL layers such that the emission color of the first EL layer and the emission color of the second EL layer are complementary colors, the light-emitting element can provide white light emission as a whole. Note that "complementary colors" refer to colors that can produce an achromatic color when mixed. In other words, when light emitted from substances that emit light of complementary colors is mixed, white light emission can be obtained.

Further, the same can be applied to a light-emitting element having three EL layers. For example, the light-emitting element as a whole can provide white light emission when the emission color of the first EL layer is red, the emission color of the second EL layer is green, and the emission color of the third EL layer is blue.

Note that in Embodiment 3, an appropriate combination of the structures described in Embodiments 1 and 2 can be used.

Embodiment 4

Figure 4A:
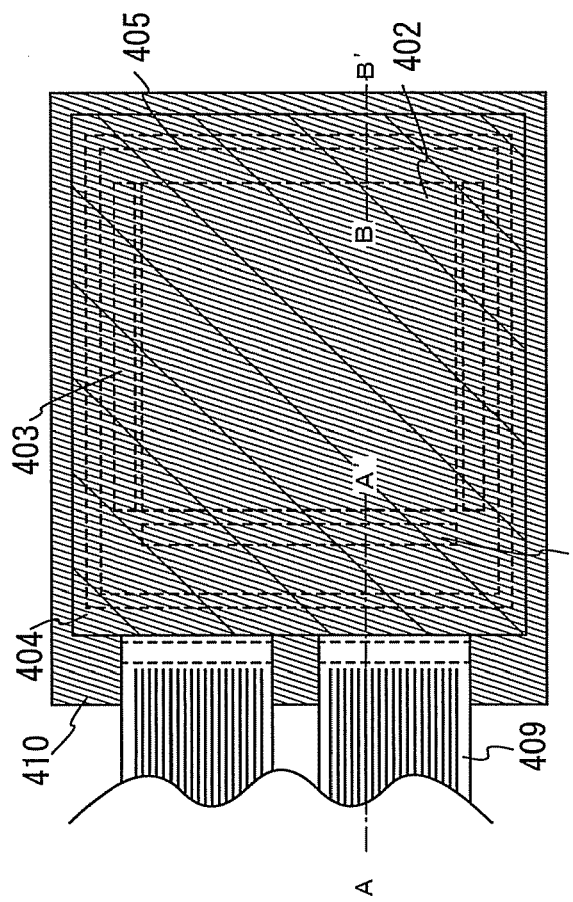
FIGS. 4A and 4B illustrate an active matrix light-emitting device according to Embodiment 4.
Figure 4B:
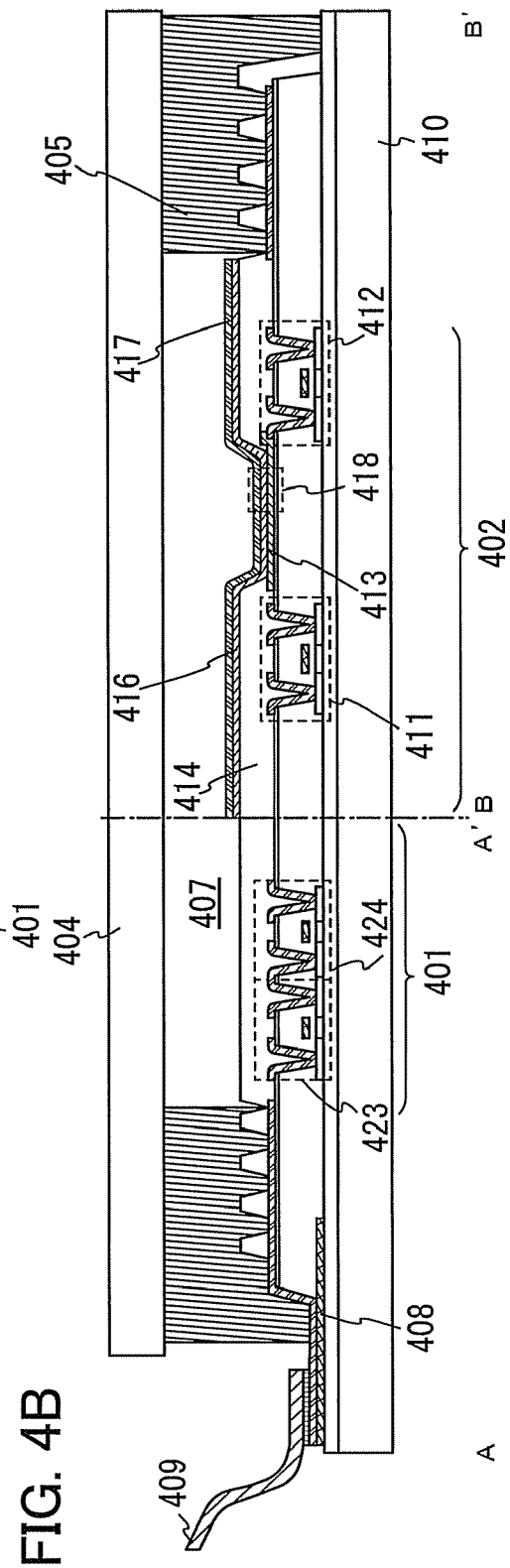

In Embodiment 4, a light-emitting device including a light-emitting element of the present invention in a pixel portion is described using FIGS. 4A and 4B. Note that FIG. 4A is a top view illustrating the light-emitting device and FIG. 4B is a cross-sectional view of FIG. 4A taken along lines A-A' and B-B'.

In FIG. 4A, reference numeral 401 denotes a driver circuit portion (a source side driver circuit), reference numeral 402 denotes a pixel portion, and reference numeral 403 denotes a driver circuit portion (a gate side driver circuit), which are shown by a dotted line. Further, reference numeral 404 denotes a sealing substrate, reference numeral 405 denotes a sealant, and reference numeral 407 denotes a space surrounded by the sealant 405.

Note that a leading wiring 408 is a wiring for transmitting signals that are input to the source side driver circuit 401 and the gate side driver circuit 403. The leading wiring 408 receives video signals, clock signals, start signals, reset signals, and the like from a flexible printed circuit (FPC) 409 serving as an external input terminal. Note that although only an FPC is illustrated here, this FPC may be provided with a printed wiring board (PWB). The light-emitting device in this specification includes not only a light-emitting device itself but also a light-emitting device to which an FPC or a PWB is attached.

Then, a cross-sectional structure is described using FIG. 4B. The driver circuit portions and the pixel portion are provided over an element substrate 410, but only the source side driver circuit 401 which is the driver circuit portion and one pixel of the pixel portion 402 are illustrated in FIG. 4B. Note that a CMOS circuit which is a combination of an n-channel TFT 423 and a p-channel TFT 424 is formed in the source side driver circuit 401. However, the driver circuit may be formed using a variety of circuits such as CMOS circuits, PMOS circuits, or NMOS circuits. Although a driver-integrated type in which a driver circuit is formed over the substrate is described in Embodiment 4, the present invention is not limited to this type, and the driver circuit can be formed outside the substrate.

The pixel portion 402 includes a plurality of pixels each having a switching TFT 411, a current controlling TFT 412, and a first electrode 413 which is electrically connected to a drain of the current controlling TFT 412. Note that an insulator 414 is formed to cover an end portion of the first electrode 413.

In order to improve the coverage, the insulator 414 is preferably provided such that either an upper end portion or a lower end portion of the insulator 414 has a curved surface with a curvature. For example, when positive photosensitive acrylic is used as a material for the insulator 414, only an upper end portion of the insulator 414 can have a curved surface with a radius of curvature (0.2 to 3 μm). Alternatively, the insulator 414 can be formed using either a negative type photosensitive material that becomes insoluble in an etchant by light irradiation or a positive type photosensitive material that becomes soluble in an etchant by light irradiation.

Over the first electrode 413, an EL layer 416 and a second electrode 417 are formed. Here, for a material used for the first electrode 413, any of a variety of metals, alloys, electrically conductive compounds, or mixtures thereof can be used. Note that as specific materials, the materials described in Embodiment 2 as a material that can be used for the first electrode can be used.

Further, the EL layer 416 is formed by various methods such as an evaporation method using an evaporation mask, an inkjet method, a spin coating method, or the like. The EL layer 416 has any of the structures described in Embodiment 2. Further, as another material included in the EL layer 416, any of low molecular compounds, high molecular compounds (including oligomers and dendrimers) may be used. The material used for the EL layer is not limited to an organic compound and may be an inorganic compound.

As the material used for the second electrode 417, any of a variety of metals, alloys, electrically conductive compounds, mixtures thereof, or the like can be used. Among such materials, a metal, an alloy, an electrically conductive compound, a mixture thereof, or the like having a low work function (a work function of 3.8 eV or less) is preferably used when the second electrode 417 is used as a cathode. For example, there are elements belonging to Group 1 and Group 2 of the periodic table, that is, alkali metals such as lithium (Li) and cesium (Cs), alkaline earth metals such as magnesium (Mg), calcium (Ca), and strontium (Sr), alloys thereof (e.g., MgAg and AlLi), and the like.

Note that when light from the EL layer 416 is transmitted through the second electrode 417, the second electrode 417 can be formed using a stack of a thin metal film with a small thickness and a transparent conductive film (indium oxide-tin oxide (ITO), indium oxide-tin oxide containing silicon or silicon oxide, indium oxide-zinc oxide (IZO), indium oxide containing tungsten oxide and zinc oxide, or the like).

Furthermore, by attaching the sealing substrate 404 and the element substrate 410 to each other with the sealant 405, a light-emitting element 418 is provided in the space 407 surrounded by the element substrate 410, the sealing substrate 404, and the sealant 405. Note that the space 407 may be filled with a filler. There are also the case where the space 407 is filled with an inert gas (such as nitrogen or argon) and the case where the space 407 is filled with the sealant 405.

Note that as the sealant 405, an epoxy-based resin is preferably used. In addition, it is preferable that such a material allows as little moisture or oxygen as possible to permeate. Further, as the sealing substrate 404, a plastic substrate made of fiberglass-reinforced plastics (FRP), poly(vinyl fluoride) (PVF), polyester, acrylic, or the like can be used instead of a glass substrate or a quartz substrate.

As described above, the active matrix light-emitting device having the light-emitting element of the present invention can be obtained.

Figure 5A:
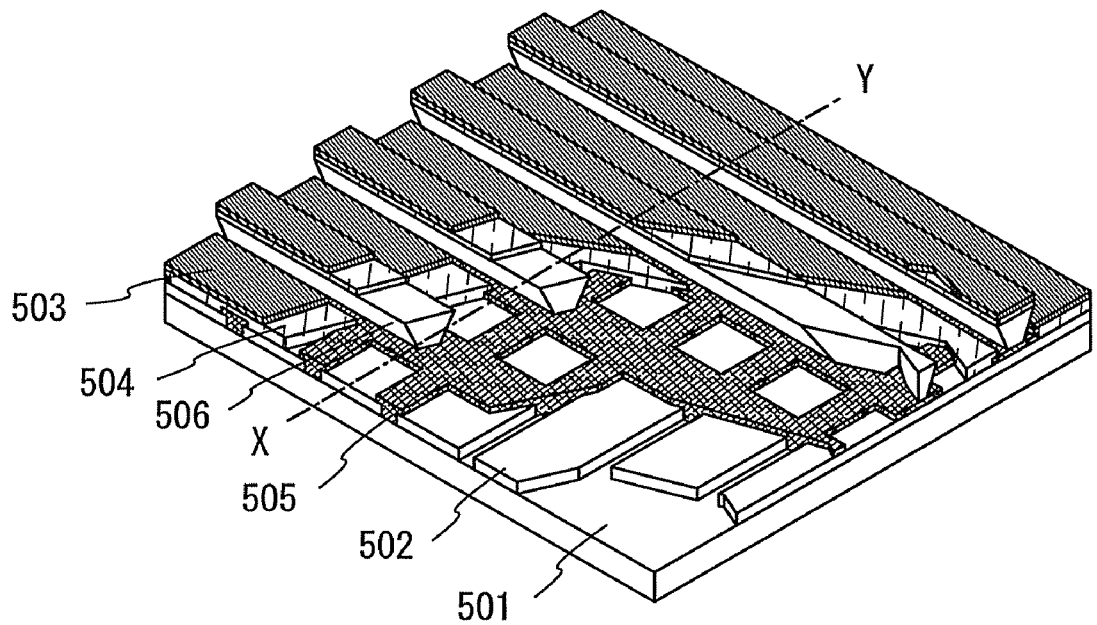
FIGS. 5A and 5B illustrate a passive matrix light-emitting device according to Embodiment 4.
Figure 5B:
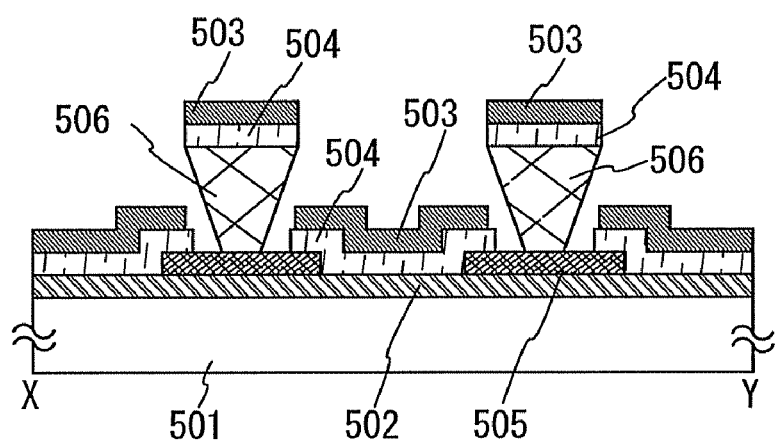

Further, the light-emitting element of the present invention can be used for a passive matrix light-emitting device instead of the above active matrix light-emitting device. FIGS. 5A and 5B illustrate a passive matrix light-emitting device using the light-emitting element of the present invention. Note that FIG. 5A is a perspective view of the light-emitting device and FIG. 5B is a cross-sectional view of FIG. 5A taken along a line X-Y.

In FIGS. 5A and 5B, an EL layer 504 is provided between a first electrode 502 and a second electrode 503 over a substrate 501. An end portion of the first electrode 502 is covered with an insulating layer 505. In addition, a partition layer 506 is provided over the insulating layer 505. The sidewalls of the partition layer 506 slope so that the distance between one sidewall and the other sidewall gradually decreases toward the surface of the substrate. In other words, a cross section taken along the direction of the short side of the partition layer 506 is trapezoidal, and the lower side (a side in contact with the insulating layer 505 which is one of a pair of parallel sides of the trapezoidal cross section) is shorter than the upper side (a side not in contact with the insulating layer 505 which is the other of the pair of parallel sides). By providing the partition layer 506 in such a manner, a defect of the light-emitting element due to static electricity or the like can be prevented.

Accordingly, the passive matrix light-emitting device having the light-emitting element of the present invention can be obtained.

Note that because of the use of the light-emitting element of the present invention which has high current efficiency, the light-emitting devices (the active matrix light-emitting device and the passive matrix light-emitting device) described in Embodiment 4 can be obtained as light-emitting devices having reduced power consumption.

Note that in Embodiment 4, an appropriate combination of the structures described in Embodiments 1 to 3 can be used.

Embodiment 5

In Embodiment 5, electronic devices including the light-emitting device of the present invention which is described in Embodiment 4 will be described. Examples of the electronic devices include cameras such as video cameras and digital cameras, goggle type displays, navigation systems, audio replay devices (e.g., car audio systems and audio systems), computers, game machines, portable information terminals (e.g., mobile computers, cellular phones, portable game machines, and electronic book readers), image replay devices in which a recording medium is provided (specifically, devices that are capable of replaying recording media such as digital versatile discs (DVDs) and equipped with a display device that can display an image), and the like. Specific examples of these electronic devices are illustrated in FIGS. 6A to 6D.

Figure 6A:
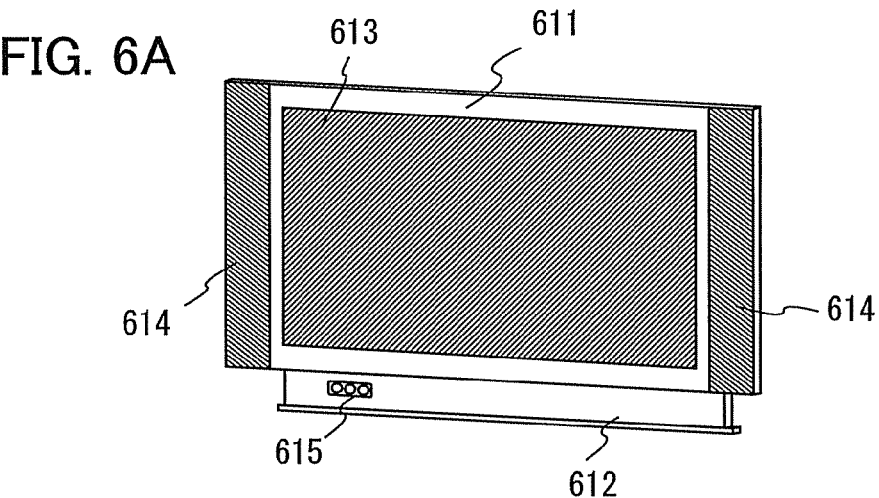
FIGS. 6A to 6D each illustrate an electronic device according to Embodiment 5.

FIG. 6A illustrates a television set according to the present invention, which includes a housing 611, a supporting base 612, a display portion 613, speaker portions 614, video input terminals 615, and the like. In this television set, the light-emitting device of the present invention can be applied to the display portion 613. A feature of the light-emitting device of the present invention is low driving voltage. Accordingly, by applying the light-emitting device of the present invention, a television set having reduced power consumption can be obtained.

Figure 6B:
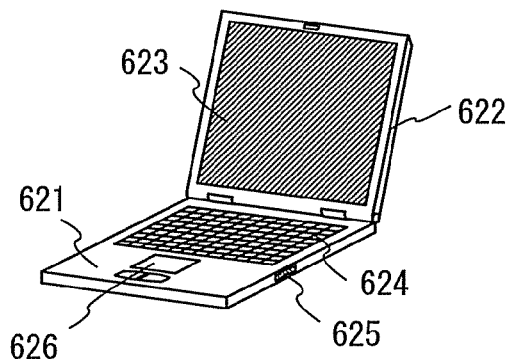

FIG. 6B illustrates a computer according to the present invention, which includes a main body 621, a housing 622, a display portion 623, a keyboard 624, an external connection port 625, a pointing device 626, and the like. In this computer, the light-emitting device of the present invention can be applied to the display portion 623. A feature of the light-emitting device of the present invention is low driving voltage. Accordingly, by applying the light-emitting device of the present invention, a computer having reduced power consumption can be obtained.

Figure 6C:
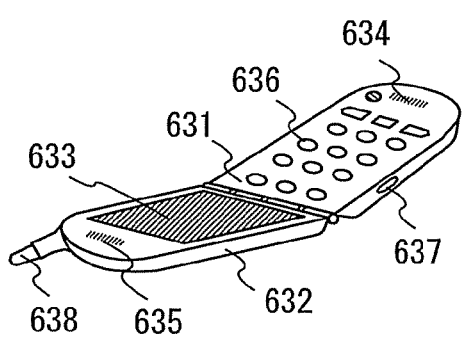

FIG. 6C illustrates a cellular phone according to the present invention, which includes a main body 631, a housing 632, a display portion 633, an audio input portion 634, an audio output portion 635, operation keys 636, an external connection port 637, an antenna 638, and the like. In this cellular phone, the light-emitting device of the present invention can be applied to the display portion 633. A feature of the light-emitting device of the present invention is low driving voltage. Accordingly, by applying the light-emitting device of the present invention, a cellular phone having reduced power consumption can be obtained.

Figure 6D:
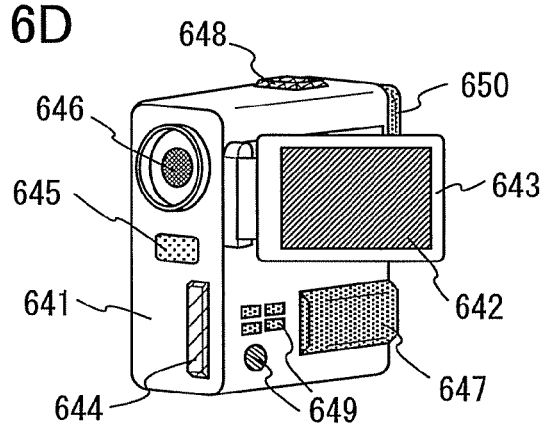

FIG. 6D illustrates a camera according to the present invention, which includes a main body 641, a display portion 642, a housing 643, an external connection port 644, a remote control receiving portion 645, an image receiving portion 646, a battery 647, an audio input portion 648, operation keys 649, an eyepiece portion 650, and the like. In this camera, the light-emitting device of the present invention can be applied to the display portion 642. A feature of the light-emitting device of the present invention is low driving voltage. Accordingly, by applying the light-emitting device of the present invention, a camera having reduced power consumption can be obtained.

As described above, the applicable range of the light-emitting device of the present invention is wide so that the light-emitting device can be applied to electronic devices in a wide variety of fields. By applying the light-emitting device of the present invention, an electronic device having reduced power consumption can be obtained.

Figure 7:
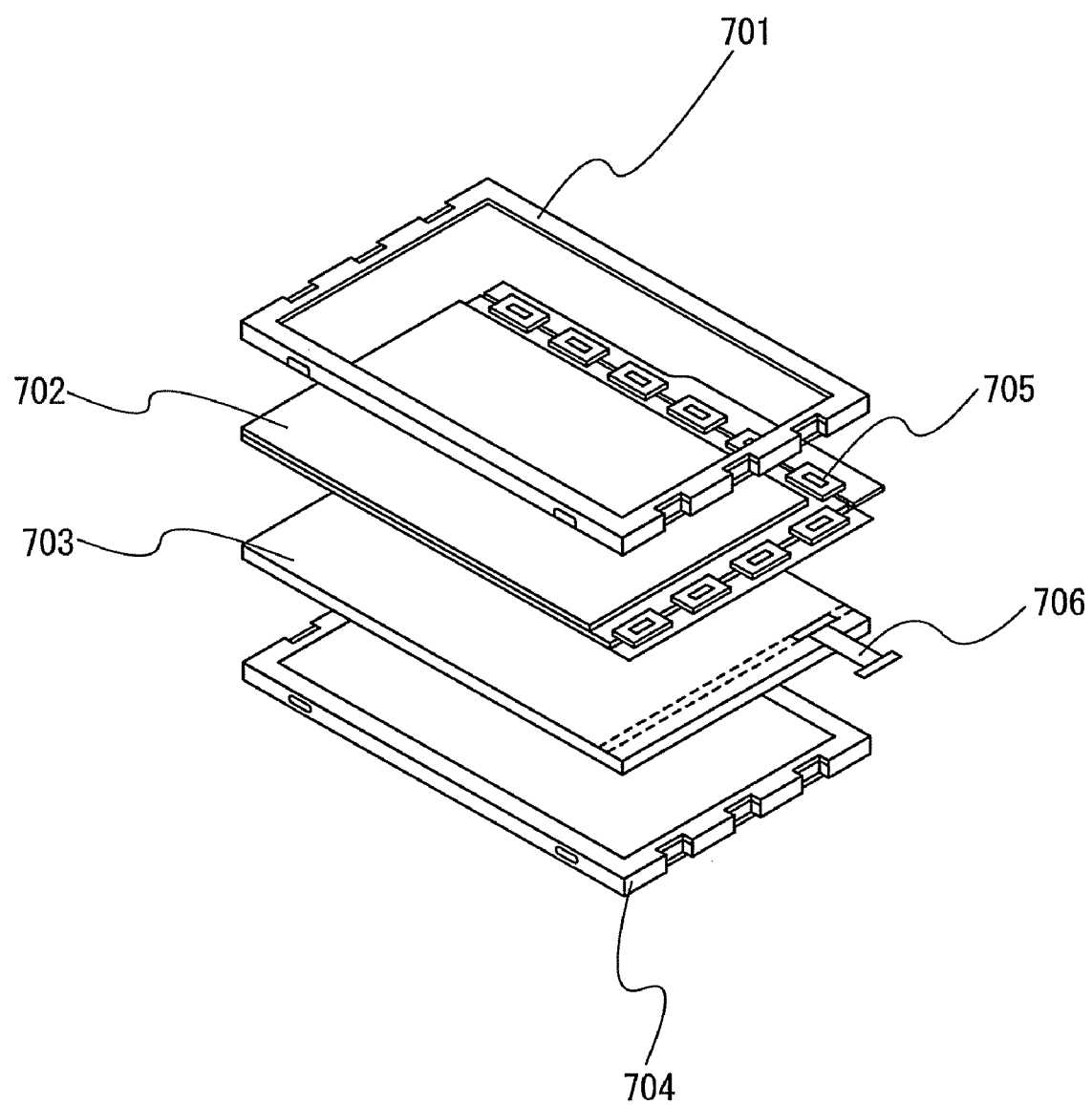
FIG. 7 illustrates a liquid crystal display device using a light-emitting device of the present invention as a backlight.

The light-emitting device of the present invention can also be used as a lighting apparatus. FIG. 7 is an example of a liquid crystal display device in which the light-emitting device of the present invention is used as a backlight. The liquid crystal display device illustrated in FIG. 7 includes a housing 701, a liquid crystal layer 702, a backlight 703, and a housing 704. The liquid crystal layer 702 is connected to a driver IC 705. The light-emitting device of the present invention is used for the backlight 703, and a current is supplied through a terminal 706.

By using the light-emitting device of the present invention as a backlight of a liquid crystal display device as described above, a backlight having low power consumption can be obtained. Further, since the light-emitting device of the present invention is a surface emitting lighting apparatus and can be formed to have a large area, a larger-area backlight can also be obtained. Accordingly, a larger-area liquid crystal display device having low power consumption can be obtained.

Figure 8:
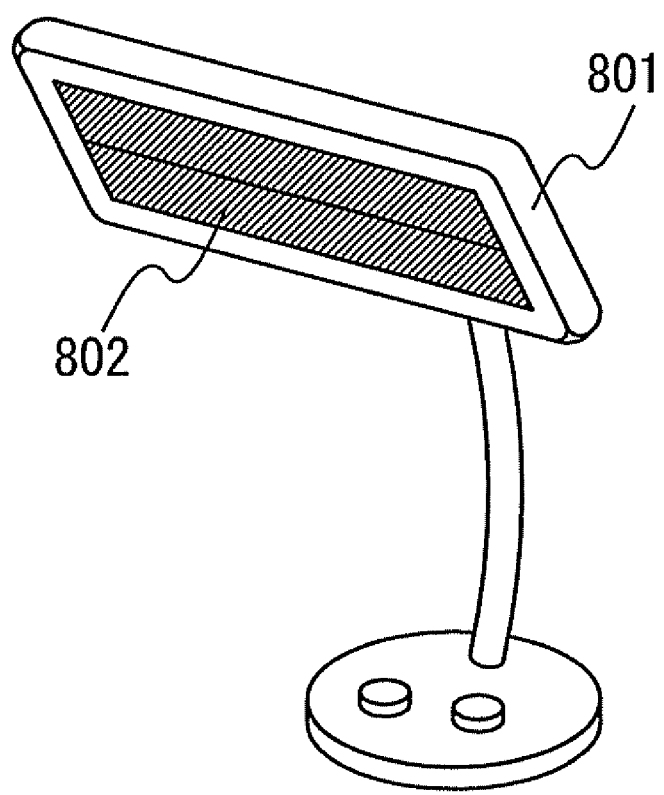
FIG. 8 illustrates a desk lamp using a light-emitting device of the present invention.

FIG. 8 illustrates an example in which a light-emitting device according to the present invention is used as a desk lamp, which is one of lighting apparatuses. The desk lamp illustrated in FIG. 8 has a housing 801 and a light source 802, and the light-emitting device of the present invention is used as the light source 802. Since light-emitting device of the present invention has the light-emitting element with low driving voltage, the desk lamp can have low power consumption.

Figure 9:
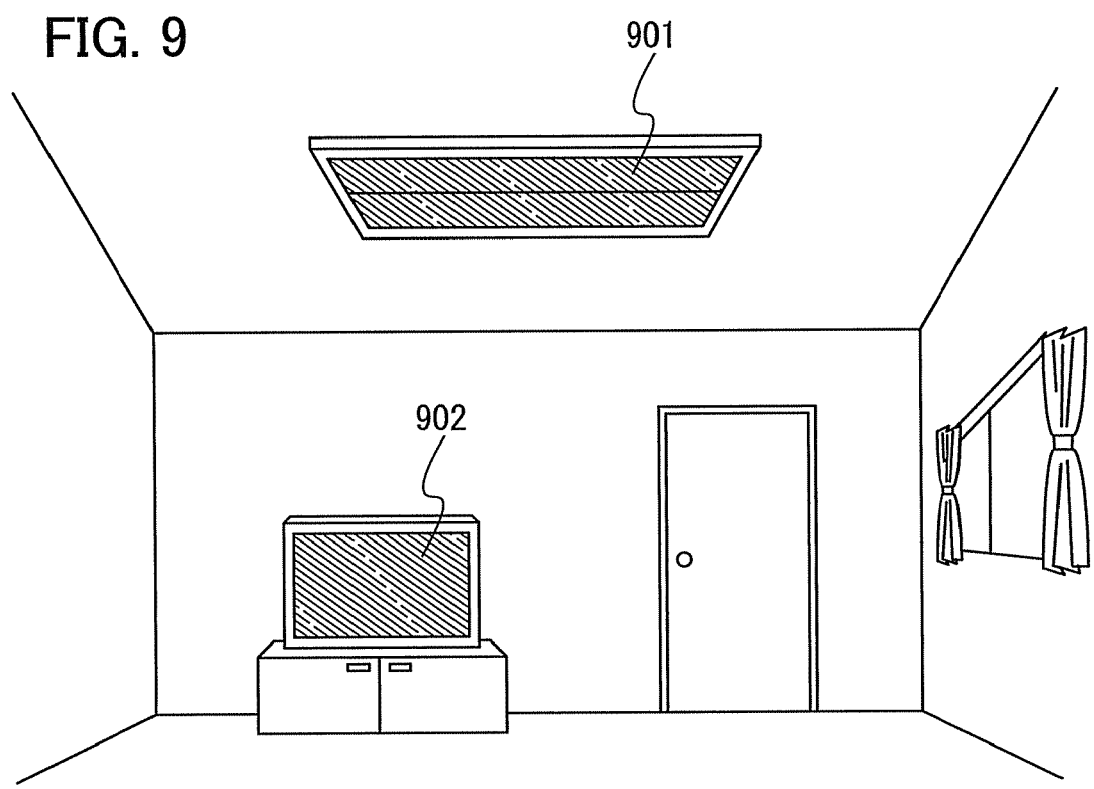
FIG. 9 illustrates an indoor lighting apparatus using a light-emitting device of the present invention.

FIG. 9 illustrates an example in which a light-emitting device to which the present invention is applied is used as an interior lighting apparatus 901. Since the light-emitting device of the present invention can also have a large area, the light-emitting device of the present invention can be used as a lighting apparatus having a large emission area. Since light-emitting device of the present invention has the light-emitting element with low driving voltage, the lighting apparatus can have low power consumption. In a room where a light-emitting device to which the present invention is applied is thus used as the interior lighting apparatus 901, a television set 902 according to the present invention as described with reference to FIG. 6A may be placed, so that public broadcasting or movies can be watched there.

Note that in Embodiment 5, an appropriate combination of the structures described in Embodiments 1 to 5 can be used.

Example 1

In Example 1, a method for synthesizing 9-[4-(benzoxazol-2-yl)phenyl]-9H-carbazole (abbreviation: CzBOx) represented by Structural Formula (100), which is one of the benzoxazole derivatives of the present invention, will be specifically described.

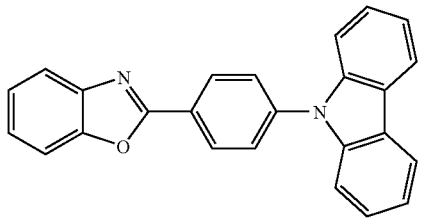

(100)

Step 1: Synthesis of 2-(4-Iodophenyl)benzoxazole (i) Synthesis of 4-Iodobenzochloride A synthesis scheme of 4-iodobenzoylchloride is illustrated in (D-1).

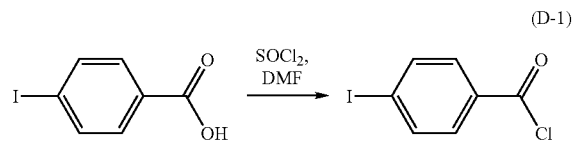

(D-1)

In a 200 mL three-neck flask were put 25 g (0.10 mmol) of 4-iodobenzoic acid, 70 mL of thionyl chloride, and 3 drops of N,N-dimethylformamide (DMF). This mixture was stirred under a nitrogen stream at 80° C. for 3 hours. After being stirred, the reaction solution was distilled under reduced pressure so that the thionyl chloride in the reaction solution was removed to give a light yellow oily substance.

(ii) Synthesis of 4-Iodo-N-(2-hydroxyphenyl)benzamide

A synthesis scheme of 4-iodo-N-(2-hydroxyphenyl)benzamide is illustrated in (D-2).

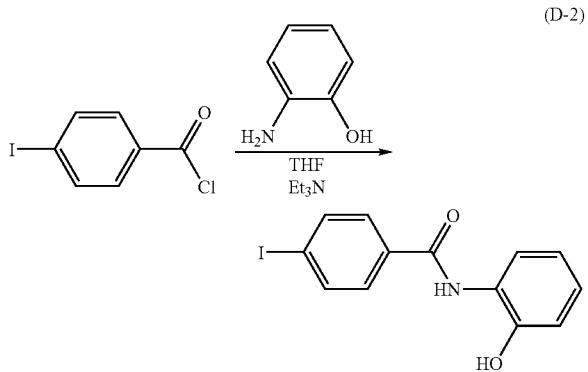

(D-2)

In a 300 mL three-neck flask were put 10 g (92 mmol) of 2-aminophenol, 7.0 mL of triethylamine, and 100 mL of tetrahydrofuran (THF). This solution was stirred at 0° C. for 20 minutes. Then, a mixed solution of 4-iodobenzoic acid chloride (0.10 mol) and 100 mL of tetrahydrofuran (abbreviation: THF) was dripped to the solution. This solution was stirred under a nitrogen stream at 0° C. for 5 hours. After that, about 300 mL of water was added to this solution, followed by extraction with ethyl acetate. Then, the organic layer and the extract were combined and washed with 1M hydrochloric acid, a saturated aqueous sodium hydrogen carbonate solution, and saturated brine in that order. After that, magnesium sulfate was added to the organic layer to dry it. Next, this mixture was suction filtered through Celite (produced by Wako Pure Chemical Industries, Ltd., Catalog No. 531-16855). The resulting filtrate was concentrated to give a solid. This solid was recrystallized with a mixed solvent of ethyl acetate and hexane to give 30 g of a white powdered solid in a yield of 97% through the two steps, Synthesis Schemes (D-1) and (D-2).

(iii) Synthesis of 2-(4-Iodophenyl)benzoxazole

A synthesis scheme of 2-(4-iodophenyl)benzoxazole is illustrated in (D-3).

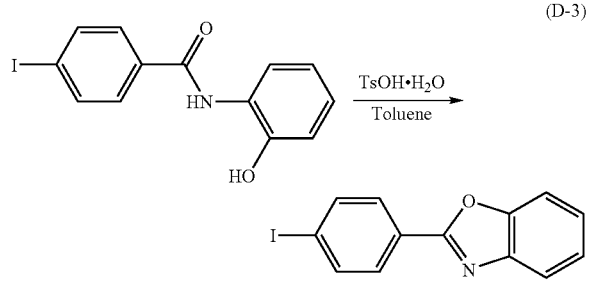

(D-3)

In a 300 mL three-neck flask were put 15 g (44 mmol) of 4-iodo-N-(2-hydroxyphenyl)benzamide and 24 g (0.14 mol) of para-toluenesulfonic acid monohydrate. The atmosphere in the flask was replaced with nitrogen. To this mixture was added 300 mL of toluene. The resulting mixture was stirred under a nitrogen stream at 110° C. for 4 hours. After that, this reaction mixture was added to about 300 mL of water, followed by extraction with ethyl acetate. Then, the organic layer and the extract were combined and washed with a saturated aqueous sodium hydrogen carbonate solution and saturated brine in that order. After that, magnesium sulfate was added to the organic layer to dry it. Next, this mixture was suction filtered through Celite. The resulting filtrate was concentrated to give a solid. This solid was recrystallized with a mixed solvent of ethyl acetate and hexane to give 11 g of a white solid in a yield of 75%.

Step 2: Synthesis of
9-[4-(Benzoxazol-2-yl)phenyl]-9H-carbazole
(abbreviation: CzBOx)

A synthesis scheme of 9-[4-(benzoxazol-2-yl)phenyl]-9H-carbazole (abbreviation: CzBOx) is illustrated in (D-4).

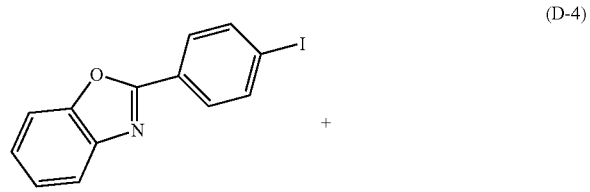

(D-4)

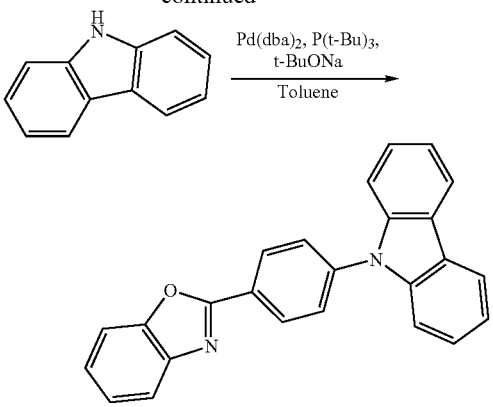

-continued

In a 100 mL three-neck flask were put 1.5 g (4.7 mmol) of 2-(4-iodophenyl)benzoxazole, 0.78 g (4.7 mmol) of 9H-carbazole, and 0.99 g (10 mmol) of sodium tert-butoxide. The atmosphere in the flask was replaced with nitrogen. To this mixture was added 15 mL of toluene. The resulting mixture was degassed under reduced pressure, and then the atmosphere in the flask was replaced with nitrogen. To this mixture were added 0.10 mL of a 10% hexane solution of tri(tert-butyl)phosphine and 0.030 g (0.48 mmol) of bis(dibenzylideneacetone)palladium(0). This mixture was stirred under a nitrogen stream at 110° C. for 11 hours. After that, toluene was added to this mixture, and this suspension was washed with 1M dilute hydrochloric acid, a saturated aqueous sodium hydrogen carbonate solution, and saturated brine in that order. After that, magnesium sulfate was added to the organic layer to dry it. Next, this mixture was suction filtered. The resulting filtrate was suction filtered through Celite (produced by Wako Pure Chemical Industries, Ltd., Catalog No. 531-16855). The resulting filtrate was concentrated, followed by purification by silica gel column chromatography. As developing solvents for the column chromatography, a mixed solvent of a 1:1 ratio of toluene to hexane, and then toluene were used. The fraction obtained was concentrated to give a solid. This solid was recrystallized with a mixed solvent of chloroform and methanol to give 1.5 g of a white powdered solid in a yield of 89%.

Sublimation purification of 1.5 g of the white solid obtained was performed by a train sublimation method. Under a reduced pressure of 7.0 Pa and with an argon flow rate of 4 mL/min, the sublimation purification was performed at 170° C. for 18 hours, whereby 1.1 g of the resulting substance was obtained in a yield of 72%.

The compound obtained through the above Step 2 was measured by a nuclear magnetic resonance (NMR) method. The following are the measurement data: $^1$H NMR (CDCl$_3$, 300 MHz): δ=7.29-7.55 (m, 8H), 7.61-7.67 (m, 1H), 7.74-7.85 (m, 3H), 8.16 (d, J=7.3 Hz, 2H), 8.51 (d, J=8.3 Hz, 2H)

Figure 11A:
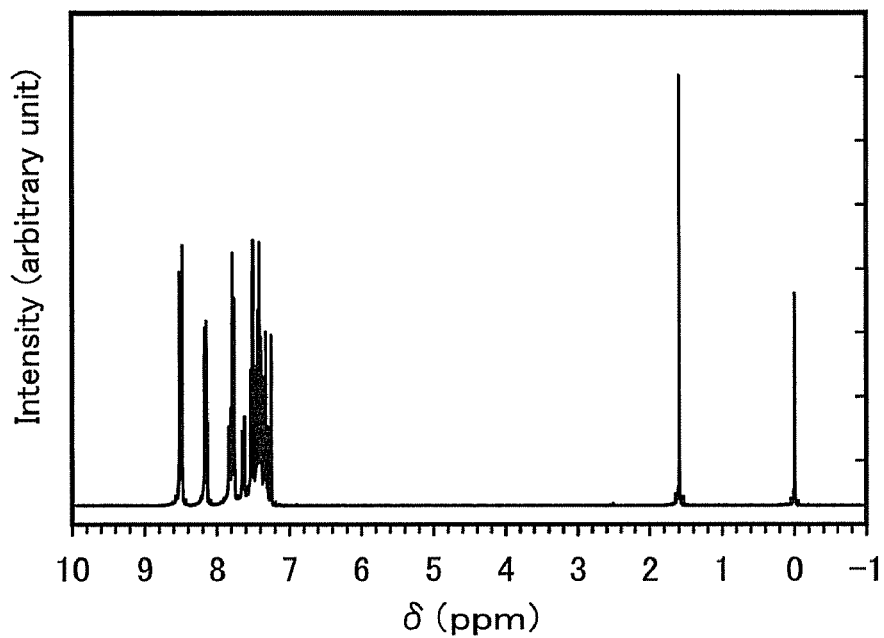
FIGS. 11A and 11B show NMR charts of CzBOx.
Figure 11B:
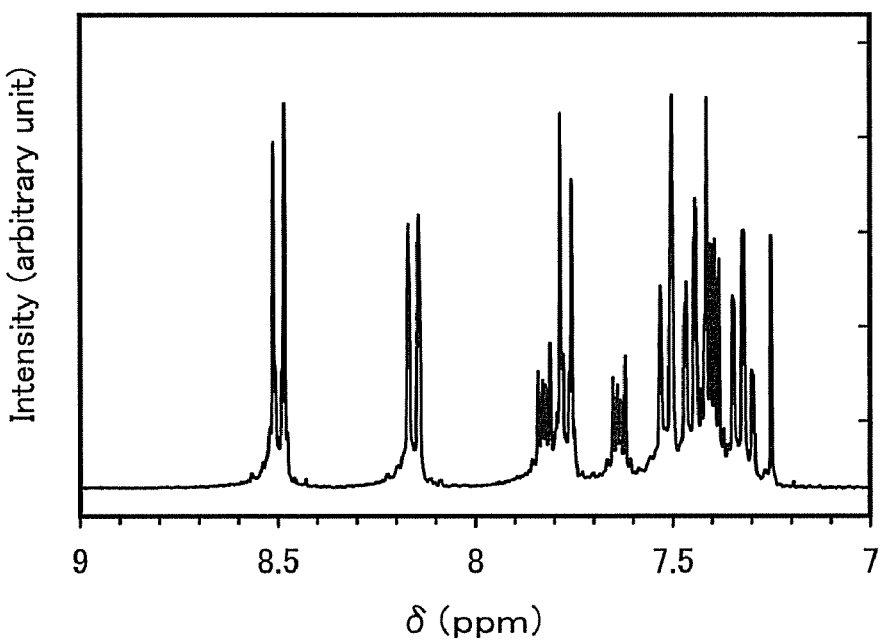

FIGS. 11A and 11B show $^1$H NMR charts. Note that FIG. 11B is a chart showing an enlarged part in the range of 7 ppm to 9 ppm of FIG. 11A. From the measurement results, it can be seen that 9-[4-(benzoxazol-2-yl)phenyl]-9H-carbazole (abbreviation: CzBOx) represented by the above Structural Formula (100), which is one of the benzoxazole derivatives of the present invention, is obtained.

Figure 12A:
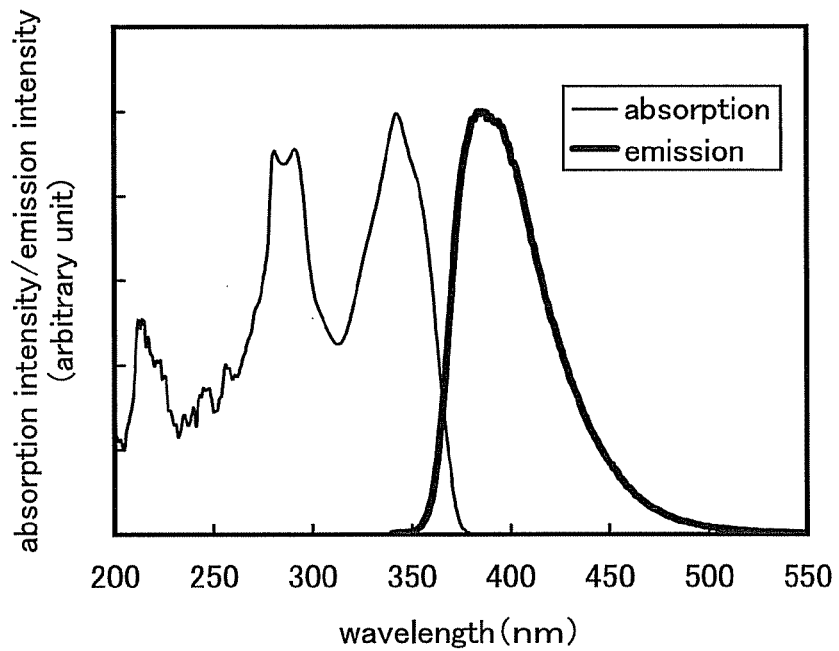
FIGS. 12A and 12B each show an absorption spectrum and an emission spectrum of CzBOx.
Figure 12B:
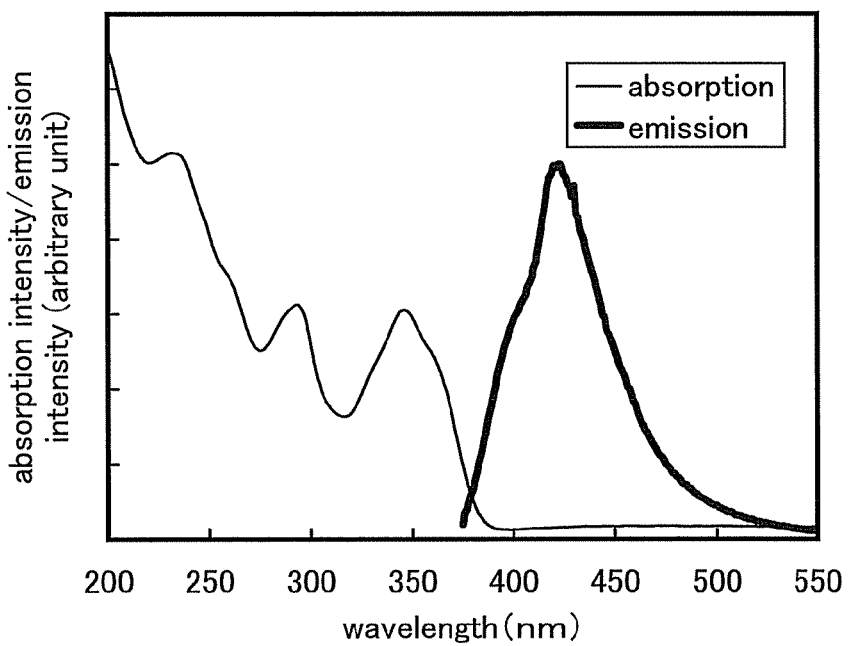

Further, FIG. 12A shows an absorption spectrum of a toluene solution of CzBOx, and FIG. 12B shows an absorption spectrum of a thin film of CzBOx. An ultraviolet-visible spectrophotometer (V-550, manufactured by JASCO Corporation) was used for the measurement. The absorption spectrum of the toluene solution of CzBOx was obtained by subtracting the absorption spectrum of quartz from the absorption spectrum of a quartz cell that includes the toluene solution. In addition, the absorption spectrum of the thin film of CzBOx was obtained by subtracting the absorption spectrum of quartz from the absorption spectrum of a sample formed by evaporating CzBOx to a quartz substrate.

In FIGS. 12A and 12B, the horizontal axis represents wavelength (nm) and the vertical axis represents absorption intensity (arbitrary unit). With the toluene solution, an absorption peak was observed at around 342 nm. With the thin film, an absorption peak was observed at around 346 nm. Further, FIG. 12A shows an emission spectrum of the toluene solution of CzBOx (an excitation wavelength of 333 nm). FIG. 12B shows an emission spectrum of the thin film of CzBOx (an excitation wavelength of 345 nm). In FIGS. 12A and 12B, the horizontal axis represents wavelength (nm) and the vertical axis also represents emission intensity (arbitrary unit). With the toluene solution, the maximum emission wavelength was 388 nm (an excitation wavelength of 333 nm). With the thin film, the maximum emission wavelength was 422 nm (an excitation wavelength of 345 nm).

Further, by measurement with a photoelectron spectrometer (AC-2, manufactured by Riken Keiki, Co., Ltd.) in the atmosphere, the ionization potential of the thin film of CzBOx was found to be 5.88 eV. As a result, it was understood that the HOMO level was −5.88 eV. Furthermore, with the use of the absorption spectrum data of the thin film of CzBOx, the absorption edge was obtained by a Tauc plot assuming direct transition. The absorption edge was estimated as an optical energy gap, whereby the energy gap was 3.30 eV. From the obtained values of the energy gap and HOMO level, the LUMO level was −2.58 eV.

Furthermore, the oxidation-reduction characteristics of CzBOx were measured by cyclic voltammetry (CV). Note that an electrochemical analyzer (ALS model 600A, manufactured by BAS Inc.) was used for the measurement.

For a solution used in the CV measurement, dehydrated dimethylformamide (DMF, produced by Sigma-Aldrich Inc., 99.8%, Catalog No. 22705-6) was used as a solvent, and tetra-n-butylammonium perchlorate (n-Bu$_4$NClO$_4$, produced by Tokyo Chemical Industry Co., Ltd., Catalog No. T0836), which was a supporting electrolyte, was dissolved in the solvent such that the concentration of tetra-n-butylammonium perchlorate was 100 mmol/L. Furthermore, CzBOx, which was the substance that is to be measured, was dissolved in the solution such that the concentration of CzBOx was 2 mmol/L. In addition, a platinum electrode (PTE platinum electrode, produced by BAS Inc.) was used as a working electrode, a platinum electrode (Pt counter electrode for VC-3, (5 cm), produced by BAS Inc.) was used as an auxiliary electrode, and an Ag/Ag$^+$ electrode (RE7 reference electrode for nonaqueous solvent, produced by BAS Inc.) was used as a reference electrode. Note that the measurement was conducted at room temperature.

The oxidation characteristics of CzBOx were examined by 100 cycles of the measurement in which a scan for changing the potential of the working electrode with respect to the reference electrode from −0.27 V to 1.20 V and then from 1.20 V to −0.27 V was set to one cycle. Further, reduction characteristics of CzBOx were examined by 100 cycles of the measurement in which a scan for changing the potential of the working electrode with respect to the reference electrode from −1.68 V to −2.45 V and then from −2.45 V to −1.68 V was set to one cycle. Note that the scan rate for the CV measurement was set to 0.1 V/s.

As a result, even after the 100 cycles of the measurement, significant changes in the peak position and peak intensity of the CV curves were not observed in the oxidation-reduction reactions. This demonstrates that CzBOx which is a benzoxazole derivative of the present invention is significantly stable against repetition of oxidation-reduction reactions.

Example 2

In Example 2, a method for synthesizing 9-[4'-(benzoxazol-2-yl)biphenyl-4-yl]-9H-carbazole (abbreviation: CzPBOx) represented by Structural Formula (200), which is one of the benzoxazole derivatives of the present invention, will be specifically described.

(200)

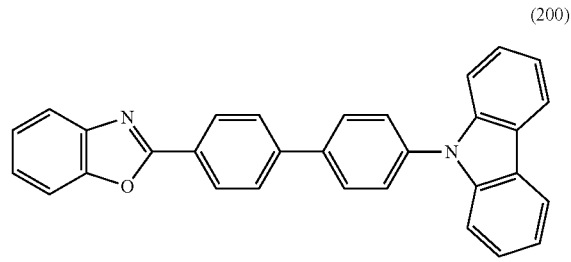

Step 1: Synthesis of 4-(9H-carbazol-9-yl)phenylboronic acid (i) Synthesis of 9-(4-Bromophenyl)-9H-carbazole A synthesis scheme of 9-(4-bromophenyl)-9H-carbazole is illustrated in (E-1).

(E-1)

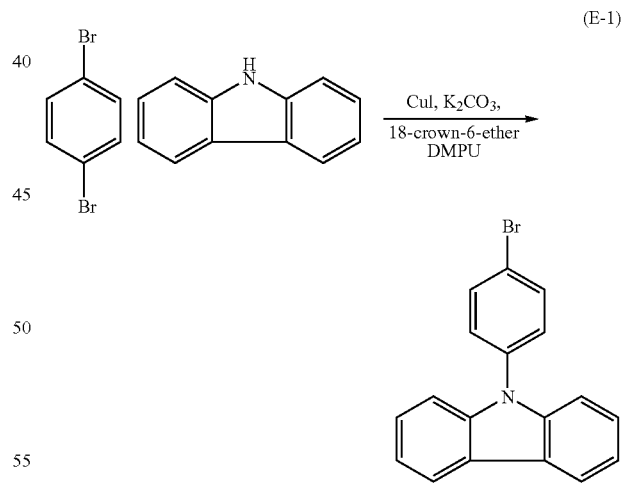

In a 300 mL three-neck flask were put 56 g (240 mmol) of 1,4-dibromobenzene, 31 g (180 mmol) of 9H-carabazole, 4.6 g (24 mmol) of copper(I) iodide, 2.1 g (8.0 mmol) of 18-crown-6-ether, 66 g (480 mmol) of potassium carbonate, and 8 mL of 1,3-dimethyl-3,4,5,6-tetrahydro-2(1H)pyrimidinone (abbreviation: DMPU). This mixture was stirred under a nitrogen stream at 180° C. for 6 hours. After that, this mixture was filtered. The resulting filtrate was washed with dilute hydrochloric acid, a saturated aqueous sodium hydrogen carbonate solution, and saturated brine in that order. The organic layer was dried with magnesium sulfate. This mixture was filtered. The resulting filtrate was concentrated to give a compound, which was then purified by silica gel column chromatography (the developing solvent was a mixed solvent of a 9:1 ratio of hexane to ethyl acetate). The fraction obtained was concentrated to give a compound. This compound was recrystallized with a mixed solvent of chloroform and hexane to give the desired substance as 21 g of a light brown plate-like crystal in a yield of 35%.

(ii) Synthesis of 4-(9H-carbazol-9-yl)phenylboronic acid

A synthesis scheme of 4-(9H-carbazol-9-yl)phenylboronic acid is illustrated in (E-2).

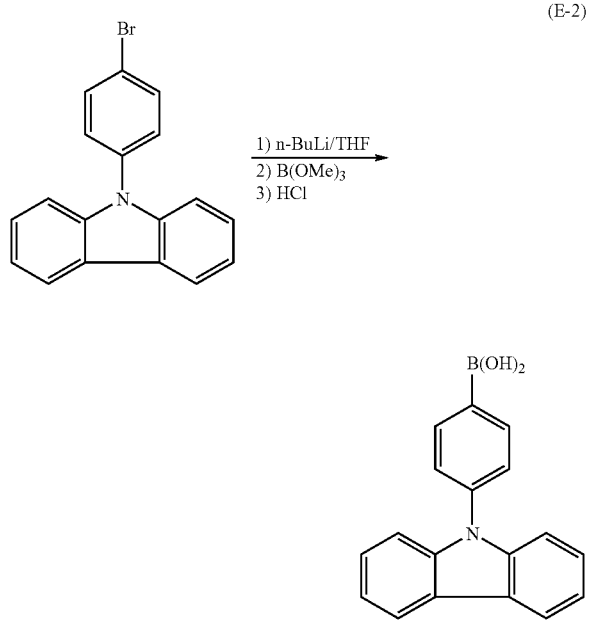

In a 500 mL three-neck flask was put 21.8 g (67.5 mmol) of 9-(4-bromophenyl)-9H-carbazole. The atmosphere in the flask was replaced with nitrogen. To the mixture was added 200 mL of tetrahydrofuran (THF). The temperature of this solution was set to −78° C., and then 48.9 mL (74.3 mmol) of n-butyllithium (a 1.52 mol/L hexane solution) was dripped to the solution. The mixture was stirred at the same temperature for 2 hours. After that, 17.4 mL (155 mmol) of trimethyl borate was added to the mixture, followed by stirring for 1 hour at the same temperature. Then, the mixture was stirred for 24 hours while the temperature thereof is returned to room temperature. After that, 200 mL of 1.0 mol/L hydrochloric acid was added to this solution, followed by stirring for 1 hour at room temperature. The organic layer of the mixture was washed with water, and the aqueous layer was extracted with ethyl acetate. The extract and the organic layer were combined, washed with saturated brine, and then dried with magnesium sulfate. After that, this mixture was suction filtered. The resulting filtrate was concentrated to give a residue. This residue was recrystallized with a mixed solvent of chloroform and hexane to give 4-(9H-carbazol-9-yl)phenylboronic acid which was the desired substance as 13 g of a white powdered solid in a yield of 66%.

Step 2: Synthesis of 9-[4'-(Benzoxazol-2-yl)biphenyl-4-yl]-9H-carbazole (abbreviation: CzPBOx)

A synthesis scheme of 9-[4'-(benzoxazol-2-yl)biphenyl-4-yl]-9H-carbazole (abbreviation: CzPBOx) is illustrated in (E-3).

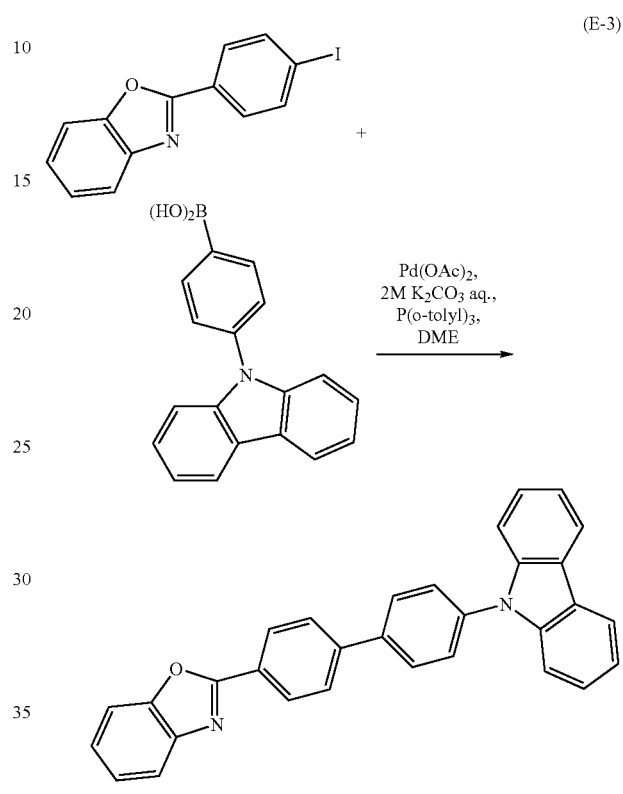

In a 100 mL three-neck flask were put 1.0 g (3.1 mmol) of 2-(4-iodophenyl)benzoxazole, 0.90 g (3.1 mmol) of 4-(9H-carbazol-9-yl)phenylboronic acid, and 0.067 g (0.22 mmol) of tri(ortho-tolyl)phosphine. To this mixture were added 30 mL of 1,2-dimethoxyethane (abbreviation: DME) and 30 mL of a 2M potassium carbonate aqueous solution. This mixture was degassed under reduced pressure, and then the atmosphere in the flask was replaced with nitrogen. To this mixture was added 7.0 mg (0.031 mmol) of palladium(II) acetate, and the resulting mixture was stirred at 90° C. for 5 hours while being heated. After that, toluene was added to this mixture, and the organic layer was washed with a saturated aqueous sodium carbonate solution and saturated brine in that order. After that, magnesium sulfate was added to the organic layer to dry it. Next, this mixture was suction filtered. The resulting filtrate was suction filtered through Celite (produced by Wako Pure Chemical Industries, Ltd., Catalog No. 531-16855). The resulting filtrate was concentrated, followed by purification by silica gel column chromatography. As a developing solvent for the chromatography, toluene was used. The fraction obtained was concentrated to give a solid. This solid was recrystallized with a mixed solvent of chloroform and methanol to give 1.2 g of a white powdered solid in a yield of 88%.

Sublimation purification of 1.2 g of the white solid obtained was performed by a train sublimation method. Under a reduced pressure of 7.0 Pa and with an argon flow rate of 4 mL/min, the sublimation purification was performed at 220° C. for 19 hours, whereby 1.1 g of the resulting substance was obtained in a yield of 90%.

The compound obtained through the above Step 2 was measured by a nuclear magnetic resonance (NMR) method. The following are the measurement data: $^1$H NMR (CDCl$_3$, 300 MHz): δ=7.27-7.52 (m, 8H), 7.59-7.64 (m, 1H), 7.69 (d, J=8.3 Hz, 2H), 7.79-7.92 (m, 5H), 8.17 (d, J=7.8 Hz, 2H), 8.40 (d, J=8.3 Hz, 2H)

Figure 13A:
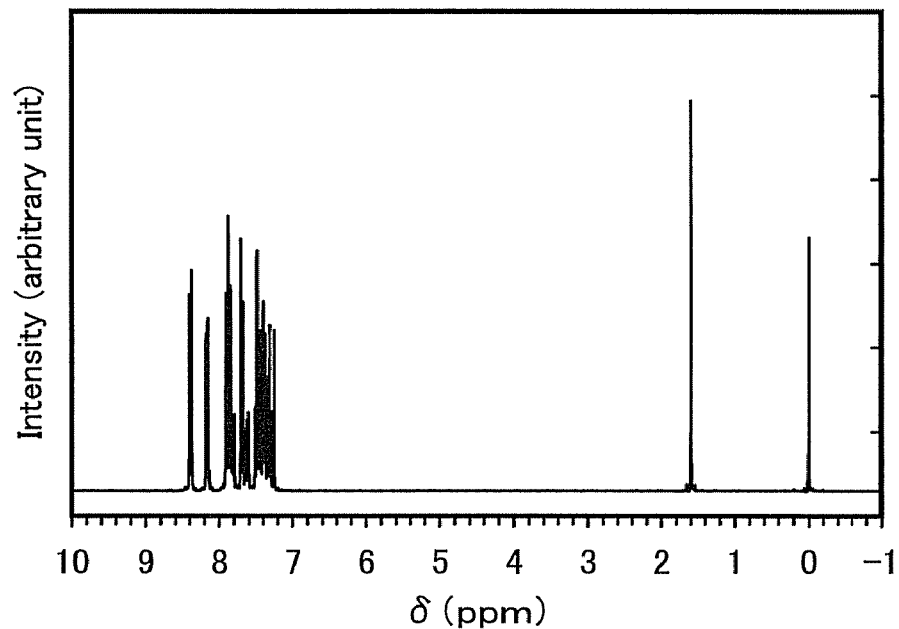
FIGS. 13A and 13B show NMR charts of CzPBOx.
Figure 13B:
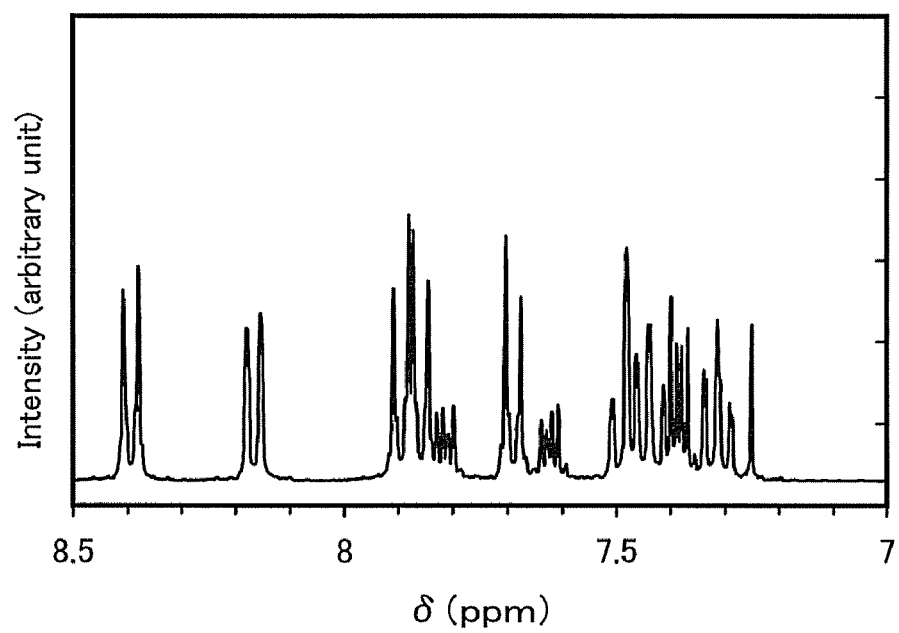

FIGS. 13A and 13B show $^1$H NMR charts. Note that FIG. 13B is a chart showing an enlarged part in the range of 7 ppm to 8.5 ppm of FIG. 13A. From the measurement results, it can be seen that 9-[4'-(benzoxazol-2-yl)biphenyl-4-yl]-9H-carbazole (abbreviation: CzPBOx) represented by the above Structural Formula (200), which is one of the benzoxazole derivatives of the present invention, is obtained.

Figure 14A:
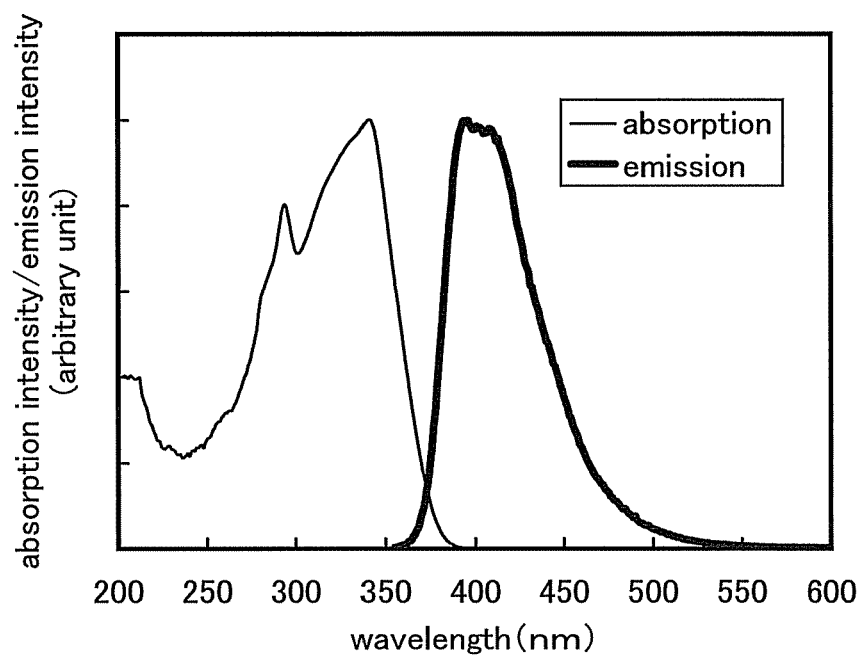
FIGS. 14A and 14B each show an absorption spectrum and an emission spectrum of CzPBOx.
Figure 14B:
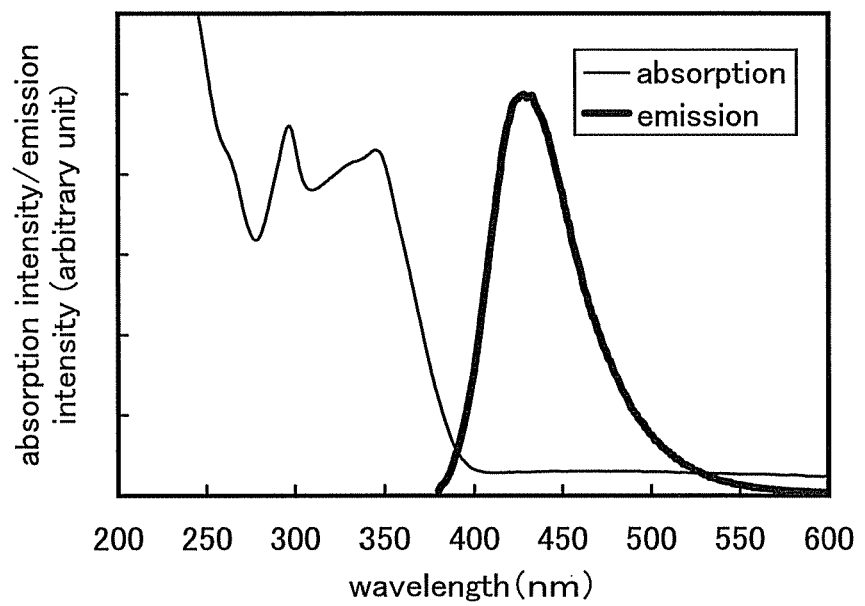

Further, FIG. 14A shows an absorption spectrum of a toluene solution of CzPBOx, and FIG. 14B shows an absorption spectrum of a thin film of CzPBOx. An ultraviolet-visible spectrophotometer (V-550, manufactured by JASCO Corporation) was used for the measurement. The absorption spectrum of the toluene solution of CzPBOx was obtained by subtracting the absorption spectrum of quartz from the absorption spectrum of a quartz cell that includes the toluene solution. In addition, the absorption spectrum of the thin film of CzPBOx was obtained by subtracting the absorption spectrum of quartz from the absorption spectrum of a sample formed by evaporating CzPBOx to a quartz substrate.

In FIGS. 14A and 14B, the horizontal axis represents wavelength (nm) and the vertical axis represents absorption intensity (arbitrary unit). With the toluene solution, an absorption peak was observed at around 339 nm. With the thin film, an absorption peak was observed at around 345 nm. Further, FIG. 14A shows an emission spectrum of the toluene solution of CzPBOx (an excitation wavelength of 345 nm). FIG. 14B shows an emission spectrum of the thin film of CzPBOx (an excitation wavelength of 363 nm). In FIGS. 14A and 14B, the horizontal axis represents wavelength (nm) and the vertical axis also represents emission intensity (arbitrary unit). With the toluene solution, the maximum emission wavelength was 397 nm (an excitation wavelength of 345 nm). With the thin film, the maximum emission wavelength was 428 nm (an excitation wavelength of 363 nm).

Further, by measurement with a photoelectron spectrometer (AC-2, manufactured by Riken Keiki, Co., Ltd.) in the atmosphere, the ionization potential of the thin film of CzPBOx was found to be 5.76 eV. As a result, it was understood that the HOMO level was −5.79 eV. Furthermore, with the use of the absorption spectrum data of the thin film of CzPBOx, the absorption edge was obtained by a Tauc plot assuming direct transition. The absorption edge was estimated as an optical energy gap, whereby the energy gap was 3.32 eV. From the obtained values of the energy gap and HOMO level, the LUMO level was −2.44 eV.

Furthermore, the oxidation-reduction characteristics of CzPBOx were measured in a manner similar to that of Example 1. Specifically, the oxidation characteristics were examined by 100 cycles of the measurement in which a scan for changing the potential of the working electrode with respect to the reference electrode from 1.10 V to 0.20 V and then from 0.20 V to 1.10 V was set to one cycle. Further, the reduction characteristics were examined by 100 cycles of the measurement in which a scan for changing the potential of the working electrode with respect to the reference electrode from −1.39 V to −2.35 V and then from −2.35 V to −1.39 V was set to one cycle. Note that the scan rate for the CV measurement was set to 0.1 V/s.

As a result, even after the 100 cycles of the measurement, significant changes in the peak position and peak intensity of the CV curves were not observed in the oxidation-reduction reactions. This demonstrates that CzPBOx which is a benzoxazole derivative of the present invention is significantly stable against repetition of oxidation-reduction reactions.

Example 3

In Example 3, a method for forming a light-emitting element including the benzoxazole derivative described in Embodiment 1 as a host material of a light-emitting layer and measurement results of the element characteristics will be described. Specifically, Light-Emitting Element 1 formed using 9-[4-(benzoxazol-2-yl)phenyl]-9H-carbazole (abbreviation: CzBOx) described in Example 1 and Light-Emitting Element 2 formed using 9-[4'-(benzoxazol-2-yl)biphenyl-4-yl]-9H-carbazole (abbreviation: CzPBOx) described in Example 2 will be described.

Figure 10:
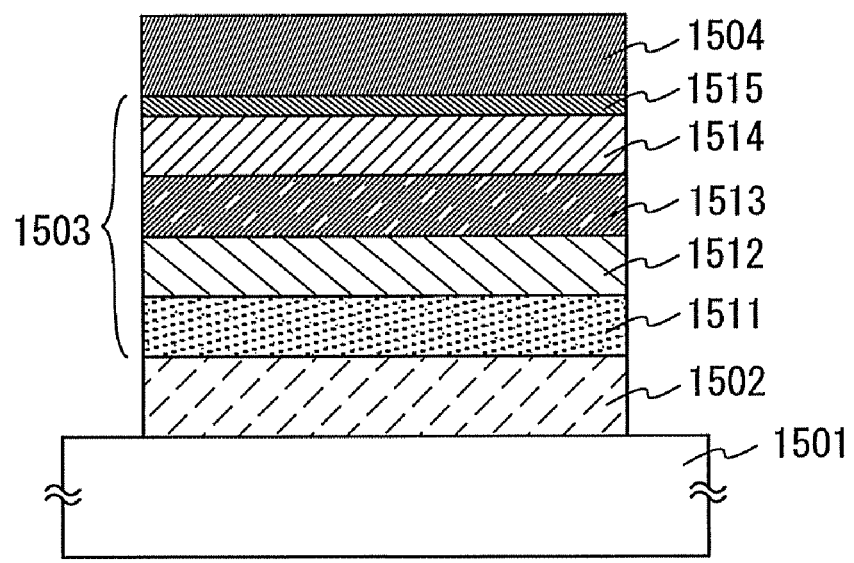
FIG. 10 illustrates an element structure of a light-emitting element according to Example 3.

Note that each element structure of the light-emitting elements of Example 3 is illustrated in FIG. 10, in which a light-emitting layer 1513 is formed using the above carbazole derivative of the present invention. Structural Formulae of organic compounds used in Example 3 are illustrated below.

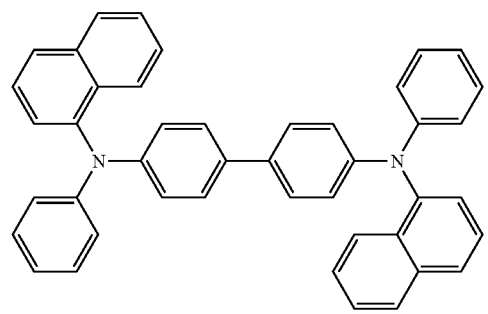

NPB

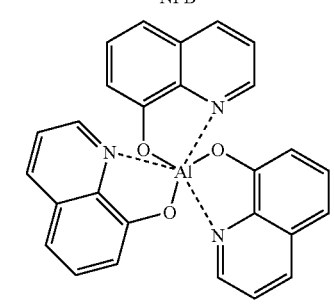

Alq

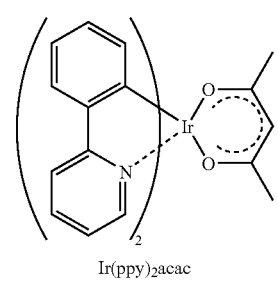

Ir(ppy)$_2$acac

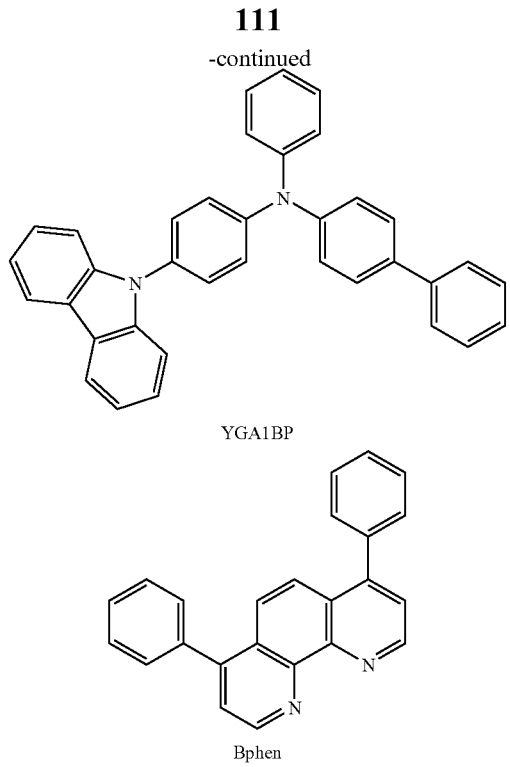

YGA1BP

Bphen

First, indium oxide-tin oxide containing silicon oxide was deposited on a substrate 1501 which is a glass substrate by a sputtering method to form a first electrode 1502. Note that the thickness of the first electrode 1502 was set to 110 nm and the area of the electrode was set to 2 mm×2 mm.

Next, an EL layer 1503 including a stack of a plurality of layers is formed over the first electrode 1502. In Example 3, the EL layer 1503 has a structure in which the first layer 1511 which is a hole-inject layer, the second layer 1512 which is a hole-transport layer, the third layer 1513 which is a light-emitting layer, a fourth layer 1514 which is an electron-transport layer, and a fifth layer 1515 which is an electron-inject layer are stacked in that order.

The substrate 1501 provided with the first electrode 1502 was fixed on a substrate holder that was provided in a vacuum evaporation apparatus so that a surface provided with the first electrode 1502 faced downward. The pressure in the vacuum evaporation apparatus was reduced to approximately $10^{-4}$ Pa. Then, on the first electrode 1502, 4,4'-bis[N-(1-naphthyl)-N-phenylamino]biphenyl (abbreviation: NPB) and molybdenum(VI) oxide were co-evaporated to form the first layer 1511 which was a hole-inject layer. The thickness of the first layer 1511 was set to 40 nm, and the evaporation rate was controlled so that the mass ratio of NPB to molybdenum(VI) oxide was 4:1 (=NPB:molybdenum oxide). Note that a co-evaporation method refers to an evaporation method by which evaporation is conducted from a plurality of evaporation sources at the same time in one treatment chamber.

Next, a 20-nm-thick film of a hole-transport material was formed on the first layer 1511 by an evaporation method with resistance heating to form the second layer 1512 which was a hole-transport layer. Note that for the second layer 1512, 4-(9H-carbazol-9-yl)-4'-phenyltriphenylamine (abbreviation: YGA1BP) was used.

Next, the third layer 1513 which was a light-emitting layer was formed on the second layer 1512 by an evaporation method with resistance heating. As the third layer 1513 of Light-Emitting Element 1, 9-[4-(benzoxazol-2-yl)phenyl]-9H-carbazole (abbreviation: CzBOx) and bis(2-phenylpyridinato-N,$C^{2'}$)iridium(III) acetylacetonato (abbreviation: Ir(ppy)$_2$acac) were co-evaporated to form a 40-nm-thick film. Here, the evaporation rate was controlled so that the mass ratio of CzBOx to Ir(ppy)$_2$acac was 1:0.06 (=CzBOx:Ir(ppy)$_2$acac). Further, as the third layer 1513 of Light-Emitting Element 2, 9-[4'-(benzoxazol-2-yl)biphenyl-4-yl]-9H-carbazole (abbreviation: CzPBOx) and bis(2-phenylpyridinato-N,$C^{2'}$)iridium(III) acetylacetonato (abbreviation: Ir(ppy)$_2$acac) were co-evaporated to form a 40-nm-thick film. Here, the evaporation rate was controlled so that the mass ratio of CzPBOx to Ir(ppy)$_2$acac was 1:0.06 (=CzPBOx:Ir(ppy)$_2$acac).

Furthermore, on the third layer 1513, a 10-nm-thick film of tris(8-quinolinolato)aluminum(III) (abbreviation: Alq) and, thereon, a 20-nm-thick film of bathophenanthroline (abbreviation: BPhen) were formed by an evaporation method with resistive heating to form the fourth layer 1514 which was an electron-transport layer.

On the fourth layer 1514, a 1-nm-thick film of lithium fluoride (LiF) was formed as the fifth layer 1515 which was an electron-inject layer.

Lastly, a 200-nm-thick film of aluminum was formed by an evaporation method with resistance heating to form the second electrode 1504. Thus, Light-Emitting Elements 1 and 2 were formed.

The thus obtained Light-Emitting Elements 1 and 2 were sealed in a glove box containing a nitrogen atmosphere so as not to be exposed to air. Then, operation characteristics of these light-emitting elements were measured. Note that the measurement was carried out at room temperature (in the atmosphere kept at 25° C.).

Figure 15:
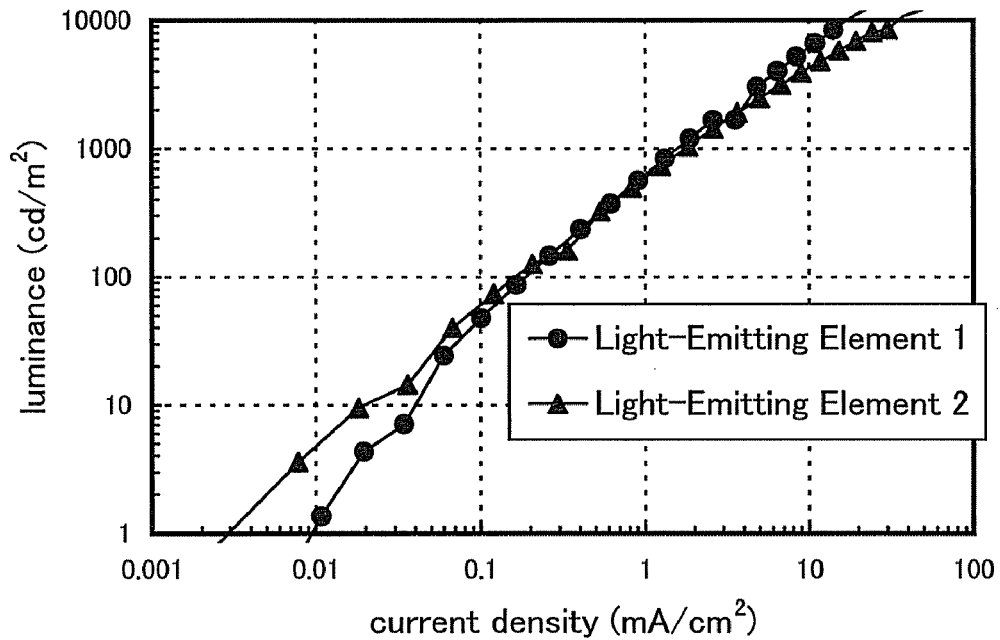
FIG. 15 shows current density vs. luminance characteristics of Light-Emitting Element 1 and Light-Emitting Element 2.
Figure 16:
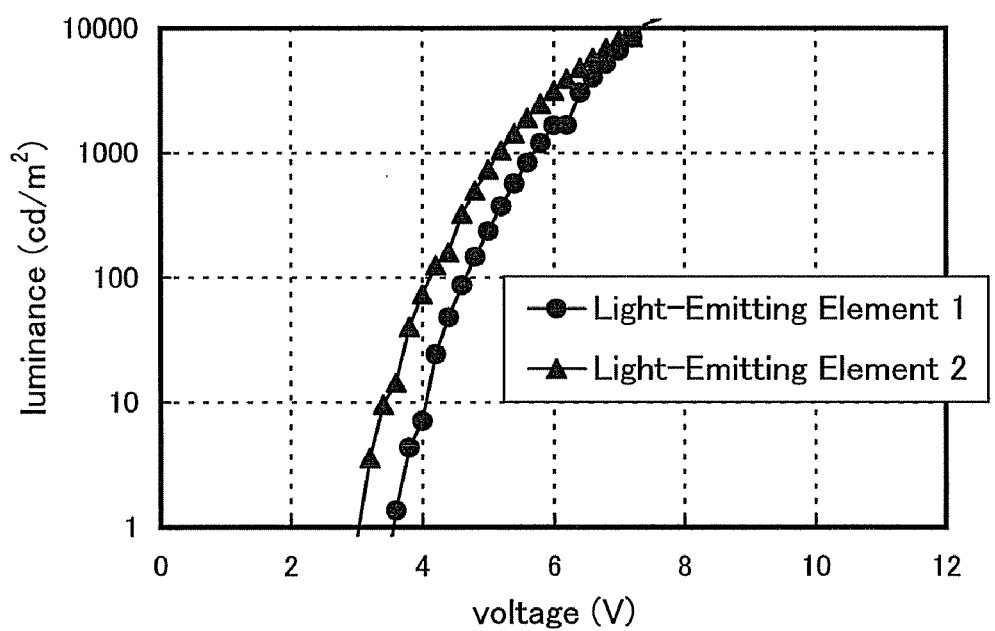
FIG. 16 shows voltage vs. luminance characteristics of Light-Emitting Element 1 and Light-Emitting Element 2.
Figure 17:
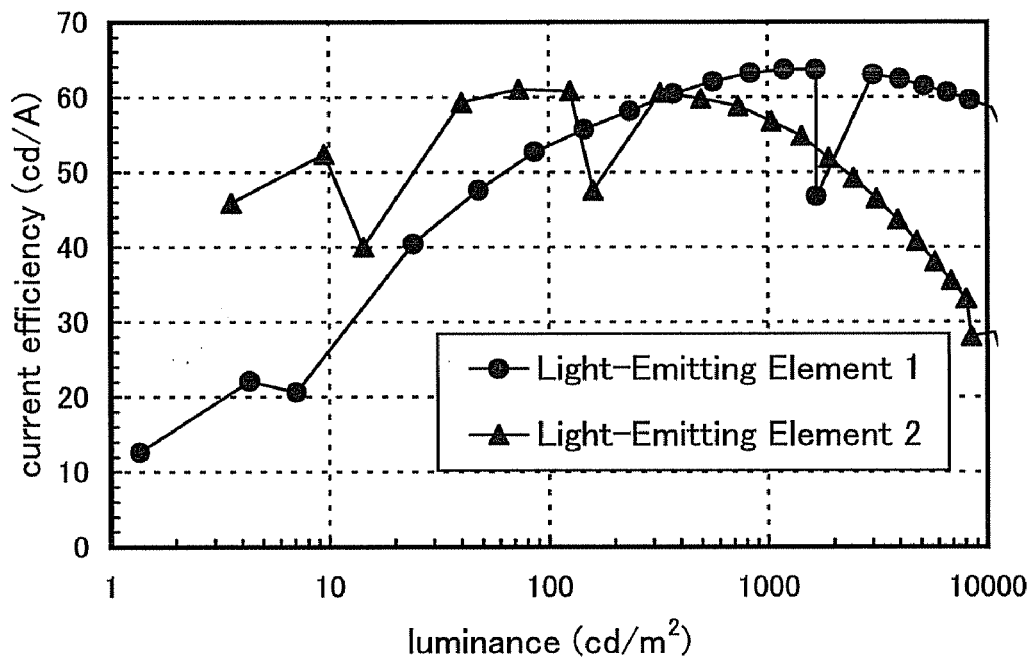
FIG. 17 shows luminance vs. current efficiency characteristics of Light-Emitting Element 1 and Light-Emitting Element 2.

FIG. 15 shows current density vs. luminance characteristics of Light-Emitting Elements 1 and 2. FIG. 16 shows voltage vs. luminance characteristics of Light-Emitting Elements 1 and 2. FIG. 17 shows luminance vs. current efficiency characteristics of Light-Emitting Elements 1 and 2. In FIG. 15, the vertical axis represents luminance (cd/m$^2$) and the horizontal axis represents current density (mA/cm$^2$). In FIG. 16, the vertical axis represents luminance (cd/m$^2$) and the horizontal axis represents voltage (V). In FIG. 17, the vertical axis represents current efficiency (cd/A) and the horizontal axis represents luminance (cd/m$^2$).

From FIG. 17, the maximum current efficiency of Light-Emitting Element 1 is 64 cd/A, and the maximum current efficiency of Light-Emitting Element 2 is 61 cd/A. This demonstrates that the light-emitting elements including the benzoxazole derivatives of the present invention have extremely high efficiency.

Figure 18:
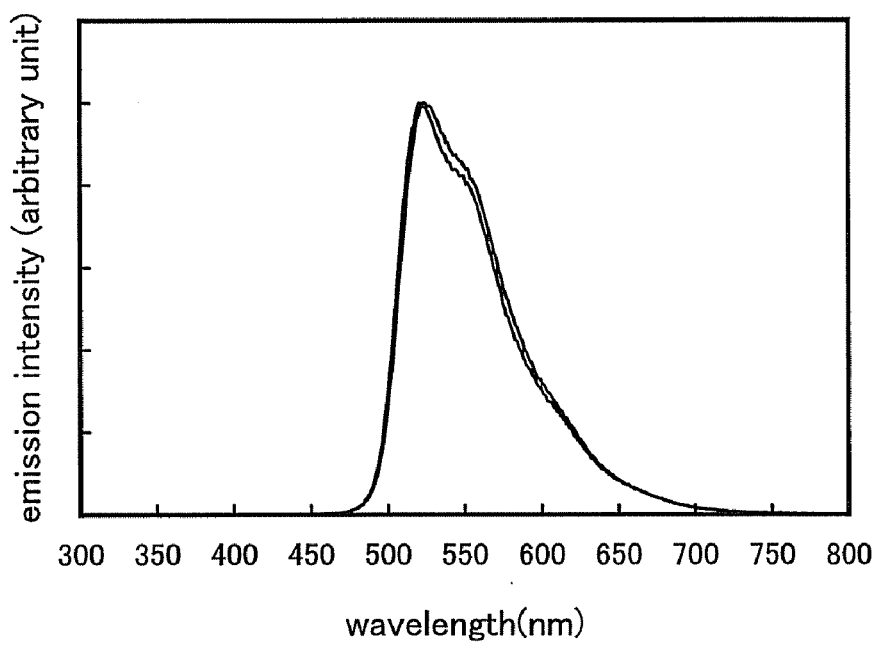
FIG. 18 shows emission spectra of Light-Emitting Element 1 and Light-Emitting Element 2.

FIG. 18 shows emission spectra of Light-Emitting Elements 1 and 2. As shown in FIG. 18, in each case of Light-Emitting Elements 1 and 2, an emission wavelength provided by Ir(ppy)$_2$acac which was used as a guest material was observed, whereas an emission wavelength provided by the benzoxazole derivative of the present invention which was used as the host material (CzBOx or CzPBOx) was not observed. Therefore, it is confirmed that the benzoxazole derivatives of the present invention each serve as the host material of the light-emitting layer of the light-emitting element.

Example 4

In Example 4, a method for synthesizing 9-[4-(benzoxazol-2-yl)phenyl]-3-phenyl-9H-carbazole (abbreviation: CzBOxII) represented by Structural Formula (189), which is one of the benzoxazole derivatives of the present invention, will be specifically described.

(189)

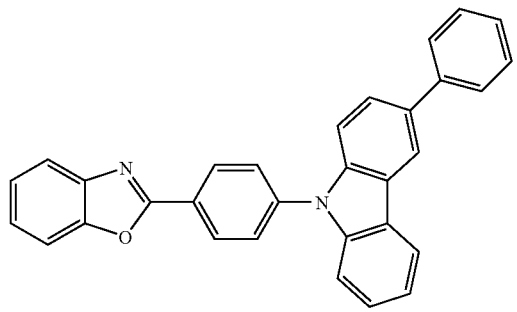

Synthesis of 9-(4-[Benzoxazol-2-yl)phenyl]-3-phenyl-9H-carbazole

A synthesis scheme of 9-(4-[benzoxazol-2-yl)phenyl]-3-phenyl-9H-carbazole is illustrated in (F-1).

(F-1)

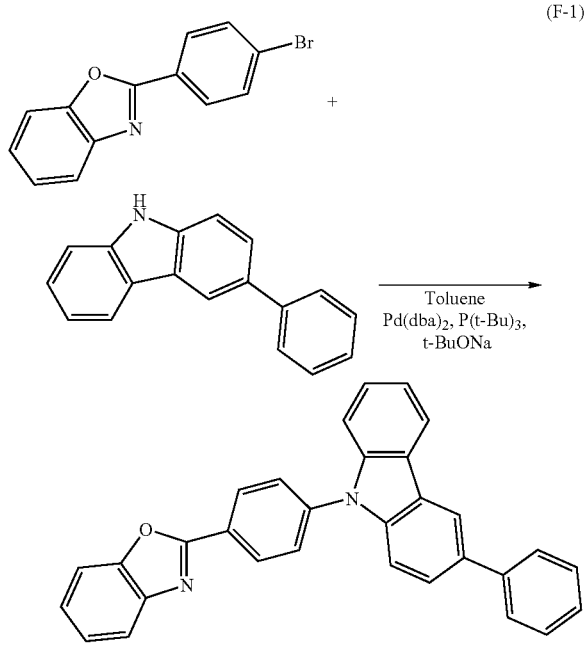

In a 100 mL three-neck flask were put 1.0 g (3.7 mmol) of 2-(4-bromophenyl)benzoxazole, 0.89 g (3.7 mmol) of 3-phenyl-9H-carabazole, and 0.77 g (8.0 mmol) of sodium tert-butoxide. The atmosphere in the flask was replaced with nitrogen. To this mixture were added 30 mL of toluene and 0.10 mL of a 10% hexane solution of tri(tert-butyl)phosphine. This mixture was degassed by reducing the pressure in the flask by using an aspirator. After that, the atmosphere in the flask was replaced with nitrogen. To this mixture was added 0.058 g (0.10 mmol) of bis (dibenzylideneacetone)palladium (0), followed by stirring under a nitrogen stream at 80° C. for 15 hours. After that, toluene was added to this mixture, and this suspension was washed with a saturated aqueous sodium carbonate solution and saturated brine in that order. After that, magnesium sulfate was added to the organic layer to dry it. Next, this mixture was suction filtered, whereby a filtrate was obtained.

The filtrate obtained was suction filtered through Celite 545 (produced by Kishida Chemical Co., Ltd., Catalog No. 020-14815). The resulting filtrate was concentrated to give a compound, which was then purified by silica gel column chromatography. The column chromatography was performed by using toluene as a developing solvent. The fraction obtained was concentrated to give a solid. This solid was recrystallized with a mixed solvent of chloroform and methanol to give 1.1 g of a white powdered solid in a yield of 68%.

Sublimation purification of 1.1 g of the white solid obtained was performed by a train sublimation method. Under a reduced pressure of 3.0 Pa and with an argon flow rate of 5 mL/min, the sublimation purification was performed at 250° C. for 15 hours, whereby 0.66 g of the resulting substance was obtained in a yield of 60%.

The compound obtained through the above synthesis method was measured by a nuclear magnetic resonance (NMR) method. The following are the measurement data: $^1$H NMR (CDCl$_3$, 300 MHz): δ=7.30-7.86 (m, 16H), 8.20 (d, J=8.3 Hz, 1H), 8.36 (sd, J=2.0 Hz, 1H), 8.51 (d, J=8.8 Hz, 2H)

Figure 19A:
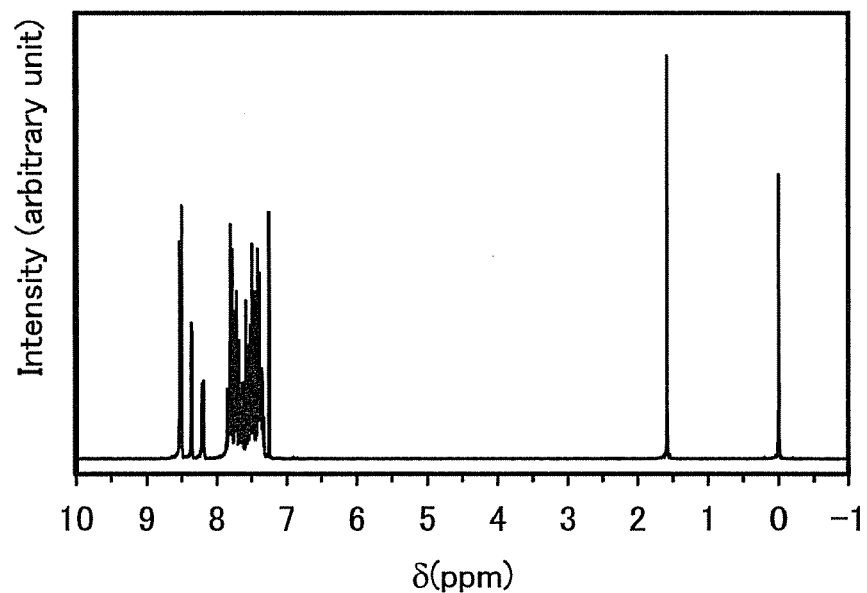
FIGS. 19A and 19B show NMR charts of CzBOxII.
Figure 19B:
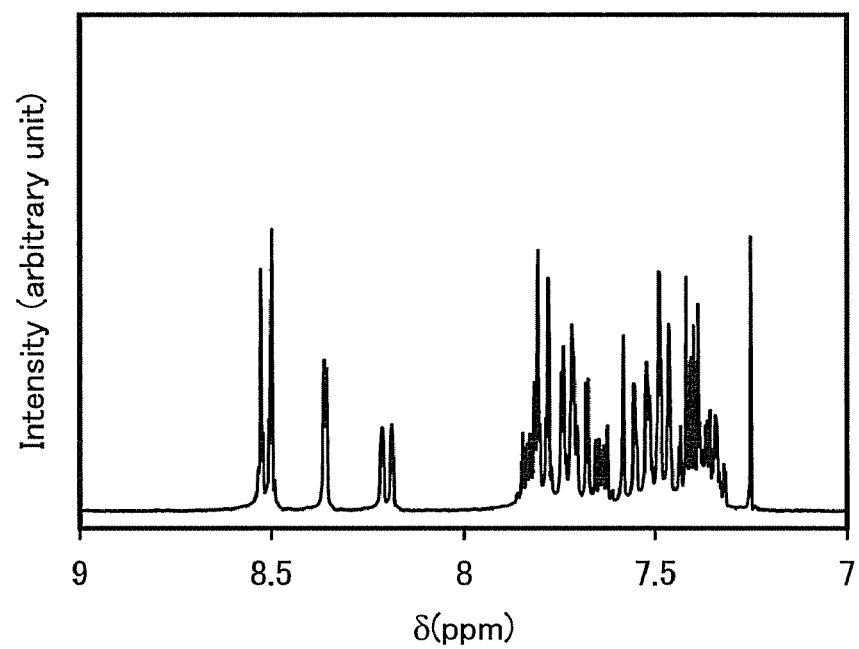

FIGS. 19A and 19B show $^1$H NMR charts. Note that FIG. 19B is a chart showing an enlarged part in the range of 7.0 ppm to 9.0 ppm of FIG. 19A. From the measurement results, it can be seen that 9-[4-(benzoxazol-2-yl)phenyl]-3-phenyl-9H-carbazole (abbreviation: CzBOxII) represented by Structural Formula (189), which was one of the benzoxazole derivatives of the present invention, was obtained.

Figure 20A:
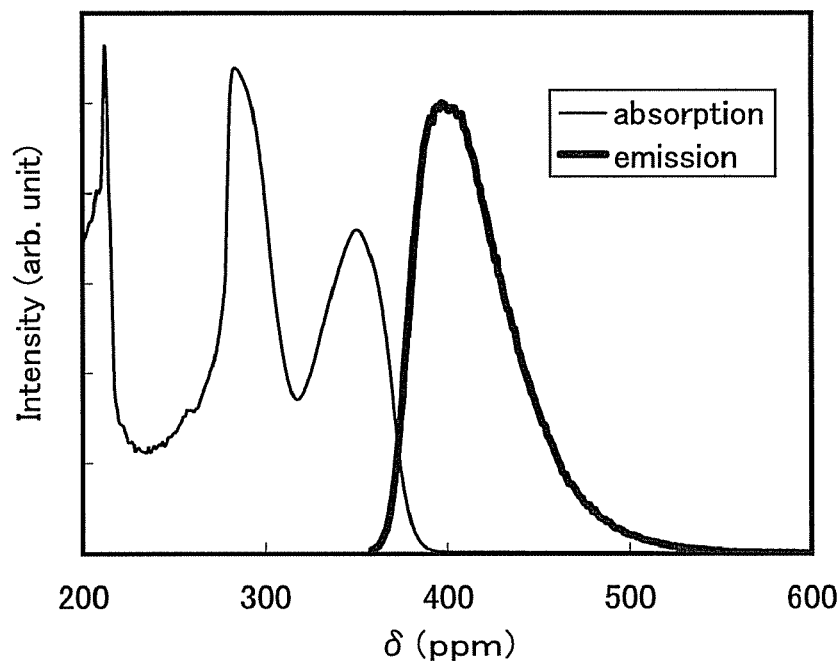
FIGS. 20A and 20B each show an absorption spectrum and an emission spectrum of CzBOxII.
Figure 20B:
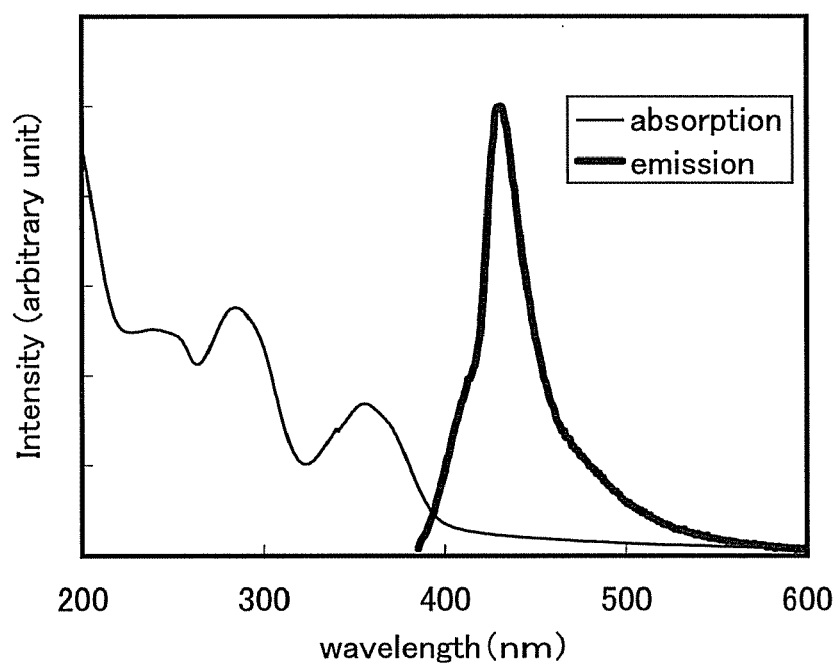

Further, FIG. 20A shows an absorption spectrum of a toluene solution of CzBOxII, and FIG. 20B shows an absorption spectrum of a thin film of CzBOxII. An ultraviolet-visible spectrophotometer (V-550, manufactured by JASCO Corporation) was used for the measurement. The absorption spectrum of the toluene solution of CzBOxII was obtained by subtracting the absorption spectrum of quartz from the absorption spectrum of a quartz cell that includes the toluene solution. In addition, the absorption spectrum of the thin film of CzBOxII was obtained by subtracting the absorption spectrum of quartz from the absorption spectrum of a sample formed by evaporating CzBOxII to a quartz substrate.

In FIGS. 20A and 20B, the horizontal axis represents wavelength (nm) and the vertical axis represents absorption intensity (arbitrary unit). With the toluene solution, an absorption peak was observed at around 348 nm. With the thin film, an absorption peak was observed at around 355 nm. Further, FIG. 20A shows an emission spectrum of the toluene solution of CzBOxII (an excitation wavelength of 348 nm). FIG. 20B shows an emission spectrum of the thin film of CzBOxII (an excitation wavelength of 365 nm). In FIGS. 20A and 20B, the horizontal axis represents wavelength (nm) and the vertical axis also represents emission intensity (arbitrary unit). With the toluene solution, the maximum emission wavelength was 399 nm (an excitation wavelength of 348 nm). With the thin film, the maximum emission wavelength was 430 nm (an excitation wavelength of 365 nm).

Further, by measurement with a photoelectron spectrometer (AC-2, manufactured by Riken Keiki, Co., Ltd.) in the atmosphere, the ionization potential of the thin film of CzBOxII was found to be 5.76 eV. As a result, it was understood that the HOMO level was −5.76 eV. Furthermore, with the use of the absorption spectrum data of the thin film of CzBOxII, the absorption edge was obtained by a Tauc plot assuming direct transition. The absorption edge was estimated as an optical energy gap, whereby the energy gap was 3.19 eV. From the obtained values of the energy gap and HOMO level, the LUMO level was −2.57 eV. Thus, it is found that CzBOxII has a large energy gap.

Furthermore, the oxidation-reduction characteristics of CzBOxII were measured in a manner similar to that of Example 1. Specifically, the oxidation characteristics were examined by 100 cycles of the measurement in which a scan for changing the potential of the working electrode with respect to the reference electrode from 0.055 V to 1.05 V and then from 1.05 V to 0.055 V was set to one cycle. Further, the reduction characteristics were examined by 100 cycles of the measurement in which a scan for changing the potential of the working electrode with respect to the reference electrode from −1.09 V to −2.45 V and then from −2.45 V to −1.09 V was set to one cycle. Note that the scan rate for the CV measurement was set to 0.1 V/s.

As a result, even after the 100 cycles of the measurement, significant changes in the peak position and peak intensity of the CV curves were not observed in the oxidation-reduction reactions. This demonstrates that CzBOxII which is a benzoxazole derivative of the present invention is significantly stable against repetition of oxidation-reduction reactions.

Example 5

In Example 5, a method for synthesizing 9-[4-(benzoxazol-2-yl)phenyl]-3,6-diphenyl-9H-carbazole (abbreviation: CzBOxIII) represented by Structural Formula (170), which is one of the benzoxazole derivatives of the present invention, will be specifically described.

(170)

Synthesis of 9-(4-[Benzoxazol-2-yl)phenyl]-3,6-diphenyl-9H-carbazole

A synthesis scheme of 9-(4-[benzoxazol-2-yl)phenyl]-3,6-diphenyl-9H-carbazole is illustrated in (G-1).

(G-1)

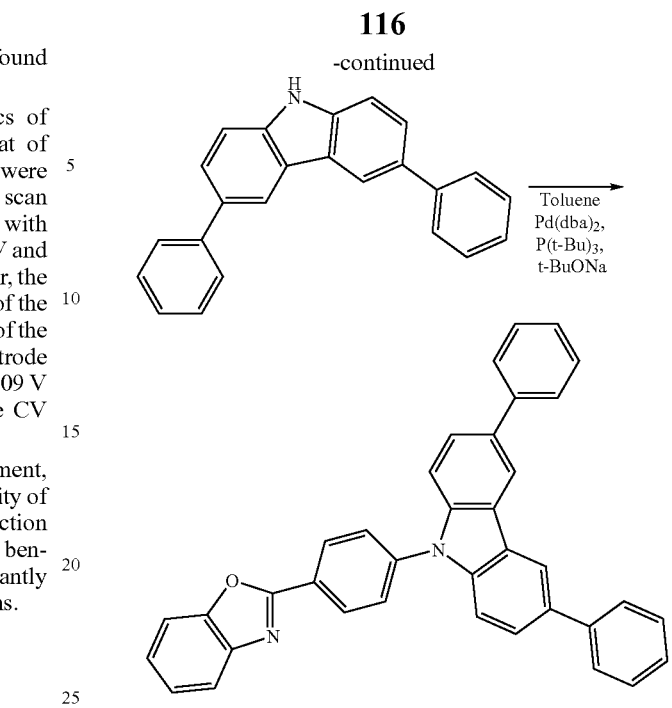

In a 100 mL three-neck flask were put 1.0 g (3.7 mmol) of 2-(4-bromophenyl)benzoxazole, 1.2 g (3.7 mmol) of 3,6-diphenyl-9H-carabazole, and 0.77 g (8.0 mmol) of sodium tert-butoxide. The atmosphere in the flask was replaced with nitrogen. To this mixture were added 15 mL of toluene and 0.10 mL of a 10% hexane solution of tri(tert-butyl)phosphine. This mixture was degassed by reducing the pressure in the flask by using an aspirator. After that, the atmosphere in the flask was replaced with nitrogen. To this mixture was added 0.030 g (0.052 mmol) of bis (dibenzylideneacetone)palladium(0), followed by stirring under a nitrogen stream at 80° C. for 5 hours. After that, toluene was added to this mixture, and this suspension was suction filtered through Celite 545 (produced by Kishida Chemical Co., Ltd., Catalog No. 020-14815), whereby a filtrate was obtained.

The filtrate obtained was washed with a saturated aqueous sodium hydrogen carbonate solution and saturated brine in that order. After that, magnesium sulfate was added to the organic layer to dry it. Next, this mixture was suction filtered. The resulting filtrate was concentrated to give a compound, which was then purified by silica gel column chromatography. The column chromatography was performed by using toluene as a developing solvent. The fraction obtained was concentrated to give a solid. This solid was recrystallized with a mixed solvent of dichloromethane and ethanol to give 1.8 g of a white powdered solid in a yield of 95%.

Sublimation purification of 1.8 g of the white solid obtained was performed by a train sublimation method. Under a reduced pressure of 4.0 Pa and with an argon flow rate of 5 mL/min, the sublimation purification was performed at 280° C. for 21 hours, whereby 1.5 g of the resulting substance was obtained in a yield of 83%.

The compound obtained through the above synthesis method was measured by a nuclear magnetic resonance (NMR) method. The following are the measurement data: $^1$H NMR (CDCl$_3$, 300 MHz): δ=7.32-7.86 (m, 20H), 8.41 (sd, J=2.0 Hz, 2H), 8.53 (d, J=8.8 Hz, 2H)

Figure 21A:
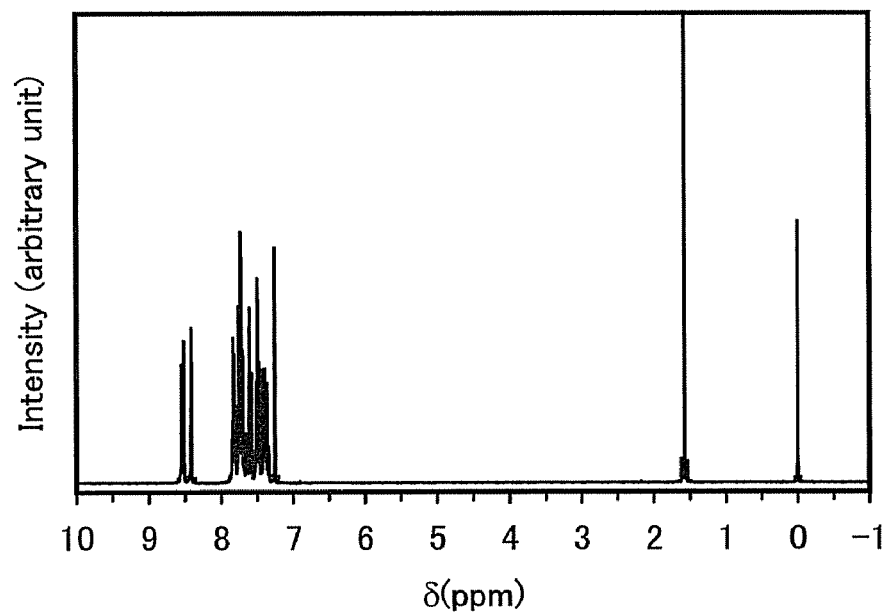
FIGS. 21A and 21B show NMR charts of CzBOxIII.
Figure 21B:
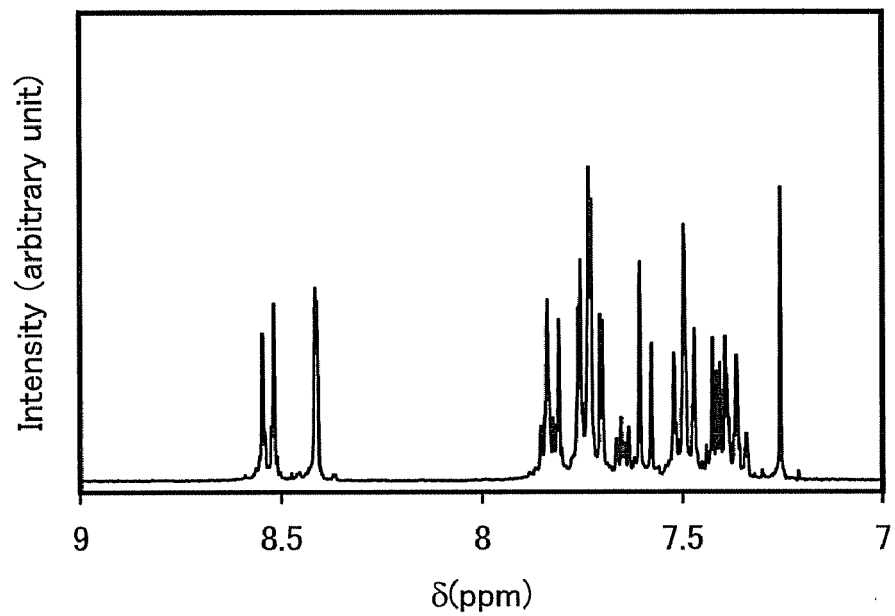

FIGS. 21A and 21B show $^1$H NMR charts. Note that FIG. 21B is a chart showing an enlarged part in the range of 7.0 ppm to 9.0 ppm of FIG. 21A. From the measurement results, it can be seen that 9-[4-(benzoxazol-2-yl)phenyl]-3,6-diphenyl-9H-carbazole (abbreviation: CzBOxIII) represented by the above Structural Formula (170), which is one of the benzoxazole derivatives of the present invention, is obtained.

Figure 22A:
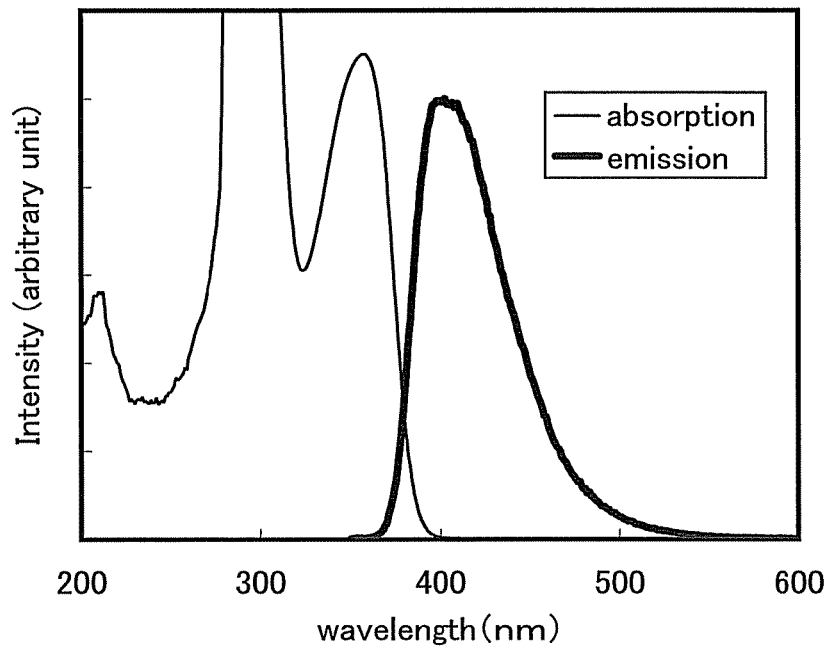
FIGS. 22A and 22B each show an absorption spectrum and an emission spectrum of CzBOxIII.
Figure 22B:
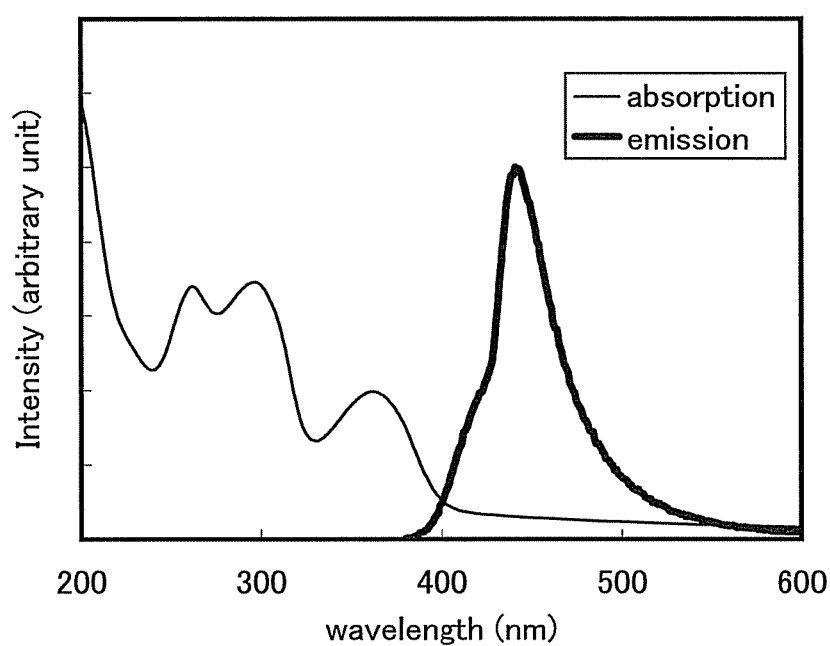

Further, FIG. 22A shows an absorption spectrum of a toluene solution of CzBOxIII, and FIG. 22B shows an absorption spectrum of a thin film of CzBOxIII. An ultraviolet-visible spectrophotometer (V-550, manufactured by JASCO Corporation) was used for the measurement. The absorption spectrum of the toluene solution of CzBOxIII was obtained by subtracting the absorption spectrum of quartz from the absorption spectrum of a quartz cell that includes the toluene solution. In addition, the absorption spectrum of the thin film of CzBOxIII was obtained by subtracting the absorption spectrum of quartz from the absorption spectrum of a sample formed by evaporating CzBOxIII to a quartz substrate.

In FIGS. 22A and 22B, the horizontal axis represents wavelength (nm) and the vertical axis represents absorption intensity (arbitrary unit). With the toluene solution, an absorption peak was observed at around 356 nm. With the thin film, an absorption peak was observed at around 362 nm. Further, FIG. 22A shows an emission spectrum of the toluene solution of CzBOxIII (an excitation wavelength of 356 nm). FIG. 22B shows an emission spectrum of the thin film of CzBOxIII (an excitation wavelength of 365 nm). In FIGS. 22A and 22B, the horizontal axis represents wavelength (nm) and the vertical axis also represents emission intensity (arbitrary unit). With the toluene solution, the maximum emission wavelength was 403 nm (an excitation wavelength of 356 nm). With the thin film, the maximum emission wavelength was 442 nm (an excitation wavelength of 365 nm).

Further, by measurement with a photoelectron spectrometer (AC-2, manufactured by Riken Keiki, Co., Ltd.) in the atmosphere, the ionization potential of the thin film of CzBOxIII was found to be 5.88 eV. As a result, it was understood that the HOMO level was −5.88 eV. Furthermore, with the use of the absorption spectrum data of the thin film of CzBOxIII, the absorption edge was obtained by a Tauc plot assuming direct transition. The absorption edge was estimated as an optical energy gap, whereby the energy gap was 3.15 eV. From the obtained values of the energy gap and HOMO level, the LUMO level was −2.73 eV. Thus, it is found that CzBOxIII has a large energy gap.

Furthermore, the oxidation-reduction characteristics of CzBOxIII were measured in a manner similar to that of Example 1. Specifically, the oxidation characteristics were examined by 100 cycles of the measurement in which a scan for changing the potential of the working electrode with respect to the reference electrode from 0.155 V to 1.05 V and then from 1.05 V to 0.155 V was set to one cycle. Further, the reduction characteristics were examined by 100 cycles of the measurement in which a scan for changing the potential of the working electrode with respect to the reference electrode from −1.04 V to −2.45 V and then from −2.45 V to −1.04 V was set to one cycle. Note that the scan rate for the CV measurement was set to 0.1 V/s.

As a result, even after the 100 cycles of the measurement, significant changes in the peak position and peak intensity of the CV curves were not observed in the oxidation-reduction reactions. This demonstrates that CzBOxIII which is a benzoxazole derivative of the present invention is significantly stable against repetition of oxidation-reduction reactions.

Example 6

In Example 6, a method for synthesizing 3-[4-(benzoxazol-2-yl)phenyl]-9-phenyl-9H-carbazole (abbreviation: PCBOx) represented by Structural Formula (332), which is one of the benzoxazole derivatives of the present invention, will be specifically described.

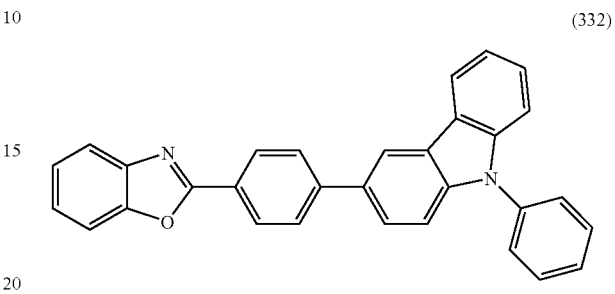

(332)

Synthesis of 3-[4-(Benzoxazol-2-yl)phenyl]-9-phenyl-9H-carbazole

A synthesis scheme of 3-[4-(benzoxazol-2-yl)phenyl]-9-phenyl-9H-carbazole is illustrated in (H-1).

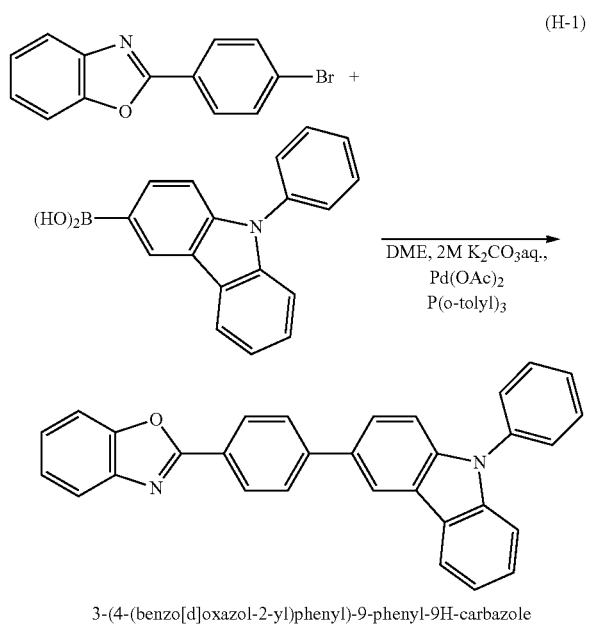

(H-1)

3-(4-(benzo[d]oxazol-2-yl)phenyl)-9-phenyl-9H-carbazole

In a 100 mL three-neck flask were put 0.95 g (3.5 mmol) of 2-(4-bromophenyl)benzoxazole, 1.0 g (3.5 mmol) of 9-phenyl-9H-carabazole-3-boronic acid, and 0.074 g (0.24 mmol) of tri(ortho-tolyl)phosphine. To this mixture were added 15 mL of 1,2-dimethoxyethane (abbreviation: DME) and 5 mL of a 2M potassium carbonate aqueous solution. This mixture was degassed under reduced pressure, and then the atmosphere in the flask was replaced with nitrogen. To this mixture was added 7.8 mg (0.035 mmol) of palladium(II) acetate, and the resulting mixture was stirred at 100° C. for 5 hours. After that, toluene was added to this mixture, and this suspension was washed with a saturated aqueous sodium carbonate solution and saturated brine in that order. Then, magnesium sulfate was added to the organic layer to dry it. Next, this mixture was suction filtered, whereby a filtrate was obtained.

The filtrate obtained was suction filtered through Celite 545 (produced by Kishida Chemical Co., Ltd., Catalog No. 020-14815). The resulting filtrate was concentrated to give a compound, which was then purified by silica gel column chromatography. The column chromatography was performed by using toluene as a developing solvent. The fraction obtained was concentrated to give a solid. This solid was recrystallized with chloroform and methanol to give 1.0 g of a light yellow powdered solid in a yield of 65%.

Sublimation purification of 1.0 g of the solid obtained was performed by a train sublimation method. Under a reduced pressure of 3.0 Pa and with an argon flow rate of 5 mL/min, the sublimation purification was performed at 250° C. for 16 hours, whereby 0.75 g of the resulting substance was obtained in a yield of 75%.

The compound obtained through the above synthesis method was measured by a nuclear magnetic resonance (NMR) method. The following are the measurement data: $^1$H NMR (CDCl$_3$, 300 MHz): δ=7.29-7.74 (m, 13H), 7.78-7.82 (m, 1H), 7.89 (d, J=9.3 Hz, 2H), 8.22 (d, J=6.8 Hz, 1H), 8.36 (d, J=8.3 Hz, 2H), 8.44 (sd, J=1.5 Hz, 1H)

Figure 23A:
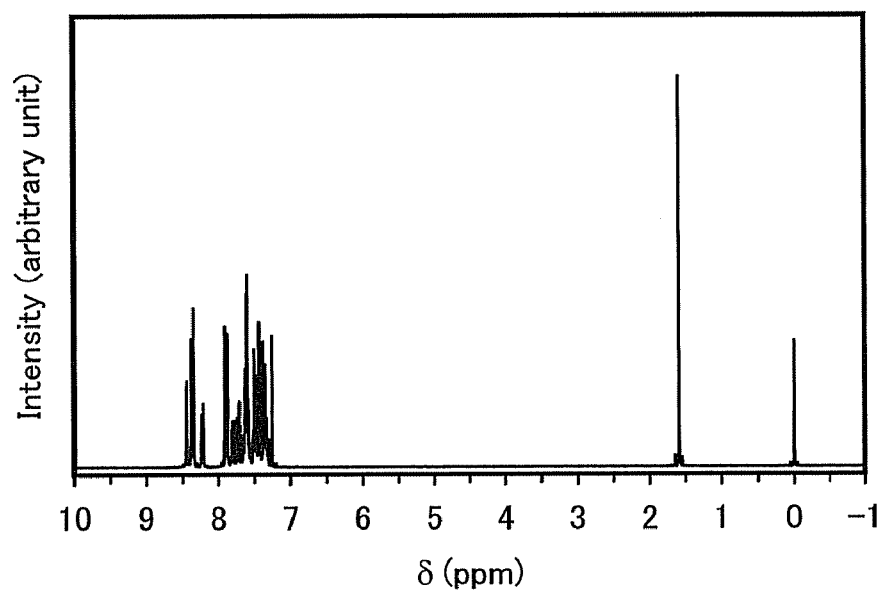
FIGS. 23A and 23B show NMR charts of PCBOx.
Figure 23B:
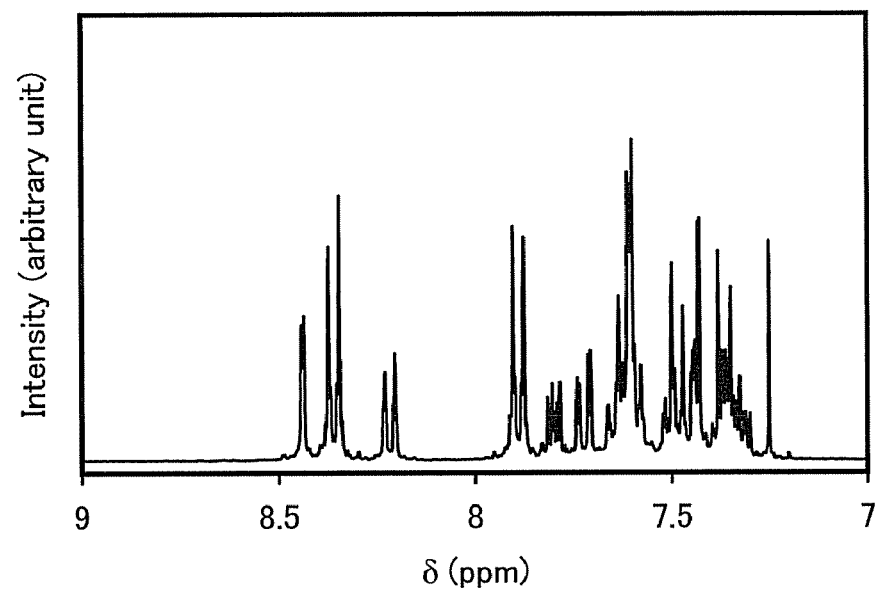

FIGS. 23A and 23B show $^1$H NMR charts. Note that FIG. 23B is a chart showing an enlarged part in the range of 7.0 ppm to 9.0 ppm of FIG. 23A. From the measurement results, it can be seen that 3-[4-(benzoxazol-2-yl)phenyl]-9-phenyl-9H-carbazole (abbreviation: PCBOx) represented by the above Structural Formula (332), which is one of the benzoxazole derivatives of the present invention, is obtained.

Figure 24A:
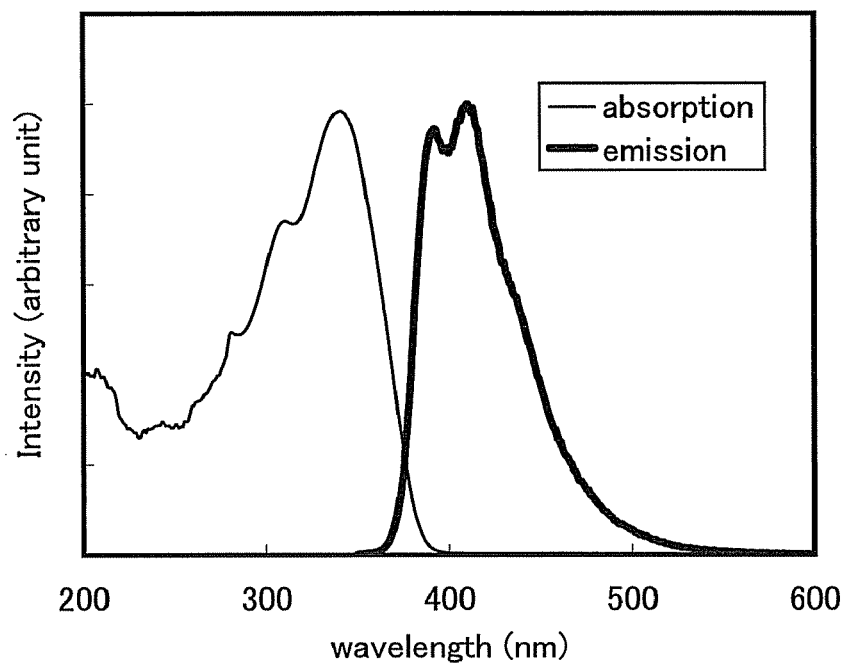
FIGS. 24A and 24B each show an absorption spectrum and an emission spectrum of PCBOx.
Figure 24B:
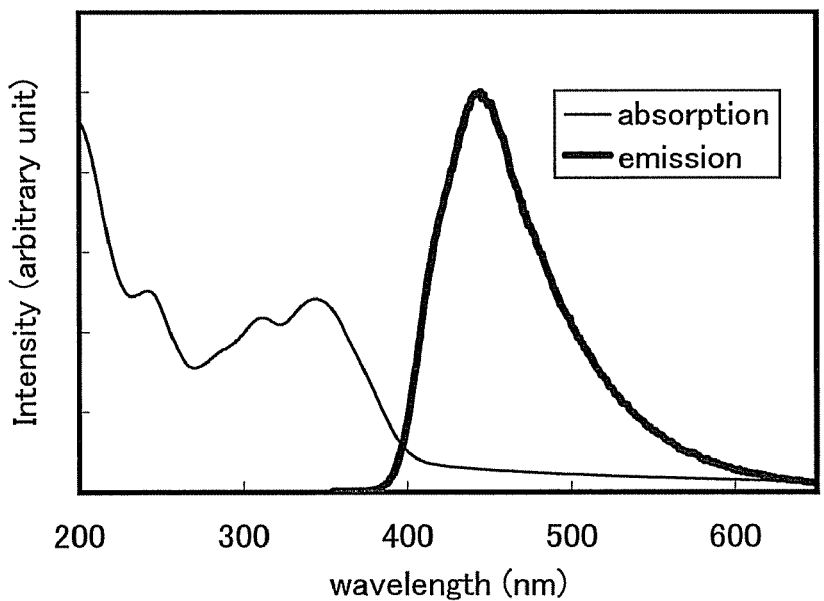

Further, FIG. 24A shows an absorption spectrum of a toluene solution of PCBOx, and FIG. 24B shows an absorption spectrum of a thin film of PCBOx. An ultraviolet-visible spectrophotometer (V-550, manufactured by JASCO Corporation) was used for the measurement. The absorption spectrum of the toluene solution of PCBOx was obtained by subtracting the absorption spectrum of quartz from the absorption spectrum of a quartz cell that includes the toluene solution. In addition, the absorption spectrum of the thin film of PCBOx was obtained by subtracting the absorption spectrum of quartz from the absorption spectrum of a sample formed by evaporating PCBOx to a quartz substrate.

In FIGS. 24A and 24B, the horizontal axis represents wavelength (nm) and the vertical axis represents absorption intensity (arbitrary unit). With the toluene solution, an absorption peak was observed at around 338 nm. With the thin film, an absorption peak was observed at around 344 nm. Further, FIG. 24A shows an emission spectrum of the toluene solution of PCBOx (an excitation wavelength of 338 nm). FIG. 24B shows an emission spectrum of the thin film of PCBOx (an excitation wavelength of 334 nm). In FIGS. 24A and 24B, the horizontal axis represents wavelength (nm) and the vertical axis also represents emission intensity (arbitrary unit). With the toluene solution, the maximum emission wavelengths were 392 nm and 411 nm (an excitation wavelength of 338 nm). With the thin film, the maximum emission wavelength was 444 nm (an excitation wavelength of 334 nm).

Further, by measurement with a photoelectron spectrometer (AC-2, manufactured by Riken Keiki, Co., Ltd.) in the atmosphere, the ionization potential of the thin film of PCBOx was found to be 5.58 eV. As a result, it was understood that the HOMO level was −5.58 eV. Furthermore, with the use of the absorption spectrum data of the thin film of PCBOx, the absorption edge was obtained by a Tauc plot assuming direct transition. The absorption edge was estimated as an optical energy gap, whereby the energy gap was 3.20 eV. From the obtained values of the energy gap and HOMO level, the LUMO level was −2.38 eV. Thus, it is found that PCBOx has a large energy gap.

Furthermore, the oxidation-reduction characteristics of PCBOx were measured in a manner similar to that of Example 1. Specifically, the oxidation characteristics were examined by 100 cycles of the measurement in which a scan for changing the potential of the working electrode with respect to the reference electrode from 0.064 V to 1.07 V and then from 1.07 V to 0.064 V was set to one cycle. Further, the reduction characteristics were examined by 100 cycles of the measurement in which a scan for changing the potential of the working electrode with respect to the reference electrode from −1.41 V to −2.45 V and then from −2.45 V to −1.41 V was set to one cycle. Note that the scan rate for the CV measurement was set to 0.1 V/s.

As a result, even after the 100 cycles of the measurement, significant changes in the peak position and peak intensity of the CV curves were not observed in the oxidation-reduction reactions. This demonstrates that PCBOx which is a benzoxazole derivative of the present invention is significantly stable against repetition of oxidation-reduction reactions.

Example 7

In Example 7, a method for synthesizing 3-[4-(benzoxazol-2-yl)phenyl]-6,9-diphenyl-9H-carbazole (abbreviation: PCBOxII) represented by Structural Formula (404), which is one of the benzoxazole derivatives of the present invention, will be specifically described.

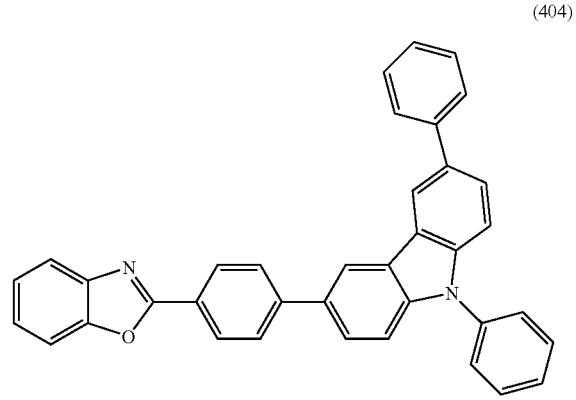

(404)

Synthesis of 3-[4-(Benzoxazol-2-yl)phenyl]-6,9-diphenyl-9H-carbazole

A synthesis scheme of 3-[4-(benzoxazol-2-yl)phenyl]-6,9-diphenyl-9H-carbazole is illustrated in (1-1).

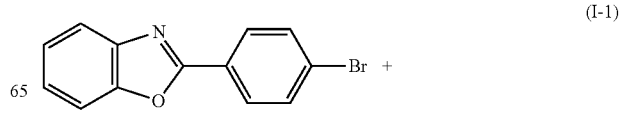

(I-1)

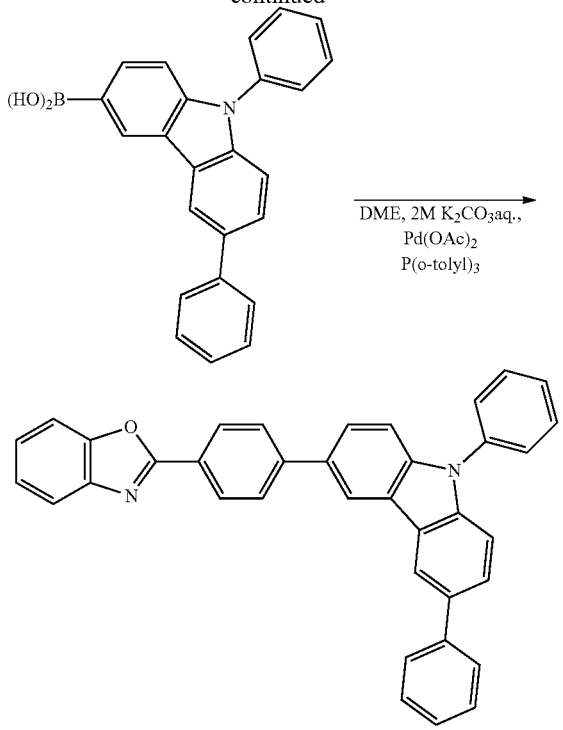

In a 100 mL three-neck flask were put 0.75 g (2.8 mmol) of 2-(4-bromophenyl)benzoxazole, 1.0 g (2.8 mmol) of 6,9-diphenyl-9H-carabazole-3-boronic acid, and 0.060 g (0.20 mmol) of tri(ortho-tolyl)phosphine. To this mixture were added 15 mL of 1,2-dimethoxyethane (abbreviation: DME) and 5 mL of a 2M potassium carbonate aqueous solution. This mixture was degassed under reduced pressure, and then the atmosphere in the flask was replaced with nitrogen. To this mixture was added 6.2 mg (0.028 mmol) of palladium(II) acetate, and the resulting mixture was stirred at 90° C. for 3 hours while being heated. After that, chloroform was added to this mixture, and this suspension was washed with a saturated aqueous sodium carbonate solution and saturated brine in that order. Then, magnesium sulfate was added to the organic layer to dry it. After that, this mixture was suction filtered. The resulting filtration was suction filtered through Celite 545 (produced by Kishida Chemical Co., Ltd., Catalog No. 020-14815), whereby a filtrate was obtained.

The filtrate obtained was concentrated to give a compound, which was then purified by silica gel column chromatography. The column chromatography was performed by using toluene as a developing solvent. The fraction obtained was concentrated to give a solid. This solid was recrystallized with chloroform and methanol to give 1.1 g of a white powdered solid in a yield of 77%.

Sublimation purification of 1.1 g of the white solid obtained was performed by a train sublimation method. Under a reduced pressure of 2.6 Pa and with an argon flow rate of 5 mL/min, the sublimation purification was performed at 270° C. for 14 hours, whereby 1.0 g of the resulting substance was obtained in a yield of 91%.

The compound obtained through the above synthesis method was measured by a nuclear magnetic resonance (NMR) method. The following are the measurement data: $^1$H NMR (CDCl$_3$, 300 MHz): δ=7.32-7.82 (m, 18H), 7.89 (d, J=8.3 Hz, 2H), 8.36 (d, J=8.8 Hz, 2H), 8.43 (sd, J=1.5 Hz, 1H), 8.48 (sd, J=1.5 Hz, 1H)

Figure 25A:
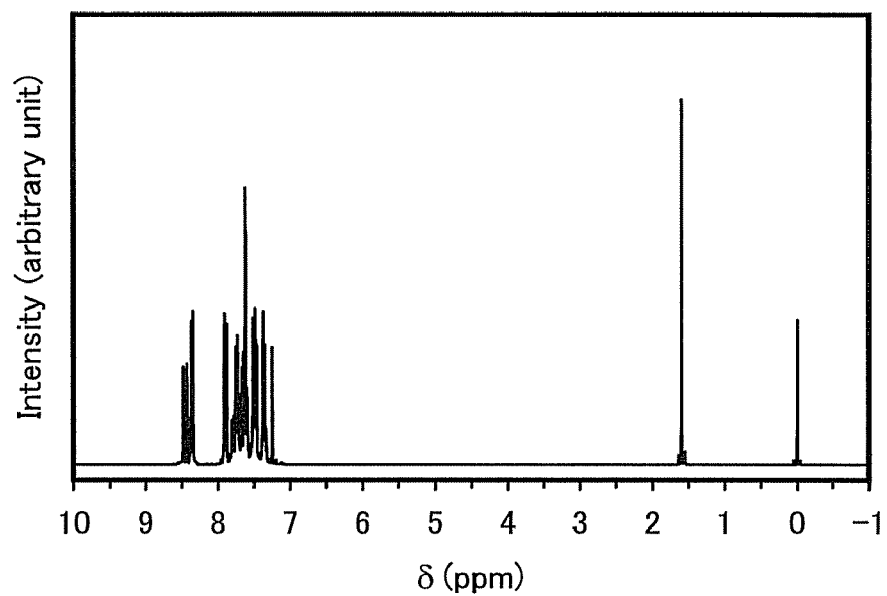
FIGS. 25A and 25B show NMR charts of PCBOxII.
Figure 25B:
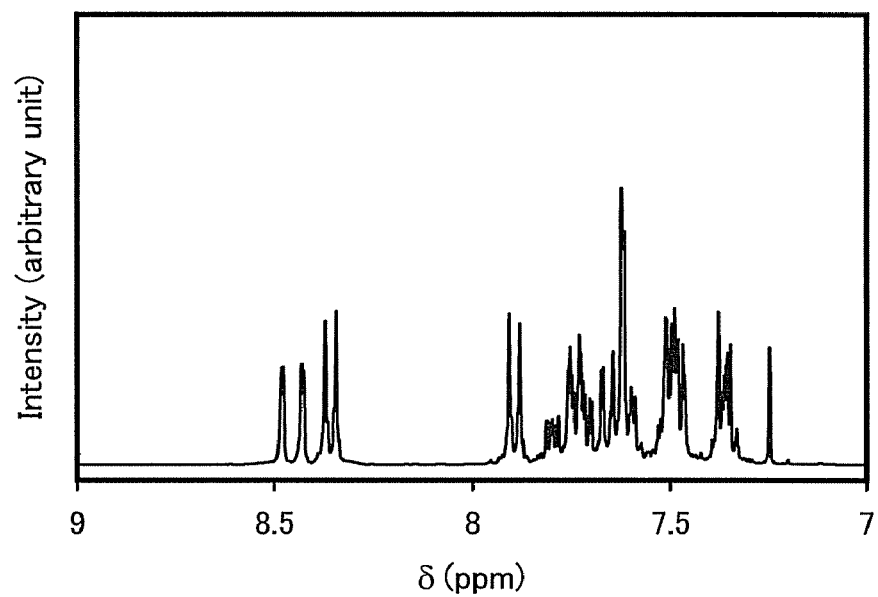

FIGS. 25A and 25B show $^1$H NMR charts. Note that FIG. 25B is a chart showing an enlarged part in the range of 7.0 ppm to 9.0 ppm of FIG. 25A. From the measurement results, it can be seen that 3-[4-(benzoxazol-2-yl)phenyl]-6,9-diphenyl-9H-carbazole (abbreviation: PCBOxII) represented by the above Structural Formula (404), which is one of the benzoxazole derivatives of the present invention, is obtained.

Figure 26A:
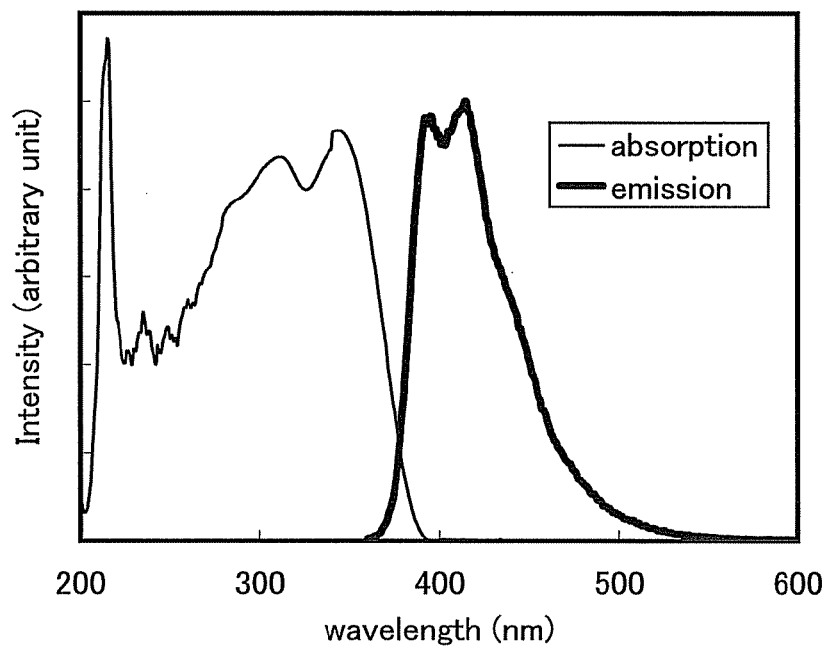
FIGS. 26A and 26B each show an absorption spectrum and an emission spectrum of PCBOxII.
Figure 26B:
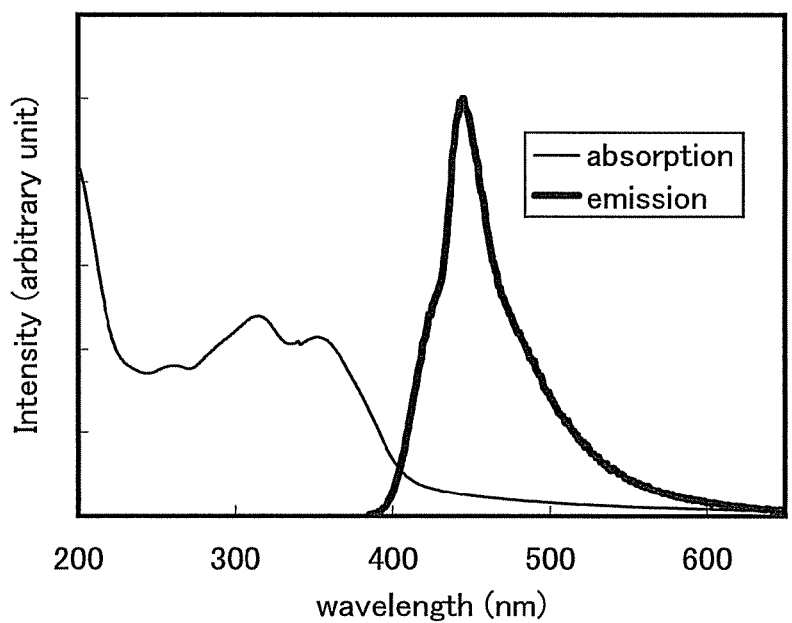

Further, FIG. 26A shows an absorption spectrum of a toluene solution of PCBOxII, and FIG. 26B shows an absorption spectrum of a thin film of PCBOxII. An ultraviolet-visible spectrophotometer (V-550, manufactured by JASCO Corporation) was used for the measurement. The absorption spectrum of the toluene solution of PCBOxII was obtained by subtracting the absorption spectrum of quartz from the absorption spectrum of a quartz cell that includes the toluene solution. In addition, the absorption spectrum of the thin film of PCBOxII was obtained by subtracting the absorption spectrum of quartz from the absorption spectrum of a sample formed by evaporating PCBOxII to a quartz substrate.

In FIGS. 26A and 26B, the horizontal axis represents wavelength (nm) and the vertical axis represents absorption intensity (arbitrary unit). With the toluene solution, an absorption peak was observed at around 341 nm. With the thin film, an absorption peak was observed at around 352 nm. Further, FIG. 26A shows an emission spectrum of the toluene solution of PCBOxII (an excitation wavelength of 341 nm). FIG. 26B shows an emission spectrum of the thin film of PCBOxII (an excitation wavelength of 369 nm). In FIGS. 26A and 26B, the horizontal axis represents wavelength (nm) and the vertical axis also represents emission intensity (arbitrary unit). With the toluene solution, the maximum emission wavelengths were 393 nm and 415 nm (an excitation wavelength of 341 nm). With the thin film, the maximum emission wavelength was 444 nm (an excitation wavelength of 369 nm).

Further, by measurement with a photoelectron spectrometer (AC-2, manufactured by Riken Keiki, Co., Ltd.) in the atmosphere, the ionization potential of the thin film of PCBOxII was found to be 5.64 eV. As a result, it was understood that the HOMO level was −5.64 eV. Furthermore, with the use of the absorption spectrum data of the thin film of PCBOxII, the absorption edge was obtained by a Tauc plot assuming direct transition. The absorption edge was estimated as an optical energy gap, whereby the energy gap was 3.12 eV. From the obtained values of the energy gap and HOMO level, the LUMO level was −2.52 eV. Thus, it is found that PCBOxII has a large energy gap.

Furthermore, the oxidation-reduction characteristics of PCBOxII were measured in a manner similar to that of Example 1. Specifically, the oxidation characteristics were examined by 100 cycles of the measurement in which a scan for changing the potential of the working electrode with respect to the reference electrode from 0.036 V to 1.02 V and then from 1.02 V to 0.036 V was set to one cycle. Further, the reduction characteristics were examined by 100 cycles of the measurement in which a scan for changing the potential of the working electrode with respect to the reference electrode from −1.36 V to −2.45 V and then from −2.45 V to −1.36 V was set to one cycle. Note that the scan rate for the CV measurement was set to 0.1 V/s.

As a result, even after the 100 cycles of the measurement, significant changes in the peak position and peak intensity of the CV curves were not observed in the oxidation-reduction reactions. This demonstrates that PCBOxII which is a benzoxazole derivative of the present invention is significantly stable against repetition of oxidation-reduction reactions.

Example 8

In Example 8, a method for forming a light-emitting element including the benzoxazole derivative described in Embodiment 1 as a host material of a light-emitting layer and measurement results of the element characteristics will be described. Specifically, Light-Emitting Element 3 formed using 9-[4-(benzoxazol-2-yl)phenyl]-3-phenyl-9H-carbazole (abbreviation: CzBOxII) described in Example 4 and Light-Emitting Element 4 formed using 9-[4-(benzoxazol-2-yl)phenyl]-3,6-diphenyl-9H-carbazole (abbreviation: CzBOxIII) described in Example 5 will be described.

Note that each element structure of the light-emitting elements of Example 8 is illustrated in FIG. 10, in which the light-emitting layer 1513 is formed using the above benzoxazole derivative that is one embodiment of the present invention. Structural Formulae of organic compounds used in Example 8 except those illustrated in Example 3 are illustrated below.

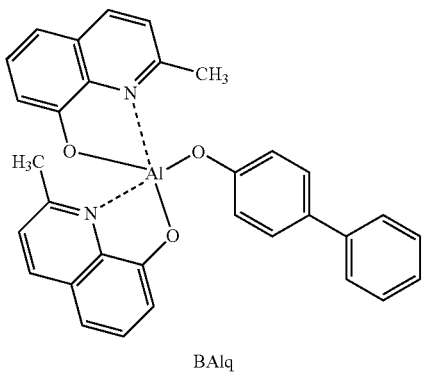

BAlq

First, indium oxide-tin oxide containing silicon oxide was deposited on the substrate 1501 which is a glass substrate by a sputtering method to form the first electrode 1502. Note that the thickness of the first electrode 1502 was set to 110 nm and the area of the electrode was set to 2 mm×2 mm.

Next, the EL layer 1503 including a stack of a plurality of layers is formed on the first electrode 1502. In Example 8, the EL layer 1503 has a structure in which the first layer 1511 which is a hole-inject layer, the second layer 1512 which is a hole-transport layer, the third layer 1513 which is a light-emitting layer, the fourth layer 1514 which is an electron-transport layer, and the fifth layer 1515 which is an electron-inject layer are stacked in that order.

The substrate 1501 provided with the first electrode 1502 was fixed on a substrate holder that was provided in a vacuum evaporation apparatus so that a surface provided with the first electrode 1502 faced downward. The pressure in the vacuum evaporation apparatus was reduced to approximately $10^{-4}$ Pa. Then, on the first electrode 1502, 4,4'-bis[N-(1-naphthyl)-N-phenylamino]biphenyl (abbreviation: NPB) and molybdenum(VI) oxide were co-evaporated to form the first layer 1511 which was a hole-inject layer. The thickness of the first layer 1511 was set to 40 nm, and the evaporation rate was controlled so that the mass ratio of NPB to molybdenum(VI) oxide was 4:1 (=NPB:molybdenum oxide). Note that a co-evaporation method refers to an evaporation method by which evaporation is conducted from a plurality of evaporation sources at the same time in one treatment chamber.

Next, a 20-nm-thick film was formed on the first layer 1511 by an evaporation method with resistance heating to form the second layer 1512 which was a hole-transport layer. Note that for the second layer 1512, 4-(9H-carbazol-9-yl)-4'-phenyltriphenylamine (abbreviation: YGAlBP) was used.

Next, the third layer 1513 which was a light-emitting layer was formed on the second layer 1512 by an evaporation method with resistance heating. As the third layer 1513 of Light-Emitting Element 3, 9-[4-(benzoxazol-2-yl)phenyl]-3-phenyl-9H-carbazole (abbreviation: CzBOxII) and bis(2-phenylpyridinato-N,$C^{2'}$)iridium(III) acetylacetonato (abbreviation: Ir(ppy)$_2$acac) were co-evaporated to form a 40-nm-thick film. Here, the evaporation rate was controlled so that the mass ratio of CzBOxII to Ir(ppy)$_2$acac was 1:0.06 (=CzBOxII:Ir(ppy)$_2$acac). Further, as the third layer 1513 of Light-Emitting Element 4, 9-[4-(benzoxazol-2-yl)phenyl]-3,6-diphenyl-9H-carbazole (abbreviation: CzBOxIII) and bis(2-phenylpyridinato-N,$C^{2'}$)iridium(III) acetylacetonato (abbreviation: Ir(ppy)$_2$acac) were co-evaporated to form a 40-nm-thick film. Here, the evaporation rate was controlled so that the mass ratio of CzPBOx to Ir(ppy)$_2$acac was 1:0.06 (=CzBOxIII:Ir(ppy)$_2$acac).

Furthermore, on the third layer 1513, a 10-nm-thick film of bis(2-methyl-8-quinolinolato)(4-phenylphenolato)aluminum (abbreviation: BAlq) and, thereon, a 20-nm-thick film of bathophenanthroline (abbreviation: BPhen) were formed by an evaporation method with resistive heating to form the fourth layer 1514 which was an electron-transport layer.

On the fourth layer 1514, a 1-nm-thick film of lithium fluoride (LiF) was formed as the fifth layer 1515 which was an electron-inject layer.

Lastly, a 200-nm-thick film of aluminum was formed by an evaporation method with resistance heating to form the second electrode 1504. Thus, Light-Emitting Elements 3 and 4 were fabricated.

The thus obtained Light-Emitting Elements 3 and 4 were sealed in a glove box containing a nitrogen atmosphere so as not to be exposed to air. Then, operation characteristics of these light-emitting elements were measured. Note that the measurement was carried out at room temperature (in the atmosphere kept at 25° C.).

Figure 27:
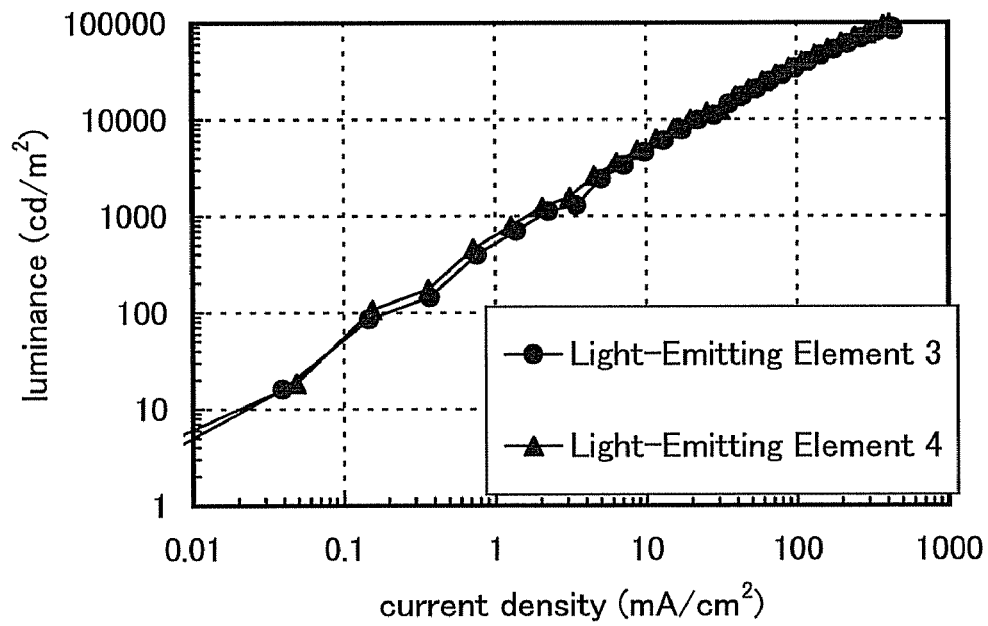
FIG. 27 shows current density vs. luminance characteristics of Light-Emitting Element 3 and a Light-Emitting Element 4.
Figure 28:
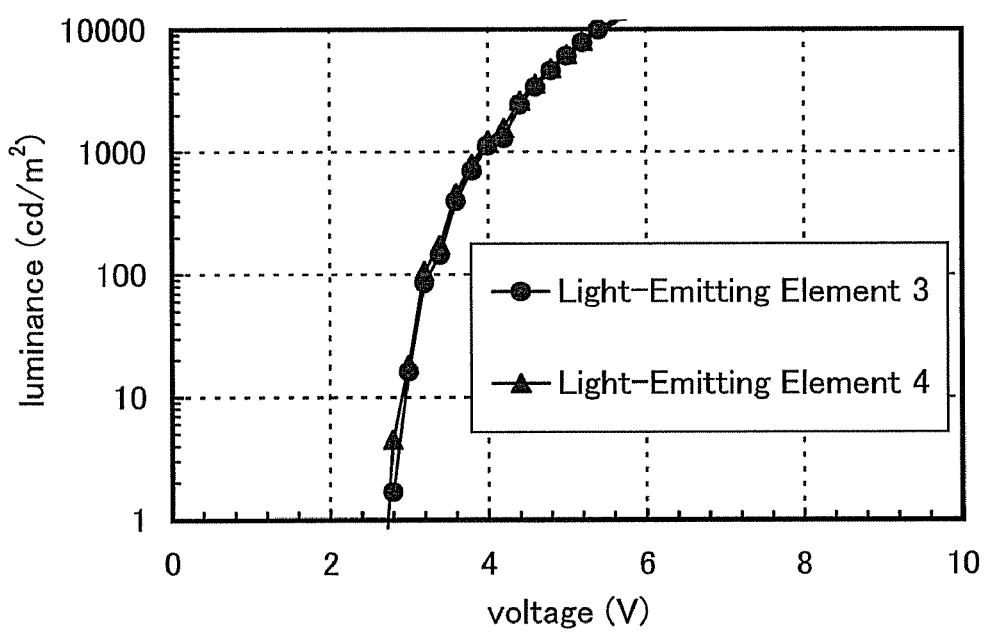
FIG. 28 shows voltage vs. luminance characteristics of Light-Emitting Element 3 and Light-Emitting Element 4.
Figure 29:
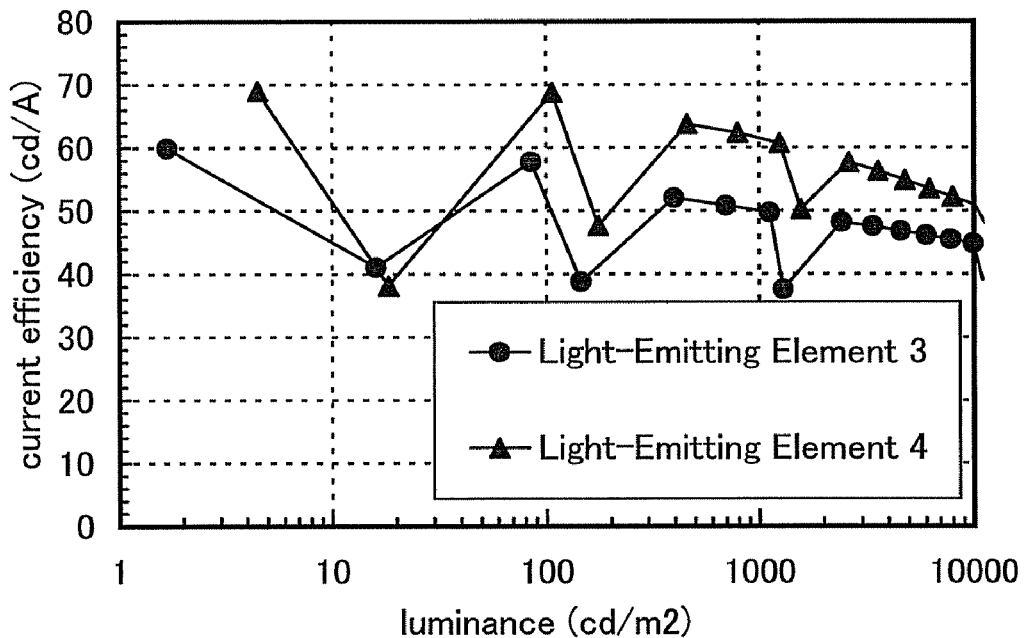
FIG. 29 shows luminance vs. current efficiency characteristics of Light-Emitting Element 3 and Light-Emitting Element 4.

FIG. 27 shows current density vs. luminance characteristics of Light-Emitting Elements 3 and 4. FIG. 28 shows voltage vs. luminance characteristics of Light-Emitting Elements 3 and 4. FIG. 29 shows luminance vs. current efficiency characteristics of Light-Emitting Elements 3 and 4. In FIG. 27, the vertical axis represents luminance (cd/m$^2$) and the horizontal axis represents current density (mA/cm$^2$). In FIG. 28, the vertical axis represents luminance (cd/m$^2$) and the horizontal axis represents voltage (V). In FIG. 29, the vertical axis represents current efficiency (cd/A) and the horizontal axis represents luminance (cd/m$^2$).

From FIG. 29, the maximum current efficiency of Light-Emitting Element 3 is 60 cd/A, and the maximum current efficiency of Light-Emitting Element 4 is 69 cd/A. This demonstrates that the light-emitting elements including the benzoxazole derivatives of the present invention have extremely high efficiency.

Figure 30:
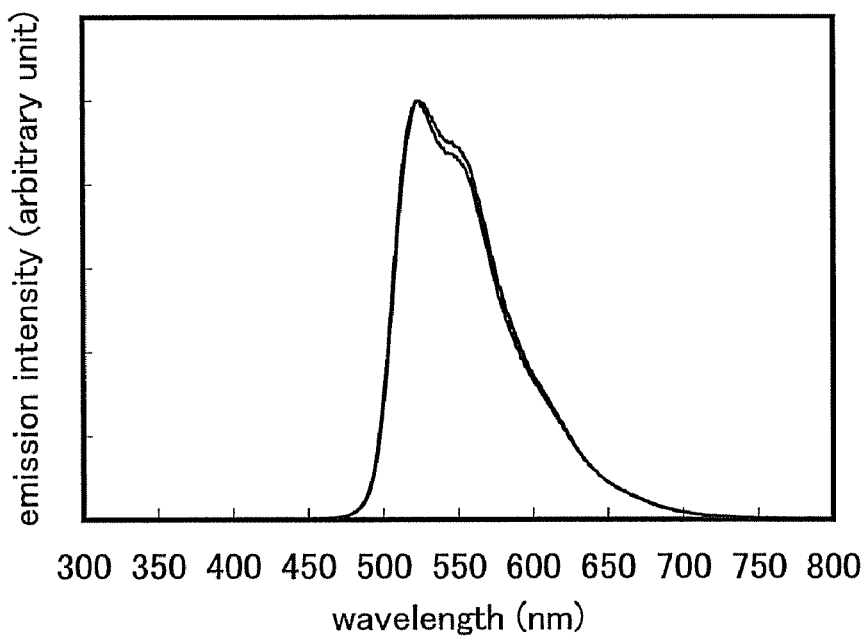
FIG. 30 shows emission spectra of Light-Emitting Element 3 and Light-Emitting Element 4.

FIG. 30 shows emission spectra of Light-Emitting Elements 3 and 4. As shown in FIG. 30, in each case of Light-Emitting Elements 3 and 4, an emission wavelength provided by Ir(ppy)$_2$acac which was used as a guest material was observed, whereas an emission wavelength provided by the benzoxazole derivative of the present invention which was used as the host material (CzBOxII or CzBOxIII) was not observed. Therefore, it is confirmed that the benzoxazole derivatives of the present invention each serve as the host material for the light-emitting layer of the light-emitting element.

Example 9

In Example 9, a method for forming a light-emitting element including the benzoxazole derivative described in Embodiment 1 as a host material of a light-emitting layer and measurement results of the element characteristics will be described. Specifically, Light-Emitting Element 3 formed using 3-[4-(benzoxazol-2-yl)phenyl]-9-phenyl-9H-carbazole (abbreviation: PCBOx) described in Example 6 will be described.

Note that an element structure of the light-emitting element of Example 9 is illustrated in FIG. 10, in which the light-emitting layer 1513 is formed using the above benzoxazole derivative that is one embodiment of the present invention. Since organic compounds used in Example 9 are the same as Examples 3 and 8, illustration of Structural Formulae of the organic compounds is omitted here.

First, indium oxide-tin oxide containing silicon oxide was deposited on the substrate 1501 which is a glass substrate by a sputtering method to form the first electrode 1502. Note that the thickness of the first electrode 1502 was set to 110 nm and the area of the electrode was set to 2 mm×2 mm.

Next, the EL layer 1503 including a stack of a plurality of layers is formed on the first electrode 1502. In Example 9, the EL layer 1503 has a structure in which the first layer 1511 which is a hole-inject layer, the second layer 1512 which is a hole-transport layer, the third layer 1513 which is a light-emitting layer, the fourth layer 1514 which is an electron-transport layer, and the fifth layer 1515 which is an electron-inject layer are stacked in that order.

The substrate 1501 provided with the first electrode 1502 was fixed on a substrate holder that was provided in a vacuum evaporation apparatus so that a surface provided with the first electrode 1502 faced downward. The pressure in the vacuum evaporation apparatus was reduced to approximately 104 Pa. Then, on the first electrode 1502, 4,4'-bis[N-(1-naphthyl)-N-phenylamino]biphenyl (abbreviation: NPB) and molybdenum(VI) oxide were co-evaporated to form the first layer 1511 which was a hole-inject layer. The thickness of the first layer 1511 was set to 40 nm, and the evaporation rate was controlled so that the mass ratio of NPB to molybdenum(VI) oxide was 4:1 (=NPB:molybdenum oxide). Note that a co-evaporation method refers to an evaporation method by which evaporation is conducted from a plurality of evaporation sources at the same time in one treatment chamber.

Next, a 20-nm-thick film was formed on the first layer 1511 by an evaporation method with resistance heating to form the second layer 1512 which was a hole-transport layer. Note that for the second layer 1512, 4-(9H-carbazol-9-yl)-4'-phenyltriphenylamine (abbreviation: YGAlBP) was used.

Next, the third layer 1513 which was a light-emitting layer was formed on the second layer 1512 by an evaporation method with resistance heating. As the third layer 1513 of Light-Emitting Element 5, 3-[4-(benzoxazol-2-yl)phenyl]-9-phenyl-9H-carbazole (abbreviation: PCBOx) and bis(2-phenylpyridinato-N,C$^{2'}$)iridium(III) acetylacetonato (abbreviation: Ir(ppy)$_2$acac) were co-evaporated to form a 40-nm-thick film. Here, the evaporation rate was controlled so that the mass ratio of PCBOx to Ir(ppy)$_2$acac was 1:0.06 (=PCBOx: Ir(ppy)$_2$acac).

Furthermore, on the third layer 1513, a 10-nm-thick film of bis(2-methyl-8-quinolinolato)(4-phenylphenolato)aluminum (abbreviation: BAlq) and, thereon, a 20-nm-thick film of bathophenanthroline (abbreviation: BPhen) were formed by an evaporation method with resistive heating to form the fourth layer 1514 which was an electron-transport layer.

On the fourth layer 1514, a 1-nm-thick film of lithium fluoride (LiF) was formed as the fifth layer 1515 which was an electron-inject layer.

Lastly, a 200-nm-thick film of aluminum was formed by an evaporation method with resistance heating to form the second electrode 1504. Thus, Light-Emitting Element 5 was formed.

The thus obtained Light-Emitting Element 5 was sealed in a glove box containing a nitrogen atmosphere so as not to be exposed to air. Then, operation characteristics of the light-emitting element were measured. Note that the measurement was carried out at room temperature (in the atmosphere kept at 25° C.).

Figure 31:
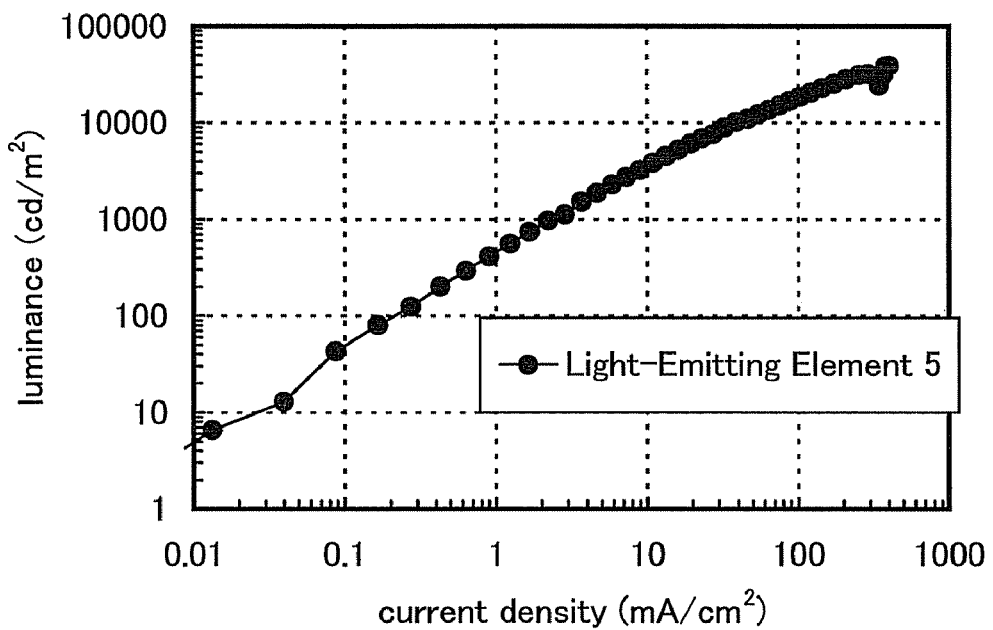
FIG. 31 shows current density vs. luminance characteristics of Light-Emitting Element 5.
Figure 32:
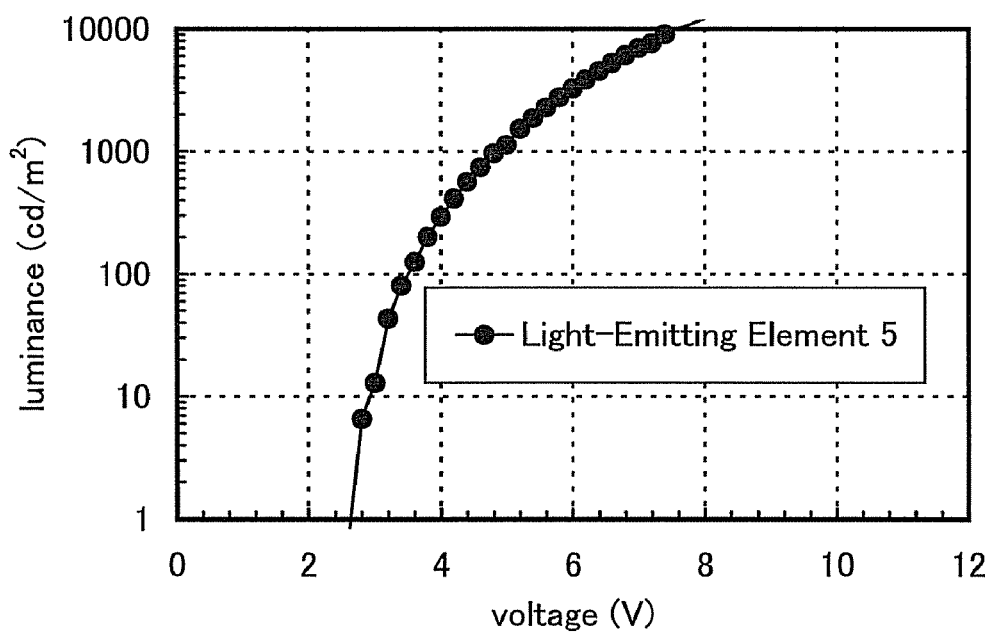
FIG. 32 shows voltage vs. luminance characteristics of Light-Emitting Element 5.
Figure 33:
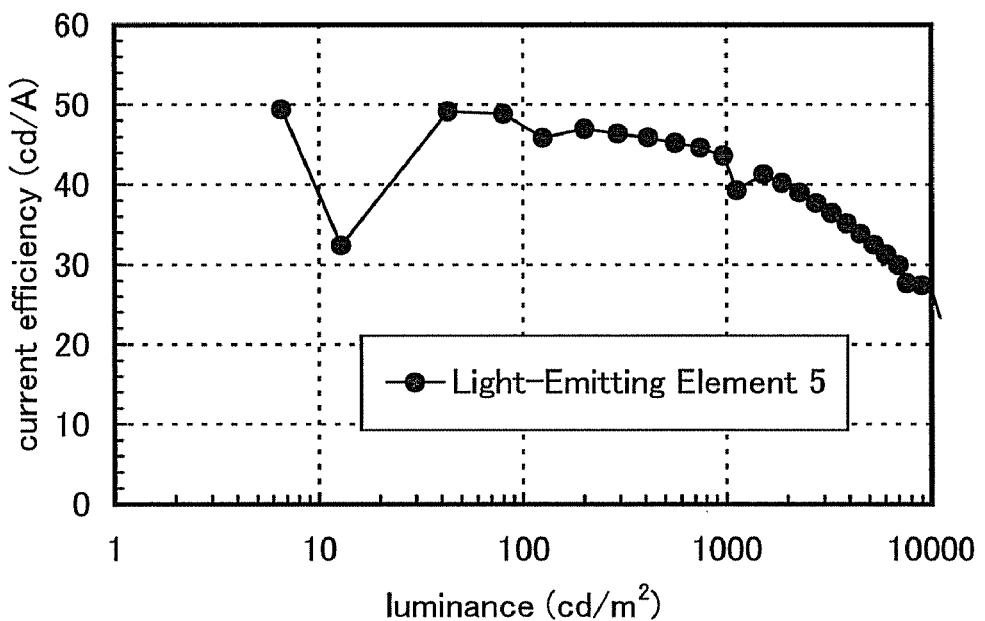
FIG. 33 shows luminance vs. current efficiency characteristics of Light-Emitting Element 5.

FIG. 31 shows current density vs. luminance characteristic of Light-Emitting Element 5. FIG. 32 shows voltage vs. luminance characteristic of Light-Emitting Element 5. FIG. 33 shows luminance vs. current efficiency characteristic of Light-Emitting Element 5. In FIG. 31, the vertical axis represents luminance (cd/m$^2$) and the horizontal axis represents current density (mA/cm$^2$). In FIG. 32, the vertical axis represents luminance (cd/m$^2$) and the horizontal axis represents voltage (V). In FIG. 33, the vertical axis represents current efficiency (cd/A) and the horizontal axis represents luminance (cd/m$^2$).

From FIG. 33, the maximum current efficiency of Light-Emitting Element 5 is 49 cd/A. This demonstrates that the light-emitting element including the benzoxazole derivative of the present invention has extremely high efficiency.

Figure 34:
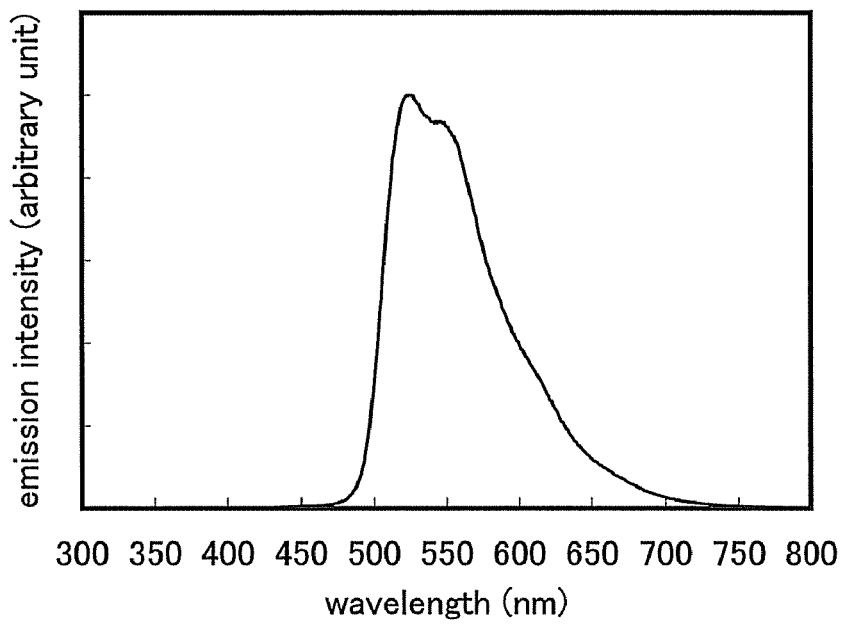
FIG. 34 shows an emission spectrum of Light-Emitting Element 5.

FIG. 34 shows an emission spectrum of Light-Emitting Element 5. As shown in FIG. 34, also in the case of Light-Emitting Element 5, an emission wavelength provided by Ir(ppy)$_2$acac which was used as a guest material was observed, whereas an emission wavelength provided by the benzoxazole derivative of the present invention which was used as the host material (PCBOx) was not observed. Therefore, it is confirmed that the benzoxazole derivative of the present invention serves as the host material of the light-emitting layer of the light-emitting element.

This application is based on Japanese Patent Application serial no. 2008-228252 filed with Japan Patent Office on Sep. 5, 2008 and Japanese Patent Application serial no. 2009-049170 filed with Japan Patent Office on Mar. 3, 2009, the entire contents of which are hereby incorporated by reference.

What is claimed is:

1. A benzoxazole derivative represented by Formula (G1),

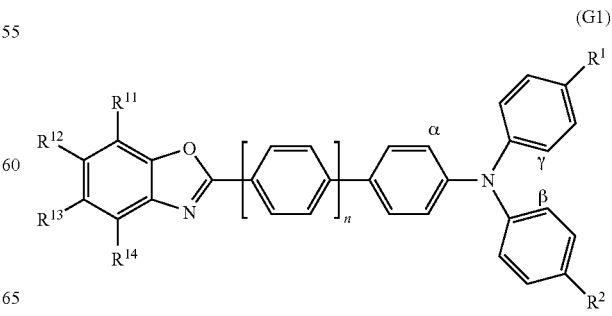

(G1)

wherein $R^1$ and $R^2$ independently represent any of a hydrogen atom, an alkyl group having 1 to 4 carbon atoms, and a substituted or unsubstituted aryl group having 6 to 13 carbon atoms, wherein $R^{11}$ to $R^{14}$ independently represent any of a hydrogen atom, a halogen, an alkyl group having 1 to 4 carbon atoms, and an unsubstituted aryl group having 6 to 10 carbon atoms, wherein a bond is formed between any two of α, β, and γ to form a carbazole skeleton, and wherein n is 0 to 3.

2. A benzoxazole derivative represented by Formula (G2),

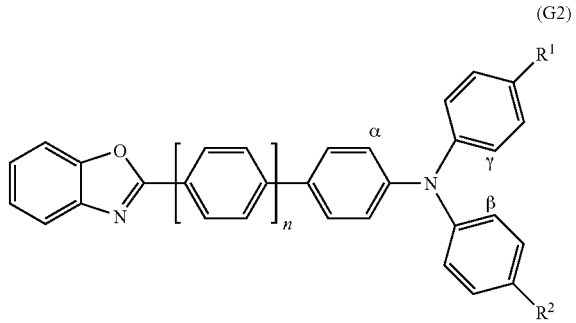

(G2)

wherein $R^1$ and $R^2$ independently represent any of a hydrogen atom, an alkyl group having 1 to 4 carbon atoms, and a substituted or unsubstituted aryl group having 6 to 13 carbon atoms, wherein a bond is formed between any two of α, β, and γ to form a carbazole skeleton, and wherein n is 0 to 3.

3. A benzoxazole derivative represented by Formula (G3),

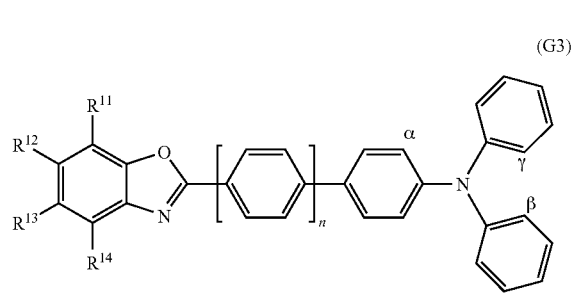

(G3)

wherein $R^{11}$ to $R^{14}$ independently represent any of a hydrogen atom, a halogen, an alkyl group having 1 to 4 carbon atoms, and an unsubstituted aryl group having 6 to 10 carbon atoms, wherein a bond is formed between any two of α, β, and γ to form a carbazole skeleton, and wherein n is 0 to 3.

4. The benzoxazole derivative according to claim 1, wherein any of $R^1$ and $R^2$ has a spiro ring structure.

5. The benzoxazole derivative according to claim 2, wherein any of $R^1$ and $R^2$ has a spiro ring structure.

6. The benzoxazole derivative according to claim 1, wherein n is 0, 1, or 2.

7. The benzoxazole derivative according to claim 2, wherein n is 0, 1, or 2.

8. The benzoxazole derivative according to claim 3, wherein n is 0, 1, or 2.

9. The benzoxazole derivative according to claim 2, wherein the bond is formed between β and γ, wherein the $R^1$ and $R^2$ each are a hydrogen atom, and wherein n is 0.

10. The benzoxazole derivative according to claim 2, wherein the bond is formed between β and γ, wherein the $R^1$ and $R^2$ each are a hydrogen atom, and wherein n is 1.

11. The benzoxazole derivative according to claim 2, wherein the bond is formed between α and β, wherein the $R^1$ and $R^2$ each are a hydrogen atom, and wherein n is 0.

12. A light-emitting element comprising an EL layer between a pair of electrodes, wherein the EL layer comprises the benzoxazole derivative according to claim 1.

13. A light-emitting element comprising an EL layer between a pair of electrodes, wherein the EL layer comprises the benzoxazole derivative according to claim 2.

14. A light-emitting element comprising an EL layer between a pair of electrodes, wherein the EL layer comprises the benzoxazole derivative according to claim 3.

\* \* \* \* \*